United States Patent
Blaber et al.

(10) Patent No.: US 9,840,544 B2
(45) Date of Patent: Dec. 12, 2017

(54) METHOD FOR DEVELOPMENT OF A PEPTIDE BUILDING BLOCK USEFUL FOR DE NOVO PROTEIN DESIGN

(71) Applicant: FLORIDA STATE UNIVERSITY RESEARCH FOUNDATION, INC., Tallahassee, FL (US)

(72) Inventors: Michael Blaber, Tallahassee, FL (US); Jihun Lee, Rockville, MD (US)

(73) Assignee: Florida State University Research Foundation, Tallahassee, FL (US)

( * ) Notice: Subject to any disclaimer, the term of this patent is extended or adjusted under 35 U.S.C. 154(b) by 78 days.

(21) Appl. No.: 14/751,207

(22) Filed: Jun. 26, 2015

(65) Prior Publication Data

US 2015/0361149 A1    Dec. 17, 2015

Related U.S. Application Data

(62) Division of application No. 13/044,723, filed on Mar. 10, 2011, now abandoned.

(60) Provisional application No. 61/312,843, filed on Mar. 11, 2010.

(51) Int. Cl.
| | |
|---|---|
| *C07K 14/50* | (2006.01) |
| *G06F 19/28* | (2011.01) |
| *G06F 19/16* | (2011.01) |
| *C07K 1/00* | (2006.01) |
| *G06F 19/22* | (2011.01) |

(52) U.S. Cl.
CPC ............... *C07K 14/50* (2013.01); *C07K 1/00* (2013.01); *G06F 19/16* (2013.01); *G06F 19/28* (2013.01); *G06F 19/22* (2013.01)

(58) Field of Classification Search
None
See application file for complete search history.

(56) References Cited

PUBLICATIONS

Brych et al. Protein Sci., 2003; 12(12): 2704-2718.*
Beadle, B. M. & Shoichet, B. K. (2002). J. Mol. Biol. 321, 285-296.
Otwinowski Z (1993) Proceedings of the CCP4 Study Weekend: "Data Collection and Processing", eds Sawyer L, Isaacs N, Bailey S (Science and Engineering Research Council, Daresbury Laboratory, England), pp. 56-62.
Bloom, J. D. et al. (2004). Biophys. J. 86, 2758-2764.
Bloom, J. D. et al. (2006). Proc. Natl Acad. Sci. USA, 103, 5869-5874.
Tokuriki, N. et al. (2008). PLoS Comput. Biol. 4,2, e1000002.
Auton, M. & Bolen, D. W. (2005). Proc. Natl Acad. Sci. USA, 102, 15065-15068.
Argos, P. & Palau, J. (1982). Int. J. Pept. Protein Res. 19, 380-393.
Padmanabhan, S. et al. (1990). Nature, 344, 268-270.
Blaber, M. et al. (1993). Science, 260, 1637-1640.
Kim, C. A. & Berg, J. M. (1993). Nature, 362, 267-27.
Minor, D. L., Jr & Kim, P. S. (1994). Nature, 367, 660-663.
Smith, C. K. et al. (1994). Biochemistry, 33, 5510-5517.
Pantoliano, M. W. et al. (1994). Biochemistry, 33, 10229-10248.
Chadhuri I et al. (2008). Proteins, 71, 795-803.
Zakrzewska, M. et al. (2005) J. Mol. Biol. 352, 860-875.
Bernett, M. J. et al. (2004). Proteins, 57, 626-634.
Culajay, J. F. et al. (2000). Biochemistry, 39, 7153-7158.
Lee, J. & Blaber, M. (2009). J. Mol. Biol. 393, 113-127.
Dorit RL et al. (1990) Science 250:1377-1382.
Panchenko AR et al. (1997) J Biol Chem 272:95-105.
Liu L et al. (2002) FEBS Lett 528:114-118.
Yadid I and Tawfik DS (2007) J Mal Biol 365:10-17.
Akanuma S et al. (2010) J Biochem 147:371-379.
Fersht, A. R. (1999). Kinetics of Protein Folding. Structure and Mechanism in Protein Science. W. H. Freeman and Co., New York.
Rocker B et al. (2001) Nat Struct Biol 8:32-36.
Akanuma S and Yamagishi A (2008) J Mal Biol 382:458-466.
Richter M et al. (2010) J Mol Biol 398:763-773.
Murzin AG et al. (1992) J Mol Biol 223:531-543.
Soskine M and Tawfik DS (2010) Nat Rev Genet 11:572-582.
Gibney BR et al. (1997) Curr Opin Chem Biol 1:537-542.
Schafmeister CE and Stroud RM (1998) Curr Opin Biotechnol 9:350-353.
Copeland RA et al. (1991) Arch Biochem Biophys 289:53-61.
Dubey VK et al. (2007) J Mol Biol 371:256-268.
Kim J et al. (2003) J Mol Biol 328:951-961.
Lee, J. et al. (2009). Acta Crystallogr., Sect. F. 65, 1097-1104.
Lee J and Blaber M (2009) J Mol Biol 393:128-139.
Lee J et al. (2008) J Mol Biol 377:1251-1264.
Arakawa T et al. (1993) Protein Eng 6:541-546.
Gimenez-Gallego et al. (1986) Biochem Biophys Res Commun 128:611-617.
Linemeyer DL et al. (1990) Growth Factors 3:287-298.
Ortega S et al. (1991) J Biol Chem. 266:5842-5846.
Zazo M et al. (1992) Gene 113:231-238.
Tsai PK et al. (1993) Pharm Res 10:649-659.
Gill SC and von Hippel PH (1989) Anal Biochem 182:319-326.
Pace CN and Scholtz JM (1997) Protein Structure: A Practical Approach, ed Creighton TE (Oxford Univ Press, Oxford), pp. 299-321.
Backmann J et al. (1998) J Mol Biol 284:817-833.
Jelesarov I and Lu M (2001) J Mol Biol 307:637-656.
Grek SB et al. (2001) Protein Pept Lett 6:429-436.
Otwinowski Z and Minor W(1997) Meth Enzymol 276:307-326.
Zwart PH et al. (2008) Methods Mol Biol 426:419-435.
Brunger AT (1992) Nature 355:472-475.
Emsley P and Cowtan K (2004) Coot: Model-building tools for molecular graphics. Acta Crystallogr, Sect D: Biol Crystallogr 60:2126-2132.

(Continued)

*Primary Examiner* — Michael Borin
(74) *Attorney, Agent, or Firm* — Christopher M. Ramsey; GrayRobinson, P.A.

(57) ABSTRACT

The present invention relates to a top-down symmetric deconstruction approach which provides a novel alternative means to successfully identify a useful polypeptide "building block" for subsequent "bottom-up" de novo design of target protein architecture. The present invention also pertains to a novel peptides isolated by top-down symmetric deconstruction which may be useful for design or directed evolution of novel proteins with novel functionalities.

21 Claims, 22 Drawing Sheets

(56) References Cited

PUBLICATIONS

Demeler B (2005) Modern Analytical Ultracentrifugation: Techniques and Methods, eds Scott DJ, Harding SE, Rowe AJ (Royal Society of Chemistry, Cambridge, UK), pp. 210-229.
Schuck P and Demeler B (1999) Biophys J 76:2288-2296.
Brookes E et al. (2010) Eur Biophys J 39:405-414.
Brookes EH and Demeler B (2007) Proceedings of the Ninth Annual Conference on Genetic and Evolutionary Computation (Association for Computing Machinery, London), pp. 361-368.
Demeler B and Brookes E (2008) Colloid Polym Sci 286:129-137.
Durchschlag (Durchschlag H (1986) Thermodynamic Data for Biochemistry and Biotechnology, edHinz H-J (Springer, Berlin), pp. 45-128.
J. Mol. Biol. 293, 333-342, Thornton, 1999.
Hecht, M. H. et al. (1990). Science, 249, 884-891.
Ghirlanda, G. et al. (2002). J. Mol. Biol. 319, 243-253.
Romero, P. et al. (2001). Proteins, 42, 38-48.
Bashkin, P. et al. (1989). Biochemistry, 28, 1737-1743.
Weiner, H. L. & Swain, J. L. (1989). Proc. Natl Acad. Sci. USA, 86, 2683-2687.
Chintala, S. K. et al. (1994). Arch. Biochem. Biophys. 310, 180-186.
Schreiber, G. et al. (1994) Structure, 2, 945-951.
Shoichet, B. K. et al. (1995). Proc. Natl Acad. Sci. USA, 92, 452-456.
Cold Spring Harbor Symp. Quant. Biol. 52, 521-526, Regan, L. & DeGrado, W. F. (1987).
Science, 241, 976-978, Regan and Degrado. (1989).
Trends Biochem Sci, 14, 304-309, Richardson and Richardson. (1989).
Proc. Natl. Acad. Sci. USA, 91, 8747-8751, Quinn, T. P. et al. (1994).
Science, 270, 935-941, Bryson, J. W. et al. (1995).
Protein Engineering, 16, 12, 971-977, Fu, X. et al. (2003).
J. Mol. Biol. 325, 163-174, Offredi, F. et al. (2003).
Protein Science, 2753-2765, Tsai, H. H. et al. (2004).
Bioinformatics, 22, 22, 2790-2799, Heinemann, M. et al. (2006).
Methods in Molecular Biol., 350, 189-204, Haspel, N. et al. (2007).
Comput. Biol. Chem. 33, 325-328 He, Y. et al. (2009).
Proc. Natl. Acad. Sci. USA, 104, 17656-17661, Andre, I. et al. (2007).
Proc. Natl Acad. Sci. USA, 93, 14249-14255, Wolynes, P. G. (1996).
Proc. Natl Acad. Sci. USA, 104, 2679-2684, Lowe, A. R. & Itzhaki, L. S. (2007).
Computers Chem. 17,2, 149-163, Wootton, J. C. & Federhen, S. (1993).
Proteins, 42, 38-48, Romero, P. et al. (2001).
Nature, 438, 878-881, Wright, C. F. et al. (2005).
Proc. Natl Acad. Sci. USA, 103, 6883-6888. Hoang, T. X. et al. (2006).
J Mol Evol 50:214-223, Mukhopadhyay, D (2000).
Ponting CP, Russell RB (2000) J Mol Biol 302:1041-1047.
Blaber, S. I. et al. (1999). Biophys. J. 77, 470-477.
Brych, S. R. et al. (2001). Protein Sci. 10, 2587-2599.
Brych, S. R. et al. (2003) Protein Sci. 12, 2704-2718.
Brych, S. R. et al. (2004). J. Mol. Biol. 344, 769-780.
Dubey, V. K. et al. (2005). Protein Sci. 14, 2315-2323.
Lee, J. & Blaber, M. (2011). Proc. Natl Acad. Sci. USA, 108, 126-130.
Blaber, M. et al. (1996). Biochemistry, 35, 2086-2094.
Corey, E. J. & Cheng, X. M. (1989).
C. A. Orengo et al., Protein Superfamilies and Domain Superfolds, 372 Nature 631-634 (1994).
Jaewon Kim et al., Alternative Type I and I' Turn Conformations in the β8/β9 β-hairpin of Human Acidic Fibroblast Growth Factor, 11 Protein Sci. 459-466 (2002).
Jaewon Kim et al., Sequence swapping Does Not Result in Conformation Swapping for the β4/β5 and β8/β9 β-hairpin Turns in Human Acidic Fibroblast Growth Factor, 14 Protein Sci. 351-359 (2005).
Zhang et al., Proc. Natl. Acad. Sci. U.S.A. 88:3446-3450, 1991.
Zhu et al., Science 251:90-93, 1991.
Habazettl et al., Nature 359:855-857, 1992.
Wolfson et al., Biochemistry 32:5327-5331, 1993.
McDonald and Hendrickson, Cell 73:421-424, 1993.
Andre et al., J. Virol. 72:1497-1503, 1998.
Karlin & Altschul, Proc. Natl. Acad. Sci. USA 1990; 87: 2264-2268.
Karlin & Altschul, Proc. Natl. Acad. Sci. USA 1993;90: 5873-5877.
Myers & Miller, CABIOS 1988; 4, 1, 11-17.
Pearson & Lipman, Proc. Natl. Acad. Sci. USA 1988; 85: 2444-2448.
Altschul & Gish, 1996, Local alignment statistics, Doolittle ed., Methods in Enzymology 266: 460-480.
Altschul et al., Journal of Molecular Biology 1990; 215: 403-410.
Gish & States, 1993; Nature Genetics 3: 266-272.
Sepulveda P et al. (1975) J Biol Chem 250:5082-5088.
Molecular Cloning: A Laboratory Manual, second edition (Sambrook et al. 1989).
Tang et al. (1978) Nature 271:618-621.
McLachlan AD (1979) J Mol Biol 133:557-563.
Inana G et al. (1983) Nature 302:310-315.
Tateno Y, et al. (1997) J Mol Evol 44:S38-S43.

* cited by examiner

| Protein | Sequence | ΔΔG (kJ/mol) | m-value (kJ/mol M) |
|---|---|---|---|
| FGF-1 | PKLLYCSNG G - - - HF L RI L P D G T V D G - - TRDRSDQH I QLSA E SVG<br>15    20              25         30        35    40        45    50  52<br>EVYIK S TETG - - - QY L IAMDT D G L LY G - - SQTPNEE C LF L ER L E E NH<br>55    60              65         70        75    80        85    90  93<br>YNTYIS KKHAEKNW F VGLKKN G SCKRGPRTHYGQKA I LFL P V S D<br>95    100              105         110        115    120        125    130    135    140 | — | 18.8 |
| SYM2 | PKLLYCSNG G - - - HF L RI L P D G T V D G - - TRDRSDQH I QLSA E SVG<br>15    20              25         30        35    40        45    50  52<br>EVYIK S TETG - - - QY L IAMDT D G L V Y G - - SQTPNEE C LF L ER L E E NH<br>55    60              65         70        75    80        85    90  93<br>YNTYIS KKHAEKNW F L GLKKN G SCKRGPRTHYGQKA I LFL P V S D<br>95    100              105         110        115    120        125    130    135    140 | 5.3 | 20.6 |
| SYM3 | PKLLYCSNG G - - - HF L RI L P D G T V D G - - TRDRSDQ H I Q F QLSA E SVG<br>15    20              25         30        35    40        45    50  52<br>EVYIK S TETG - - - QY L IAMDT D G L V Y G - - SQTPNEE C LF L ER L E E NH<br>55    60              65         70        75    80        85    90  93<br>YNTYIS KKHAEKNW F L GLKKN G SCKRGPRTHYGQKA I LFL P V S D<br>95    100              105         110        115    120        125    130    135    140 | 3.2 | 19.1 |

FIG. 8A

| | | | |
|---|---|---|---|
| SYM4 | P K L L Y C S N G G — — — H F L R I L P D G T I V D G — — T R D R S D Q H I Q F Q L S A E S V G<br>15　　　　　20　　　　　25　　　　　30　　　　　35　　　　　40　　　　　45　　　　　50　52<br>E V Y I K S T E T G — — — Q Y L A M D T D G L V Y G — — S Q T P N E E C L F L E R L E E N H<br>55　　　　　60　　　　　65　　　　　70　　　　　75　　　　　80　　　　　85　　　　　90　93<br>Y N T Y I S K K H A E K N W F L G L K K N G S V K R G P R T H Y G Q K A I L F L P V S S D<br>95　　　　　100　　　　　105　　　　　110　　　　　115　　　　　120　　　　　125　　　　　130　　　　　135　　　　　140 | 1.9 | 19.2 |
| SYM5 | P K L L Y C S N G G — — — H F L R I L P D G T I V D G — — T R D R S D Q H I Q F Q L S A E S V G<br>15　　　　　20　　　　　25　　　　　30　　　　　35　　　　　40　　　　　45　　　　　50　52<br>E V Y I K S T E T G — — — Q Y L A M D T D G L V Y G — — S Q T P N E E C L F L E R L E E N H<br>55　　　　　60　　　　　65　　　　　70　　　　　75　　　　　80　　　　　85　　　　　90　93<br>Y N T Y I S K K H A E K N W F L G I K K N G S V K R G P R T H Y G Q K A I L F L P V S S D<br>95　　　　　100　　　　　105　　　　　110　　　　　115　　　　　120　　　　　125　　　　　130　　　　　135　　　　　140 | 0.8 | 19.4 |
| SYM6 | P K L L Y C S N G G — — — H F L R I L P D G T I V D G — — T R D R S D Q H I Q F Q L S A E S V G<br>15　　　　　20　　　　　25　　　　　30　　　　　35　　　　　40　　　　　45　　　　　50　52<br>E V Y I K S T E T G — — — Q Y L A D T D G L V Y G — — S Q T P N E E C L F L E R L E E N H<br>55　　　　　60　　　　　65　　　　　70　　　　　75　　　　　80　　　　　85　　　　　90　93<br>Y N T Y I S K K H A E K N W F L G I I K K N G S V K R G P R T H Y G Q K A I L F L P V S S D<br>95　　　　　100　　　　　105　　　　　110　　　　　115　　　　　120　　　　　125　　　　　130　　　　　135　　　　　140 | 10.9 | 19.4 |

FIG. 8B

| SYM6AA | P K L L Y C S N G G H E L R I L P D G T V D G T R D R S D Q H I Q F Q L S A E S V G<br>55      60      65      70      75      80      85      90      93<br>E V Y I K S T E T G I Q Y L A I D T D G L V Y G I S - Q T P N E E C L F E R L E E N H<br>95     100   103/107   115   119 123   125   130   135   140<br>Y N T Y I S K K H G W F L G I I K K N G S I V K G T - H Y G Q K A I L F L P V S S D | −16.1 | 17.7 |
|---|---|---|---|
| SYM7AA | P K L L Y C S N G G H Y L R I L P D G T V D G T R D R S D Q H I Q F Q L S A E S V G<br>E V Y I K S T E T G I Q Y L A I D T D G L V Y G I S - Q T P N E E C L F E R L E E N H<br>Y N T Y I S K K H G W Y L G I I K K N G S I V K G T - H Y G Q K A I L F L P V S S D | −16.8 | ND |
| SYM8AA | P K L L Y C S N G G H Y L R I L P D G T V D G T R D R S D Q H C Q F Q L S A E S V G<br>E V Y I K S T E T G I Q Y L A I D T D G L V Y G I S - Q T P N E E C L F E R L E E N H<br>Y N T Y I S K K H G W Y L G I I K K N G S I V K G T - H Y G Q K A C L F L P V S S D | −17.1 | ND |

FIG. 8C

| Protein | Sequence | ΔΔG (kJ/mol) | m-value (kJ/mol M) |
|---|---|---|---|
| SYM8ΔΔ | P K L L Y C S N G G H Y L R I L P D G T V D G T R D R S D Q H C Q F Q L S A E S V G<br>E V Y I K S T E T G Q Y L A I D T D G L V Y G S – Q T P N E E C L F L E R L E E N H<br>Y N T Y I S K K H G I W Y L G I K N G I S V K G I T – H Y G Q K A I C L F L P L P V S S D | ND | ND |
| SYM9ΔΔ | P V L L Y C S N G G H Y L R I L P D G T V D G T R D R S D Q H I Q F Q L S A E S V G<br>E V Y I K S T E T G Q Y L A I D T D G L V Y G S – Q T P N E E C L F L E R L E E N H<br>Y N T Y I S K K H G I W Y L G I K N G I S V K G I T – H Y G Q K A I L F L V L P V S S D | -17.1 | 16.7 |
| SYM10ΔΔ | P V L L Y C S N G G H Y L R I L P D G T V D G T R D R S D Q H I Q F Q L S A E S V G<br>E V Y I K S T E T G Q Y L A I D T D G L V Y G S – Q T P N E E C L F L E R L E E N G<br>Y N T Y I S K K H G I W Y L G I K N G I S V K G I T – H Y G Q K A I L F L V L P V S S D | -37.9 | 17.9 |
| SYM11ΔΔ | P V L L Y C S N G G H Y L R I N P D G L V Y G S A E S V G<br>E V Y I K S T E T G Q Y L A I N P D G L V Y G S – Q T P N E E C L F L E R L E E N G<br>Y N T Y I S K K H G I W Y L G I I N P D G I S V K G I T – H Y G Q K A I T L F L V L P V S S D | -47.3<br><br>-41.6 | 16.2 |

FIG. 10

| Protein | Sequence | ΔΔG (kJ/mol) | m-value (kJ/mol M) |
|---|---|---|---|
| SYM11ΔA | PVLLYCSNGGHYLRINPDGTVDGLVYGS-QTPNEECIFERLEERLEESVG EVYIKSTETGQYLAINPDGLVYGS-QTPNEECFLERLEEN YNTYISKKHGWYLGIINPDGSVKGT-HYGQKAILFLVLPVSD | -41.6 | 16.2 |
| SYM12ΔA | PVLLYCSNGGHYLRINPDGTVDGLVYGS-QTPNEECIQFVSAESVG EVYIKSTETGQYLAINPDGLVYGS-QTPNEECFLVRLEEN YNTYISKKHGWYLGIINPDGSVKGT-HYGQKAILFLVLPVSD | -49.6 | 16.5 |
| SYM13ΔA | PVLLYCSNGGHYLRINPDGTVDGLVYGS-QTPNEECIQFVSAESVG EVYIKSTETGQYLAINPDGLVYGS-QTPNEECFLVRLEEN YVTYILSKKHGWYLGIINPDGSVKGT-HYGQKAILFLVLPVSD | -47.4 | 13.9 |
| Symfoil-1 | PVLLKSTETGQYLRINPDGTVDGTRDRSDQHIQFQVSPEIGGG EVLLKSTETGQYLRINPDGTVDGTRDRSDQHIQFQVSPEGGG EVLLKSTETGQYLRINPDGTVDGTRDRSDQHIQFQVSPEGGG | -8.2 | 18.5 |

FIG. 11

| Protein | Sequence | ΔΔG (kJ/mol) | m-value (kJ/mol/M) |
|---|---|---|---|
| Symfoil-1 | P V L L K S T E T G Q Y L R I N P D G T V D G T R D R S D Q H I Q F Q V S P E G G<br>15   20   25   30   35   40   45   50 52<br>E V L L K S T E T G Q Y L R I N P D G T V D G T R D R S D Q H I Q F Q V S P E G G<br>55   60   65   70   75 76A   80   85   90   93<br>E V L L K S T E T G Q Y L R I N P D G T V D G T R D R S D Q H I Q F Q V S P E G G<br>95   100 103107 110   115   119123123A125   130   135   140 | −8.2 | 18.5 |
| Symfoil-2 | P V L L K S T E T G Q Y L R I N P D G T V D G T R D R S D Q H I Q F Q I S P E G G<br>15   20   25   30   35   40   45   50 52<br>E V L L K S T E T G Q Y L R I N P D G T V D G T R D R S D Q H I Q F Q I S P E G G<br>55   60   65   70   75 76A   80   85   90   93<br>E V L L K S T E T G Q Y L R I N P D G T V D G T R D R S D Q H I Q F Q I S P E G G<br>95   100 103107 110   115   119123123A125   130   135   140 | −19.4 | 17.4 |
| Symfoil-3 | P V L L K S T E T G Q Y L R I N P D G T V D G T R D R S D Q H I Q F Q I S P E G N G<br>15   20   25   30   35   40   45   50 52<br>E V L L K S T E T G Q Y L R I N P D G T V D G T R D R S D Q H I Q F Q I S P E G N G<br>55   60   65   70   75 76A   80   85   90   93<br>E V L L K S T E T G Q Y L R I N P D G T V D G T R D R S D Q H I Q F Q I S P E G N G<br>95   100 103107 110   115   119123123A125   130   135   140 | −22.8 | 17.3 |

FIG. 13A

| | | | | | | | | | |
|---|---|---|---|---|---|---|---|---|---|
| | 15 | 20 | 25 | 30 | 35 | 40 | 45 | 50 | 52 |
| Symfoil-4 (X=T,V,P) | P V L L K S T E T G Q Y L R I N P D G T V D G T R D R S D [X] H I Q F Q I S P E G N G | | | | | | | | (T) -24.9  17.4 |
| | 55 | 60 | 65 | 70 | 75 76A | 80 | 85 | 90 | 93 |
| | E V L L K S T E T G Q Y L R I N P D G T V D G T R D R S D [X] H I Q F Q I S P E G N G | | | | | | | | (V) -30.0  15.4 |
| | 95 | 100 103 107 | 110 | 115 | 119 123 123A 125 | 130 | 135 | 140 | |
| | E V L L K S T E T G Q Y L R I N P D G T V D G T R D R S D [X] H I Q F Q I S P E G N G | | | | | | | | (P) -42.6  15.3 |
| | 15 | 20 | 25 | 30 | 35 | 40 | 45 | 50 | 52 |
| Difoil-4P | P V L L K S T E T G Q Y L R I N P D G T V D G T R D R S D P H I Q F Q I S P E G N G | | | | | | | | |
| | 55 | 60 | 65 | 70 | 75 76A | 80 | 85 | 90 | 93 |
| | E V L L K S T E T G Q Y L R I N P D G T V D G T R D R S D P H I Q F Q I S P E G N G | | | | | | | | |
| | 15 | 20 | 25 | 30 | 35 | 40 | 45 | 50 | 52 |
| Monofoil-4P | P V L L K S T E T G Q Y L R I N P D G T V D G T R D R S D P H I Q F Q I S P E G N G | | | | | | | | |

FIG. 13B

US 9,840,544 B2

METHOD FOR DEVELOPMENT OF A PEPTIDE BUILDING BLOCK USEFUL FOR DE NOVO PROTEIN DESIGN

RELATED APPLICATIONS AND INCORPORATION BY REFERENCE

This application is a divisional of U.S. patent application Ser. No. 13/044,723, filed Mar. 10, 2011, pending, entitled "Method for Development of Peptide Building Block Useful for De Novo Protein Design" which claims benefit of priority to U.S. provisional patent application Ser. No. 61/312,843 filed Mar. 11, 2010. Reference is made to U.S. provisional patent application Ser. No. 61/179,751 entitled "Fibroblast Growth Factor Mutants Having Improved Functional Half Life and Methods of Their Use" filed May 20, 2009 and U.S. provisional patent application Ser. No. 61/309,590 entitled "Fibroblast Growth Factor Mutants Having Improved Functional Half Life and Methods of Their Use" filed Mar. 2, 2010 and the entire contents and disclosures of these provisional applications are incorporated by reference.

FEDERAL FUNDING LEGEND

This invention was supported, in part, by the American Heart Association grant number: 0655133B. The federal government may have certain rights to this invention.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a top-down symmetric deconstruction approach to identify useful polypeptide "building blocks" for subsequent de novo design of target protein architecture as well as novel peptides isolated by top-down symmetric deconstruction which may be useful for design or directed evolution of novel proteins with novel functionalities.

BACKGROUND OF THE INVENTION

A long-standing goal in de novo protein design has been the exploitation of a hierarchical design strategy, utilizing appropriately designed peptide "building blocks," to spontaneously assemble (via oligomerization or concatenation) the desired target architecture (DeGrado W. F et al. (1987). Cold Spring Harbor Symp. Quant. Biol. 52, 521-526, Regan, L. & DeGrado, W. F. (1988). Science, 241, 976-978, Richardson, J. & Richardson, D. C. (1989). Trends Biochem. Sci. 14, 304-309, Hecht, M. H. et al. (1990). Science, 249, 884-891, Quinn, T. P. et al. (1994). Proc. Natl Acad. Sci. USA, 91, 8747-8751, Bryson, J. W. et al. (1995). Science, 270, 935-941, Fu, X. et al. (2003). Protein Eng. 16, 971-977, Offredi, F. et al. (2003). J. Mol. Biol. 325, 163-174, Tsai, H. H. et al. (2004). Protein Sci. 13, 2753-2765, Heinemann, M. & Panke, S. (2006). Bioinformatics, 22, 2790-2799, Haspel, N. et al. (2007). Methods Mol. Biol. 350, 189-204, He, Y. et al. (2009). Comput. Biol. Chem. 33, 325-328 and Armstrong, C. T. et al. (2009). Faraday Discuss. 143, 305-317). Such hierarchical design strategies are "bottom-up" in that polypeptides are designed from first principles to have folding and thermodynamic properties that promote correct assembly of the target structure.

Symmetric or periodic protein architecture is favored for such de novo design and offers a number of potential advantages. A symmetric design constraint substantially reduces the conformational search in design algorithms and can simplify folding simulations, thereby substantially accelerating the design calculations (Fu, X. et al. (2003). Protein Eng. 16, 971-977, He, Y. et al. (2009). Comput. Biol. Chem. 33, 325-328 and Andre, I. et al. (2007). Proc. Natl. Acad. Sci. USA, 104, 17656-17661). Elements of symmetry that result in efficient structural compaction during folding likely contribute to an efficient funneled energy landscape of folding (Wolynes, P. G. (1996). Proc. Natl Acad. Sci. USA, 93, 14249-14255).

Structural symmetry can also result in multiple folding nuclei with an associated redundancy within the folding pathway (Lowe, A. R. & Itzhaki, L. S. (2007). Proc. Natl Acad. Sci. USA, 104, 2679-2684). However, there are also significant unresolved questions regarding the practical limitations of symmetric protein design. For example, exact primary-structure symmetry within a symmetric architecture involves a substantial reduction in sequence complexity— one hallmark of natively unstructured proteins (Wootton, J. C. & Federhen, S. (1993). Computers Chem. 17, 149-163 and Romero, P. et al. (2001). Proteins, 42, 38-48). Exact primary structure symmetry within repeated domains provides opportunities for domain mismatches producing misfolded forms with near-native Gibbs energy, and low sequence identities could have a crucial and general role in safeguarding proteins against misfolding and aggregation (Wright, C. F. et al. (2005). Nature, 438, 878-881); furthermore, primary-structure symmetry is one feature of amyloid-type aggregates (Hoang, T. X. et al. (2006). Proc. Natl Acad. Sci. USA, 103, 6883-6888). Thus, while symmetric protein architecture offers attractive advantages for de novo design, there is a need for novel approaches to successfully identify foldable peptide building blocks from those that might otherwise misfold or aggregate.

Citation or identification of any document in this application is not an admission that such document is available as prior art to the present invention.

SUMMARY OF THE INVENTION

The present invention is based, in part, on Applicants' elucidation of the structural properties of subdomain fragments of a symmetric polypeptide derived from human fibroblast growth factor-1 [FGF-1, a protein belonging to the 3-fold symmetric β-trefoil fold; Protein Data Bank (PDB) code 2AFG] via a novel "top-down symmetric deconstruction (SD)" approach. This work provided experimental support for a "conserved architecture" model of evolution for the β-trefoil fold via gene duplication and fusion processes.

The present invention relates to a top-down symmetric deconstruction method for generating a polypeptide building block for design of a target architecture which may comprise: (a) choosing a protein having the target architecture, (b) imposing a cumulative symmetric constraint on core, turn and secondary structure by targeted mutagenesis, (c) retaining symmetric mutations if they are neutral or favorable to protein stability, folding and solubility, (d) analyzing sequences to identify candidate symmetric mutations, (e) analyzing the candidate symmetric mutations by molecular modeling, (f) determining a peptide sequence with a complete symmetric deconstruction and (g) fragmentation of the peptide sequence to determine the polypeptide building block, wherein polypeptide building block is generated for design of the target architecture.

In one embodiment, the target architecture may be a β-trefoil. In another embodiment, the protein may be fibroblast growth factor-1 (FGF-1). In another embodiment, the core may be a hydrophobic core. In another embodiment, the turn may be a reverse-turn. In another embodiment, the secondary structure may be a β-strand.

In particular, the step of imposing a cumulative symmetric constraint on core, turn and secondary structure by targeted mutagenesis may comprise application of specific transforms. The specific transforms may comprise symmetric deconstruction of the core, turn and secondary structure. Advantageously, the specific transforms may comprise symmetric deconstruction of a hydrophobic core, a reverse-turn and/or a β-strand. In particular, the specific transforms may be performed sequentially.

The present invention relates to a top-down SD method that produced the symmetric β-trefoil polypeptide, detailing the function, folding, and stability properties of intermediary forms between the FGF-1 starting protein and the final symmetric polypeptide, as well as structural details of an important intermediary mutant. The results describe a loss of FGF-1-specific function relatively early in the deconstruction process, while "function-competent" properties of folding and stability are maintained (or enhanced).

The invention also encompasses a peptide motif isolated by the above method of claim 1. Advantageously, the peptide motif may be Monofoil-4P, an end result of the top-down SD is a simple 42-amino-acid peptide building block that can subsequently be utilized in hierarchical bottom-up de novo protein design to generate a foldable, thermostable β-trefoil fold (either as a threefold repeat sequence within a single polypeptide or as a noncovalent homotrimer assembly).

Top-down SD therefore provides a novel alternative strategy in the successful development of peptide building blocks for subsequent bottom-up hierarchical protein design of symmetric protein architecture. In the case of the β-trefoil fold, a purely symmetric architecture is shown to be a satisfactory solution to the design of a soluble, foldable, thermostable protein architecture.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A illustrates the emergent architecture model of the evolutionary models of symmetry protein architecture (e.g., the β-trefoil fold). (Mukhopadhyay D (2000) J Mol Evol 50:214-223). The archaic peptide motif is autonomously folding, yielding simple single-domain architecture. Intermediate forms produced by gene duplication and fusion events have unique folds with increasing structural symmetry and complexity. The symmetric target architecture emerges upon the final gene duplication and fusion event.

FIG. 1B illustrates the conserved architecture model (Ponting C P, Russell R B (2000) J Mol Biol 302:1041-1047) of the evolutionary models of symmetry protein architecture. The archaic peptide is not an autonomously folding single-domain architecture; instead, it oligomerizes to yield the symmetric target architecture (e.g., β-trefoil fold). Intermediate forms produced by gene duplication and fusion events similarly oligomerize and reconstitute integral units of the symmetric target architecture. A final duplication and fusion event encodes the symmetric target architecture within a single polypeptide chain.

FIG. 2A illustrates the cumulative symmetric transforms applied to achieve a symmetric deconstruction of the β-trefoil architecture (beginning with FGF-1 and ending in the Monofoil and Difoil polypeptides) according to one embodiment of the present invention. Details for the set of intermediary mutants comprising the deconstruction are provided in Table 1.

FIG. 2B illustrates primary structures of the FGF-1 starting protein (SEQ ID NO: 4) and the resulting Symfoil-4P symmetric deconstruction (SEQ ID NO: 5) according to one embodiment of the present invention. Positions of exact threefold primary structure symmetry are indicated in yellow. The Monofoil-4P and Difoil-4P polypeptides were generated by the introduction of stop codons at positions 53 and 94 of the Symfoil-4P protein, respectively.

FIG. 3A is a ribbon diagram illustrating X-ray structure of FGF-1 protein according to one embodiment of the present invention. The ribbon representation of FGF-1 oriented down the threefold axis of symmetry and including select solvent structure.

FIG. 3B is a ribbon diagram illustrating X-ray structure of Symfoil-1 protein according to one embodiment of the present invention. The ribbon diagram shows similar representation of the Symfoil-1 mutant (also showing the location of a bound Tris molecule). The main-chain atoms (ribbon representation) are colored red, green, and blue for subdomains 1, 2, and 3, respectively. The set of 21 hydrophobic core residues (Corey, Pauling, Koltun coloring) are in shown in wireframe representation.

FIG. 3C is a ribbon diagram illustrating X-ray structure of Monofoil-4P protein according to one embodiment of the present invention. The ribbon diagram shows overlay of the repeating trefoil-fold subdomains of Symfoil-1. The mainchain atoms (ribbon representation) are colored red, green, and blue for subdomains 1, 2, and 3, respectively. The set of 21 hydrophobic core residues (Corey, Pauling, Koltun coloring) are in shown in wireframe representation.

Figure 5A:
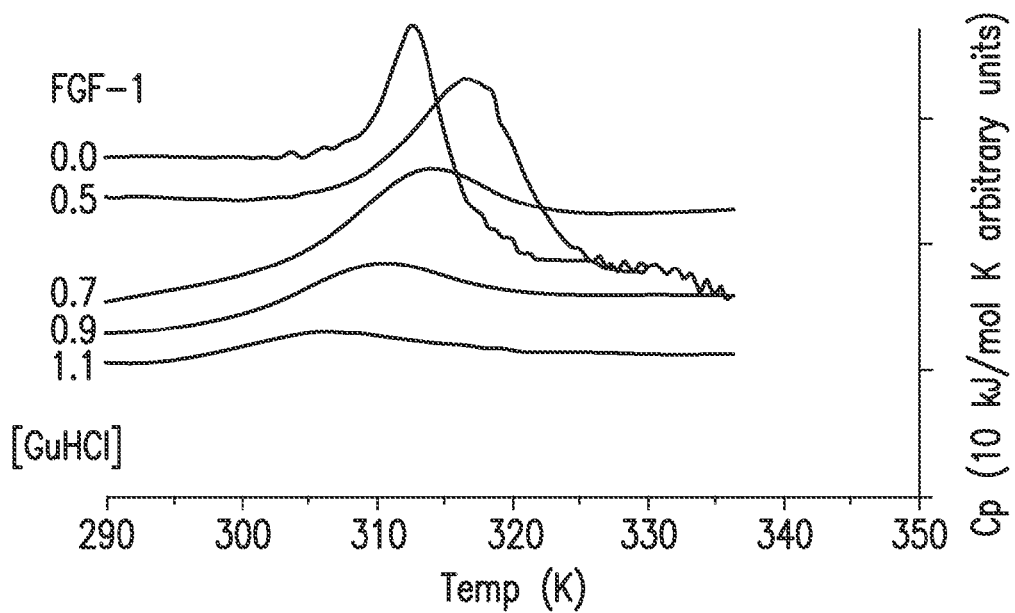

FIG. 5A is a graph illustrating differential scanning calorimetry (DSC) endotherms of FGF-1 protein in the presence of varying concentrations of GuHCl according to one embodiment of the present invention. The graph shows DSC endotherms of FGF-1 in 20 mM N-(2-acetamido)iminodiacetic acid, 0.1 M NaCl, pH6.6, and with the indicated concentrations of guanidine hydrochloride. FGF-1 undergoes irreversible thermal denaturation in the absence of ~0.6 MGuHCl.

Figure 5B:
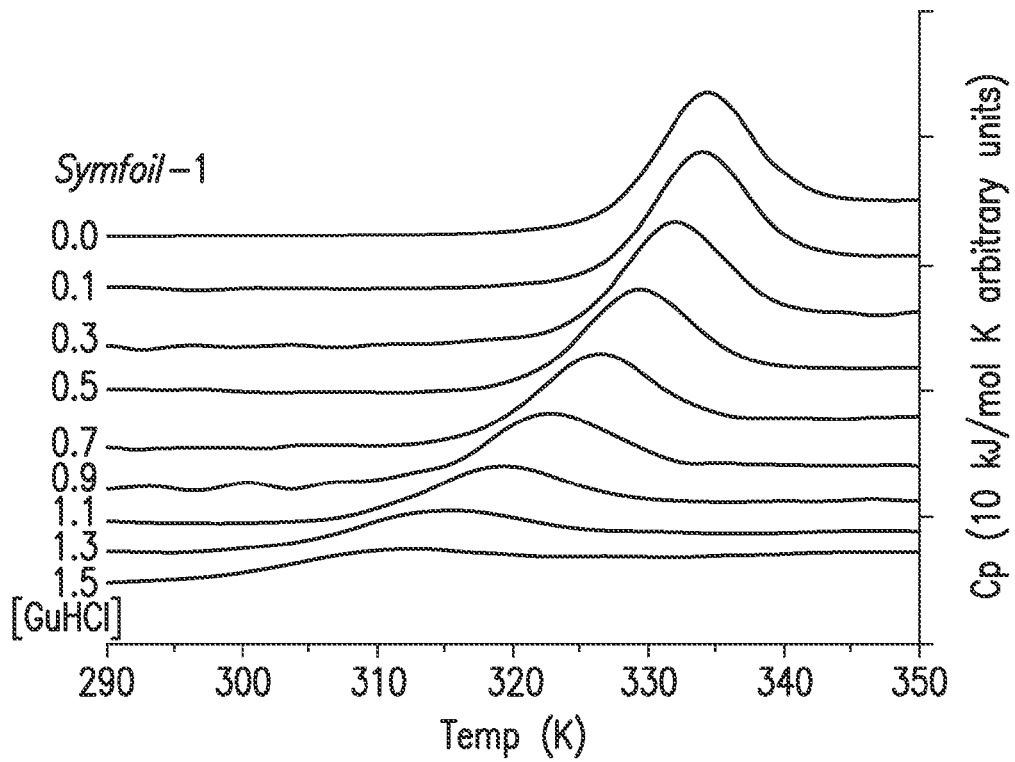

FIG. 5B is a graph illustrating DSC endotherms for the Symfoil-1 mutant in the same buffer conditions as in FIG. 5A. Unlike FGF-1, the Symfoil-1 mutant exhibits reversible, two-state thermal denaturation under all buffer conditions.

Figure 6:
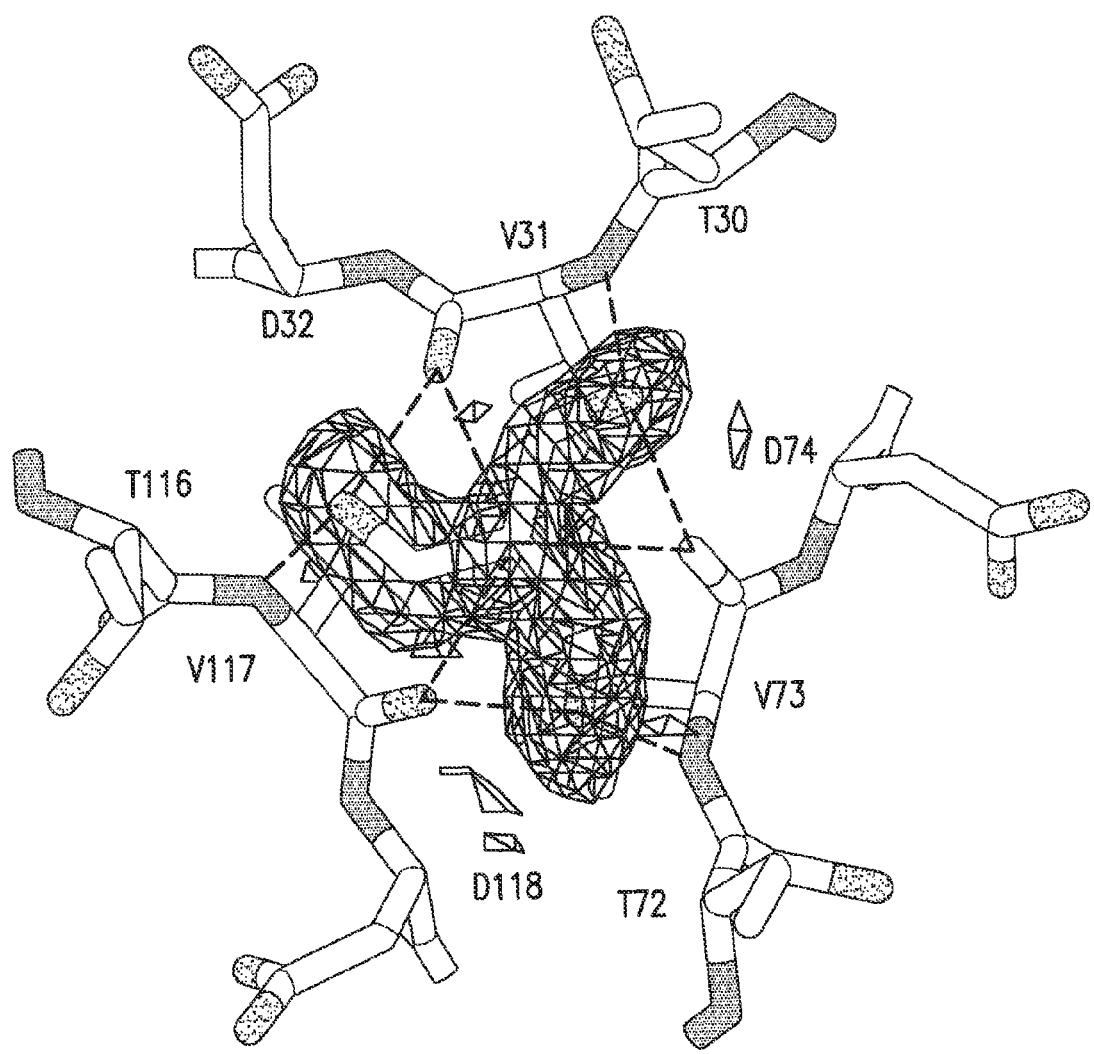

FIG. 6. Symfoil-1 mutant X-ray data omit-map contoured at 1.0σ and showing nonprotein density in the region of the threefold axis of structural symmetry at the base of the central β-barrel. A Tris molecule modeled into this density is shown, along with the H-bond interactions between the Tris polar groups and Symfoil-1 protein.

Figure 7:
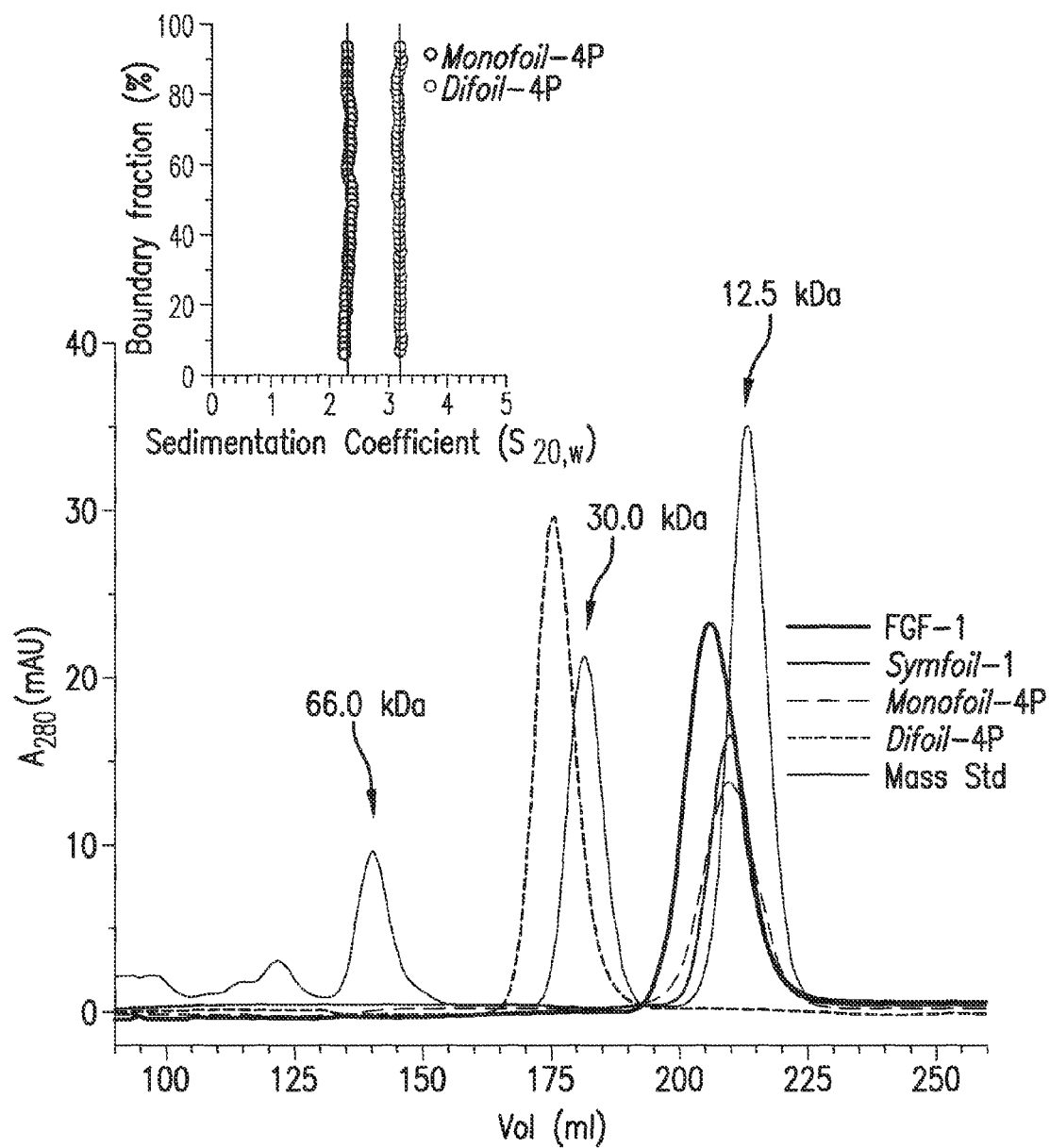

FIG. 7. Calibrated size-exclusion chromatography of FGF-1, Symfoil-1, Monofoil-4P, and Difoil-4P proteins. The Monofoil-4P polypeptide retention time is equivalent to that of the Symfoil-1 protein, indicating homotrimer assembly in solution. The Difoil-4P polypeptide retention time is approximately 36 kDa, also indicating homotrimer assembly in solution. The inset diagram shows the analytical ultracentrifuge sedimentation coefficients determined for the Monofoil-4P and Difoil-4P proteins and indicates homogeneous trimer assemblies for both polypeptides, with no evidence for monomeric or other multimeric assemblies.

FIG. 8A, FIG. 8B and FIG. 8C are tables showing SD transform #1: introduction of a symmetric constraint on the hydrophobic core region of FGF-1. Gray shading indicates positions related by 3-fold structural symmetry where either two or all three residues are identical. Boxed positions indicate the specific site(s) of mutation in construction of that particular mutant. ΔΔG values are a measure of the stability effect (referencing FGF-1 and determined in ADA buffer), where a negative value indicates an increase in overall thermostability. Thermodynamic data for FGF-1 are from Blaber, S. I. et al. (1999). Biophys. J. 77, 470-477 data for SYM2-SYM6 are from Brych, S. R. et al. (2001). Protein Sci. 10, 2587-2599 and Brych, S. R. et al. (2003) Protein Sci. 12, 2704-2718 data for SYM6ΔΔ are from Brych, S. R. et al. (2004). J. Mol. Biol. 344, 769-780 and ΔΔG data (determined in crystallization buffer) for SYM7ΔΔ and SYM8ΔΔ are from Dubey, V. K. et al. (2005). Protein Sci. 14, 2315-2323. FIGS. 8A-8C disclose SEQ ID NOS: 6-14, respectively, in order of appearance.

Figure 9:
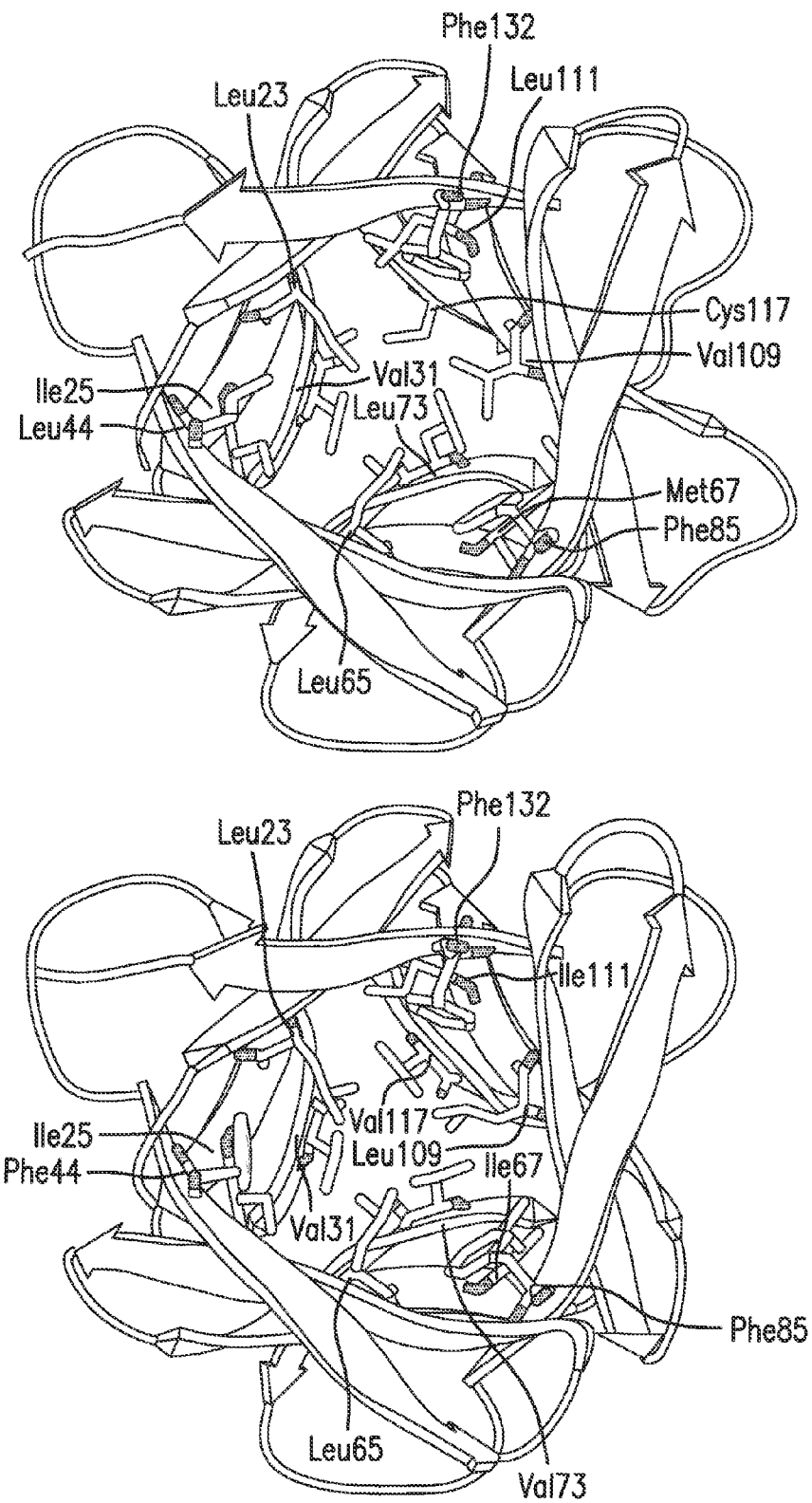

FIG. 9. Top: ribbon representation of the FGF-1 structure (2AFG) showing the residues that make up the central hydrophobic core. Bottom: similar ribbon representation of the SYM6ΔΔ(F108Y) mutant structure showing the equivalent hydrophobic core residues and illustrating the essential completion of transform #1 in the SD.

FIG. 10. SD transform #2: introduction of a symmetric constraint on reverse turn regions. Gray shading indicates positions related by 3-fold structural symmetry where either two or all three residues are identical. Boxed positions indicate the specific site(s) of mutation in construction of that particular mutant. ΔΔG values are a measure of the stability effect (referencing FGF-1), where a negative value indicates an increase in overall thermostability. Thermodynamic data are from Lee, J. & Blaber, M. (2011). Proc. Natl Acad. Sci. USA, 108, 126-130. FIG. 10 discloses SEQ ID NOS: 15-18, respectively, in order of appearance.

FIG. 11. SD transform #3: introduction of a symmetric constraint on β-strand regions. Gray shading indicates positions related by 3-fold structural symmetry where either two or all three residues are identical. Boxed positions indicate the specific site(s) of mutation in construction of that particular mutant. Underlined positions indicate the regions of the SYM13ΔΔ mutant utilized in the chimera construct of the Symfoil-1 mutant. ΔΔG values are a measure of the stability effect (referencing FGF-1), where a negative value indicates an increase in overall thermostability. Thermodynamic data are from Lee, J. & Blaber, M. (2011). Proc. Natl Acad. Sci. USA, 108, 126-130. FIG. 11 discloses SEQ ID NOS: 19-22, respectively, in order of appearance.

Figure 12:
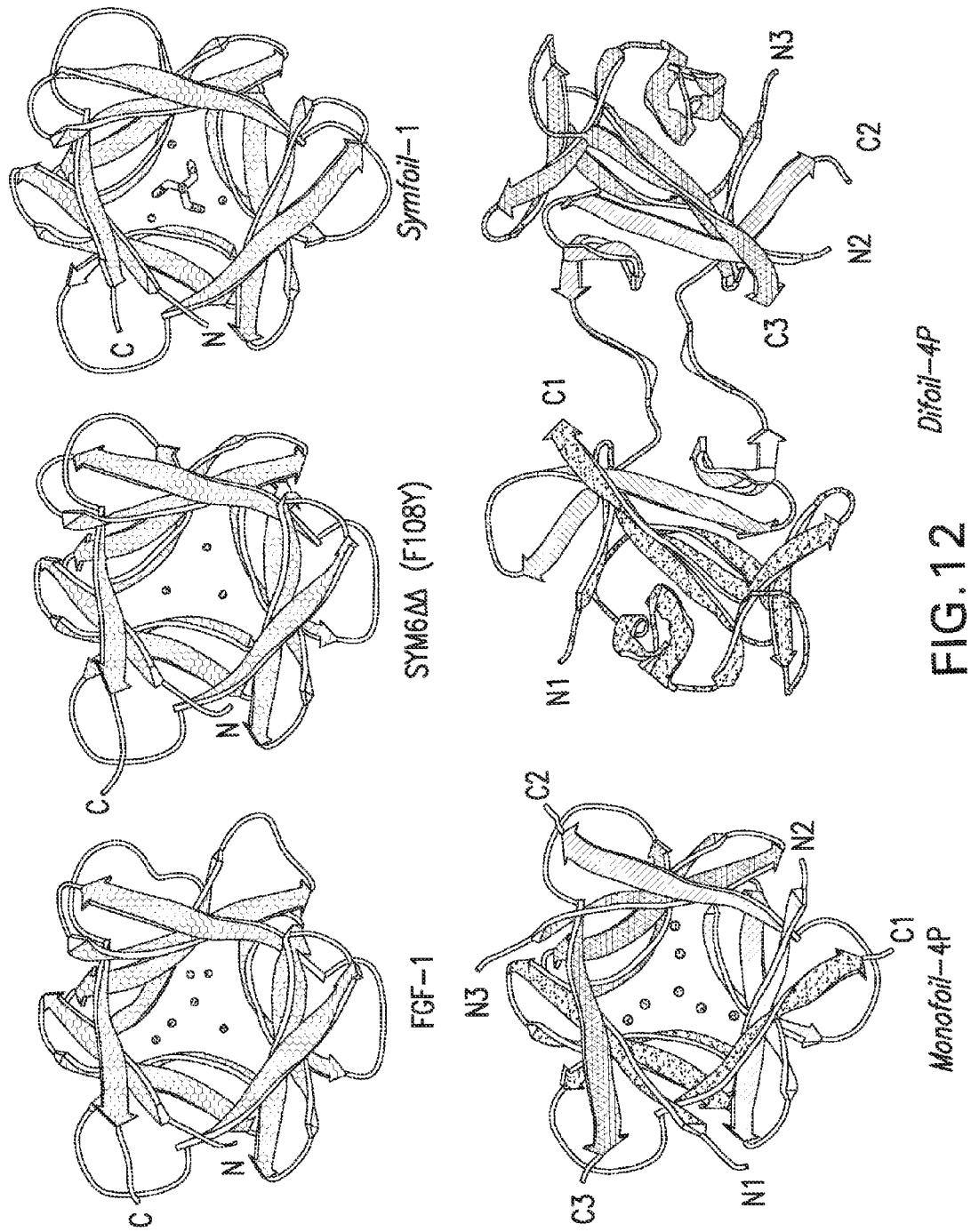

FIG. 12. Ribbon diagram of the X-ray structures of FGF-1 (Blaber, M. et al. (1996). Biochemistry, 35, 2086-2094) SYM6ΔΔ(Phe108Tyr), Symfoil-1, Monofoil-4P, and Difoil-4P proteins.21 FGF-1, SYM6ΔΔ(Phe108Tyr) and Symfoil-1 structures are colored according to their secondary structure (β-strands are yellow, turns/coils are gray). The Monofoil-4P and Difoil-4P structures are colored according to the individual polypeptide chains (chain A, red; chain B, green; chain C, blue). In each case except Difoil-4P, the view is down the 3-fold axis of structural symmetry. Select solvent structure at the bottom of the β-barrel in the vicinity of the 3-fold axis is shown; additionally, the Symfoil series of proteins crystallized in the presence of Tris buffer that bound at this 3-fold axis (shown in stick figure in the Symfoil-1 structure).

FIGS. 13A and 13B are tables showing SD transform #4: stability optimization and symmetric fragmentation. Gray shading indicates positions related by 3-fold structural symmetry where either two or all three residues are identical. Boxed positions indicate the specific site(s) of mutation in construction of that particular mutant. ΔΔG values are a measure of the stability effect (referencing FGF-1), where a negative value indicates an increase in overall thermostability. Thermodynamic data are from Lee, J. & Blaber, M. (2011). Proc. Natl Acad. Sci. USA, 108, 126-130. FIGS. 13A-13B disclose SEQ ID NOS: 23-28, respectively, in order of appearance.

Figure 14:
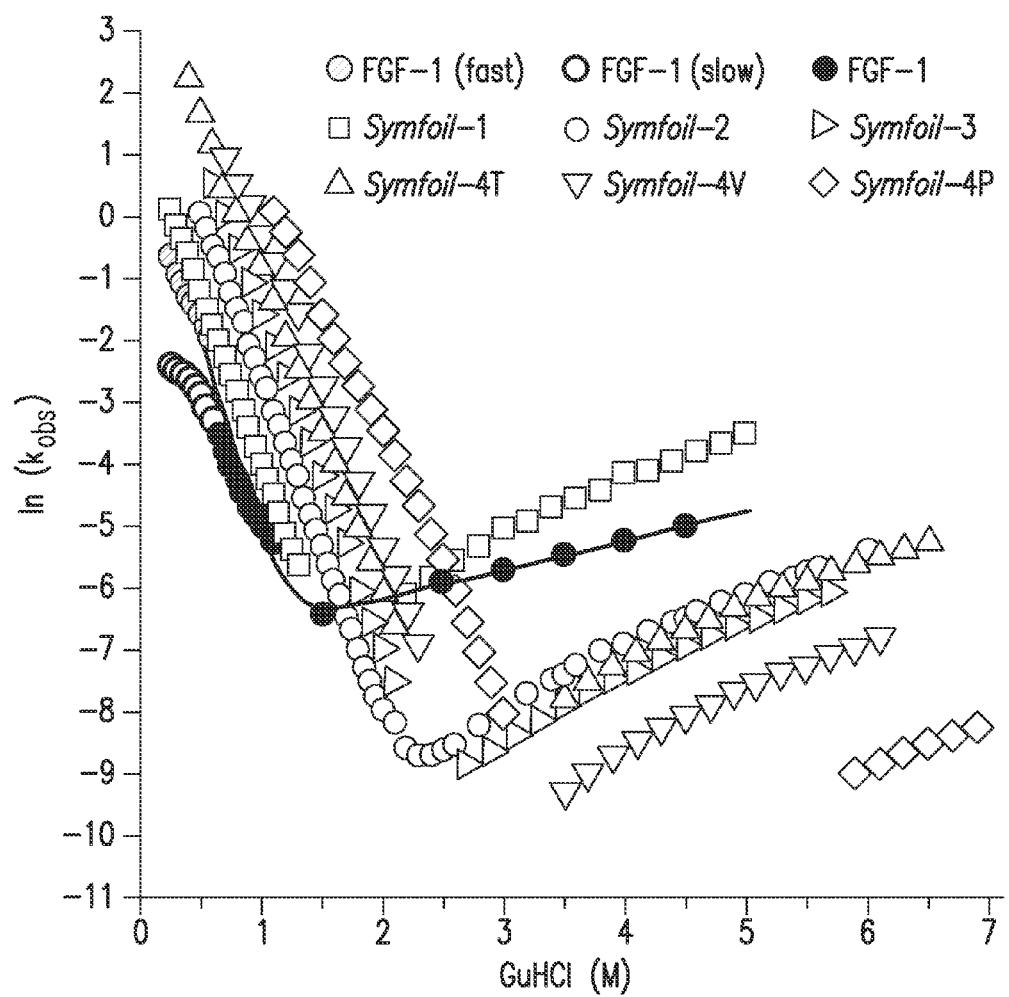

FIG. 14. Folding and unfolding kinetics for FGF-1 and Symfoil mutant proteins. The left-hand side of the figure shows the "folding arms" and the right-hand side shows the "unfolding arms." To facilitate identification of the FGF-1 folding profile, a line representing the global fitted function (i.e., "chevron plot") is shown. FGF-1 exhibits both a fast and a slow folding phase, whereas none of the Symfoil proteins exhibit this property. Stability optimization of the Symfoil series of proteins was associated with an increase in the folding kinetics but an even more pronounced decrease in the unfolding kinetics.

Figure 15:
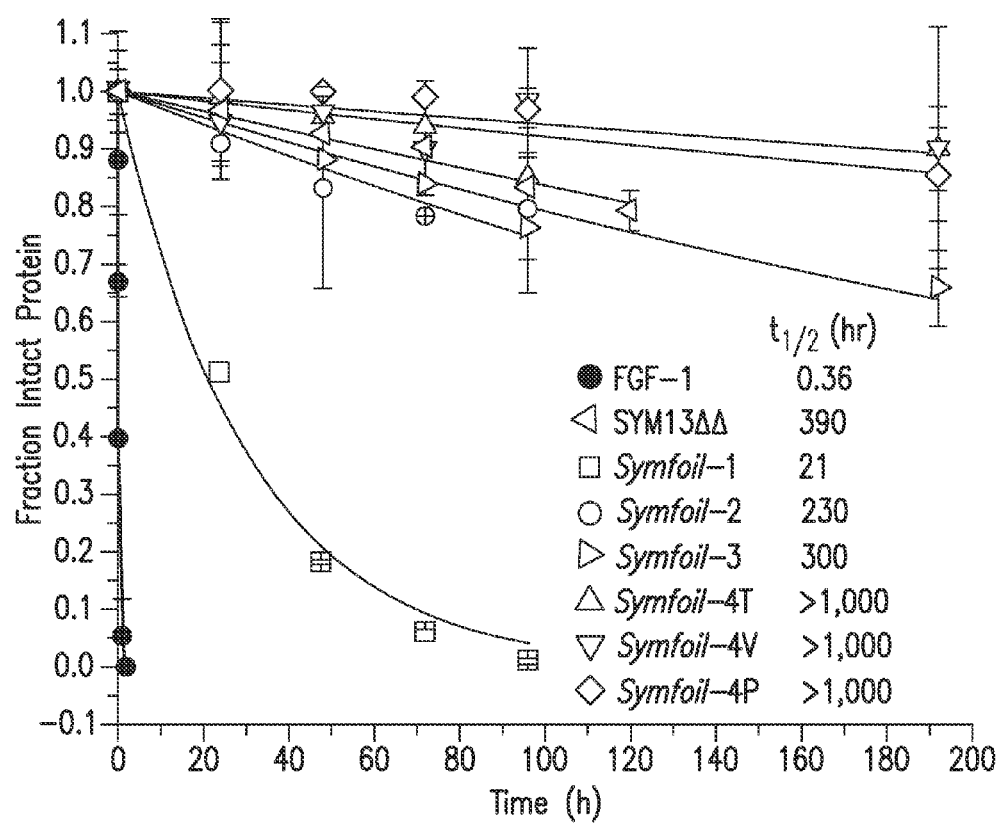

FIG. 15. Trypsin proteolysis of FGF-1, SYM13ΔΔ, and Symfoil mutant proteins. Resistance to proteolysis generally correlates with thermostability. The proteolytic degradation half-life of the optimized Symfoil protein (i.e., Symfoil-4P) is 3-4 orders of magnitude greater than that of the FGF-1 protein.

Figure 16:
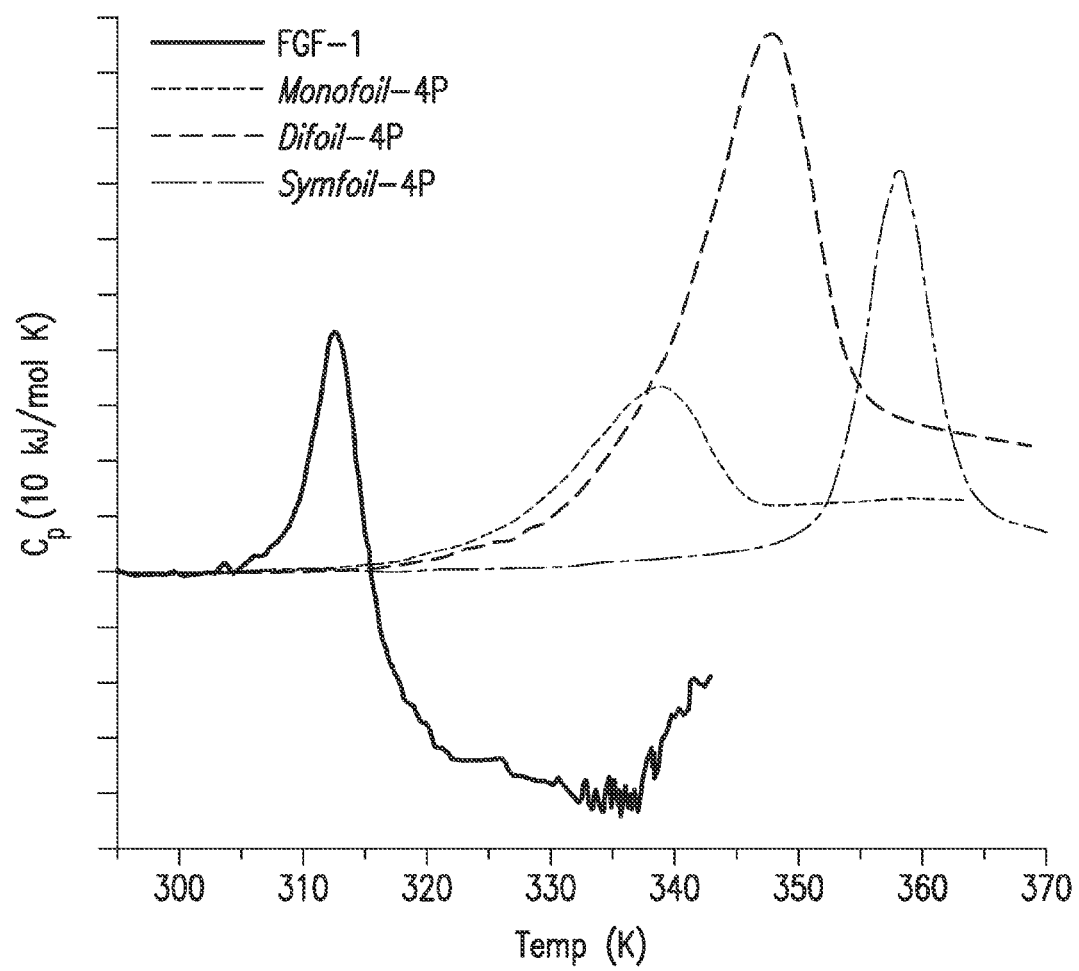

FIG. 16. DSC endotherms for FGF-1, Monofoil-4P, Difoil-4P, and Symfoil-4P polypeptides in ADA buffer. Endotherms for Monofoil-4P and Difoil-4P proteins are normalized per molar concentration of trimer assembly. FGF-1 has mesophilic stability and irreversibly aggregates during thermal denaturation, giving rise to the noisy exothermic signal post denaturation; Monofoil-4P, Difoil-4P, and Symfoil-4P proteins do not exhibit this property. The Symfoil-4P protein exhibits hyperthermophilic stability (i.e., Tm≤85° C.).

Figure 17:
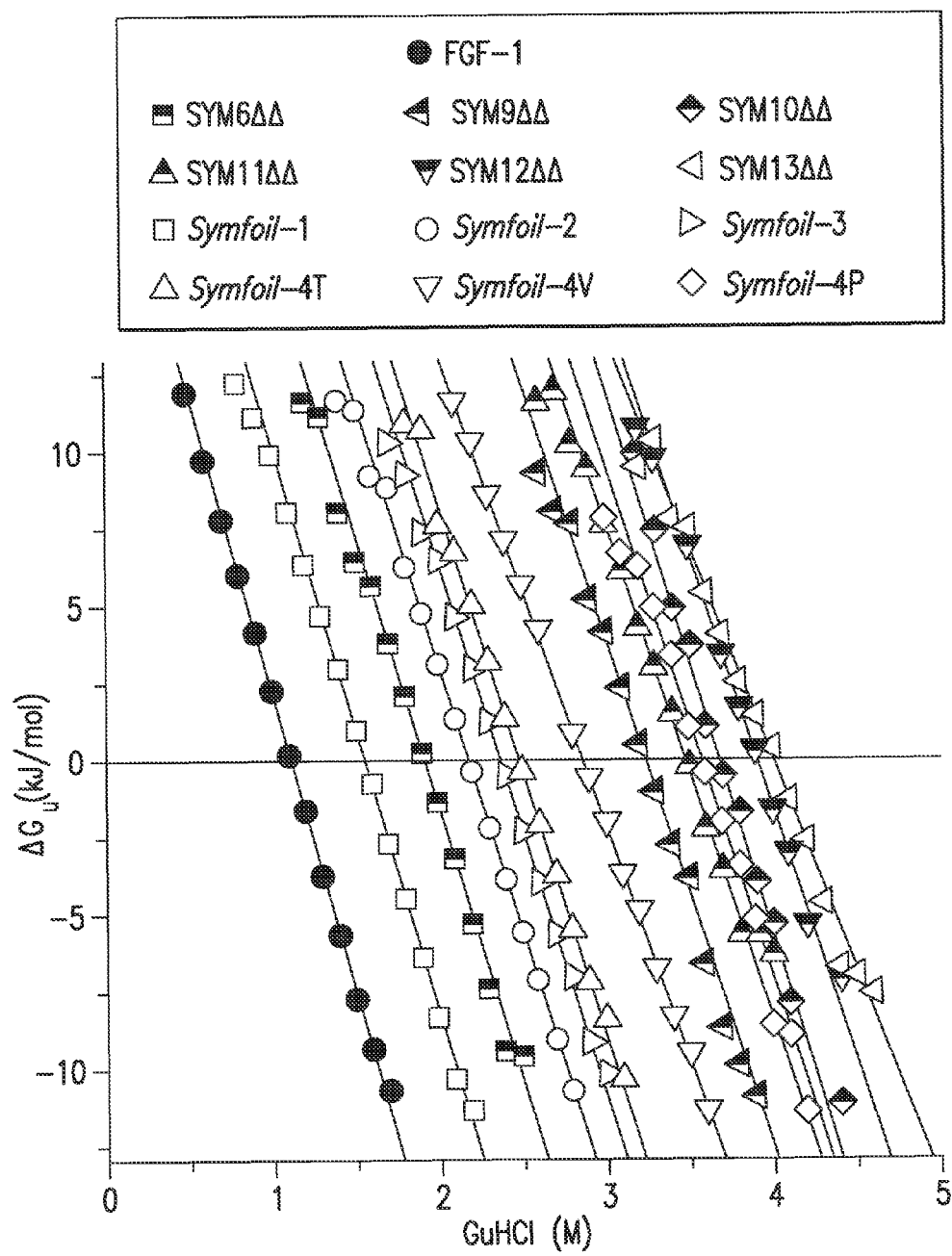

FIG. 17. ΔGu versus GuHCl denaturant concentration, as determined from isothermal equilibrium denaturation, for select mutants in the SD. Data shown are overlaid with the associated fitted function from a two-state model.

Figure 18:
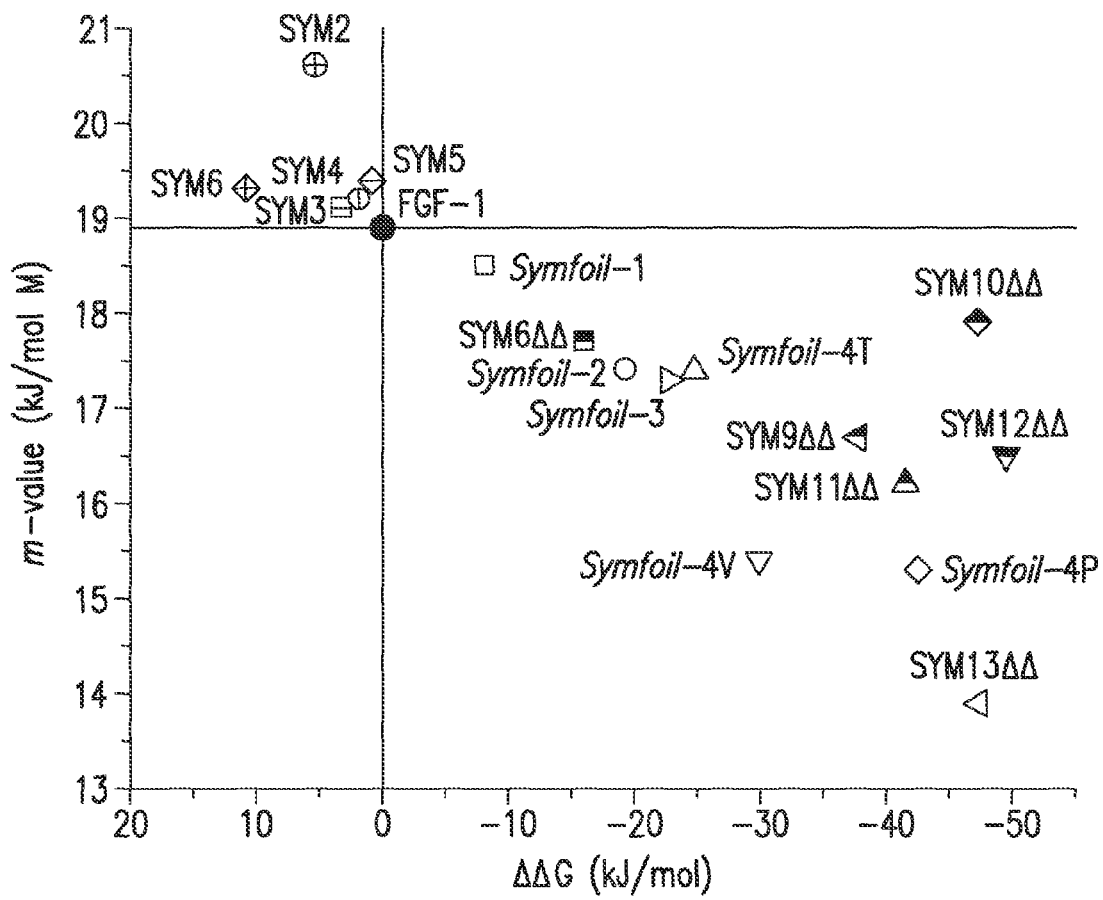

FIG. 18. Effects on change in protein stability (ΔΔG) plotted versus folding cooperativity m value for mutants in the SD (from isothermal equilibrium denaturation data). A negative value of ΔΔG indicates increased stability; an increase in m value indicates increased folding cooperativity. Increasing thermostability appears to correlate with a decline in folding cooperativity m value.

DETAILED DESCRIPTION OF THE INVENTION

The top-down symmetric deconstruction (SD) describes a logical approach that is broadly applicable and is not architecture dependent. What is described in this specification is the sequential targeting of core (transform #1), turn (transform #2), and, finally, secondary-structure (β-strand; transform #3) positions. This logic is, in principle, applicable in the SD of any aqueously soluble symmetric globular protein. Although the β-trefoil contains β-strand secondary structure and no α-helix, it is a straightforward modification of transform #3 to focus instead on α-helix. Each transform was developed by utilizing statistical preferences of amino acids, either conserved residues for the particular architecture (i.e., β-trefoil; transform #1) or conserved residues for the secondary structure (i.e., Asx-Pro-Asx-Gly in β-turns in transform #2 or preferred β-strand residues in transform #3). As with the conceptually related method of retrosynthetic analysis (RA) in the design of organic synthesis strategies (Corey, E. J. & Cheng, X. M. (1989). The Logic of Chemical Synthesis. John Wiley & Sons, Inc., New York), SD of protein architecture follows a specific logic even though the end point is not known a priori; this is the strength of the method, which can provide a useful alternative to bottom-up approaches to de novo protein design.

The present invention relates to a top-down symmetric deconstruction method for generating a polypeptide building block for design of a target architecture which may comprise: (a) choosing a protein having the target architecture, (b) imposing a cumulative symmetric constraint on core, turn and secondary structure by targeted mutagenesis, (c) retaining symmetric mutations if they are neutral or favorable to protein stability, folding and solubility, (d) analyzing sequences to identify candidate symmetric mutations, (e) analyzing the candidate symmetric mutations by molecular modeling, (f) determining a peptide sequence with a complete symmetric deconstruction and (g) fragmentation of the peptide sequence to determine the polypeptide building block, wherein polypeptide building block is generated for design of the target architecture.

In one embodiment, the target architecture may be a β-trefoil. Proteins containing the structural β-trefoil domain represent a diverse group of proteins, see, e.g., C. A. Orengo et al., Protein Superfamilies and Domain Superfolds, 372 Nature 631-634 (1994). The β-trefoil domain comprises a six-stranded β-barrel closed off at one end by three β-hairpin structures that exhibits a characteristic pseudo-threefold axis symmetry. The monomeric structural unit of this three-fold symmetry is referred to as the β-trefoil fold that contains four β-sheets organized as a pair of antiparallel β-sheets. Dividing each of these β-trefoil folds is a β-hairpin turn. Therefore, in a linear fashion, a β-trefoil domain comprises four β-sheets of the first β-trefoil fold (α-fold), a β-hairpin turn, four β-sheets of the second β-trefoil fold (β-fold), a second β-hairpin turn four β-sheets of the third β-trefoil fold (γ-fold). Because the first hairpin turn is located between the fourth and fifth β-sheets of the β-trefoil domain, it is designated the β4/β5 β-hairpin turn. Likewise, since the second hairpin turn is located between the eighth and ninth β-sheets of the β-trefoil domain, it is designated the β8/β9 β-hairpin turn.

Continuing research has elucidated that β4/β5 and β8/β9 β-hairpin turns are important in conferring the proper pseudo-threefold axis symmetry observed in the β-trefoil domain. Amino acid changes in these two β-hairpin turns can increase the stability of the β-trefoil domain, which in turn results in increased binding activity, see, e.g., Stephen R. Brych et al., Structure and Stability Effects of Mutations Designed to Increase the Primary Sequence Symmetry Within the Core Region of a β-trefoil, 10 Protein Sci. 2587-2599 (2001); Jaewon Kim et al., Alternative Type I and I' Turn Conformations in the β8/β9 β-hairpin of Human Acidic Fibroblast Growth Factor, 11 Protein Sci. 459-466 (2002); Jaewon Kim et al., Sequence swapping Does Not Result in Conformation Swapping for the β4/β5 and β8/β9 β-hairpin Turns in Human Acidic Fibroblast Growth Factor, 14 Protein Sci. 351-359 (2005). As a non-limiting example, replacement of an amino acid comprising either the β4/β5 hairpin turn or β8/β9 β-hairpin turn with a glycine results in increased stabilization of the β-trefoil domain. Therefore, replacement of amino acids located in the β4/β5 and β8/β9 β-hairpin turns of the β-trefoil domains present in the binding domain of Clostridial toxins will increase binding activity of such a modified Clostridial toxin by increasing the structural stability of the β-trefoil domain.

The β-trefoil proteins have little sequence similarity (sometimes less than 17%) and bind a range of molecules, including other proteins, DNA, membranes and carbohydrates. Members of the β-trefoil structural family include but are not limited to the following: IL-1-α and IL-1-β; members of the fibroblast growth factor (FGF) family including, e.g., acidic FGF and basic FGF, int-2, hst/KS3, FGF-5, FGF-6, and keratinocyte growth factor (Zhang et al., Proc. Natl. Acad. Sci. U.S.A. 88:3446-3450, 1991; Zhu et al., Science 251:90-93, 1991); hisactophilin (Habazettl et al., Nature 359:855-857, 1992); and soybean trypsin inhibitor (Wolfson et al., Biochemistry 32:5327-5331, 1993). See also McDonald and Hendrickson, Cell 73:421-424, 1993. The methods of the present invention encompasses top-down symmetric deconstruction method for generating a polypeptide building block for design of any β-trefoil protein such as, but not limited to, IL-1-α and IL-1-β; members of the fibroblast growth factor (FGF) family including, e.g., acidic FGF and basic FGF, int-2, hst/KS3, FGF-5, FGF-6, and keratinocyte growth factor, hisactophilin and soybean trypsin inhibitor.

In another embodiment, the protein may be fibroblast growth factor-1 (FGF-1). Fibroblast growth factor-1, a member of the 3-fold symmetric β-trefoil fold, was subjected to a series of symmetric constraint mutations in a process termed "top-down symmetric deconstruction." The mutations enforced a cumulative exact 3-fold symmetry upon symmetrically equivalent positions within the protein and were combined with a stability screen. This process culminated in a β-trefoil protein with exact 3-fold primary-structure symmetry that exhibited excellent folding and stability properties. Subsequent fragmentation of the repeating primary-structure motif yielded a 42-residue polypeptide capable of spontaneous assembly as a homotrimer, producing a thermostable β-trefoil architecture. The results show that despite pronounced reduction in sequence complexity, pure symmetry in the design of a foldable, thermostable β-trefoil fold is possible. The top-down symmetric deconstruction approach provides a novel alternative means to successfully identify a useful polypeptide "building block" for subsequent "bottom-up" de novo design of target protein architecture.

The Monofoil-4P polypeptide is a useful building block for traditional bottom-up hierarchical de novo design; it can assemble as a homotrimer or as a concatenated threefold repeat within a single polypeptide to spontaneously generate a soluble, foldable, thermostable, precisely defined β-trefoil fold. The resulting β-trefoil is functionally benign (i.e., no known FGF-1 function has carried over into the Monofoil-4P polypeptide) yet is thermostable and therefore function competent. Introduction of novel function can proceed via directed or random mutagenesis coupled with a functional selection or screen. In this regard, mutating the Monofoil-4P polypeptide could be utilized to search for 3-fold symmetric compatible function, whereas mutation of the Symfoil-4P polypeptide could explore function enabled by the introduction of asymmetry within the symmetric architecture. Preliminary studies with mix and match of the Monofoil-4P and Difoil-4P polypeptides have shown that heterodimers with 1:1 stoichiometry readily form, recapitulating an intact β-trefoil fold. In this regard, the Difoil-4P polypeptide could serve as a scaffold into which mutant Monofoil-4P type peptides could assemble to create intact soluble β-trefoil proteins with novel functionality.

The polypeptides elucidated by the present invention may be useful for either de novo design, rational design or directed evolution of novel proteins. Advantageously, such novel proteins may be based upon the β-trefoil architecture. The polypeptides of the present invention likely bind a range of molecules, including other proteins, DNA, membranes and carbohydrates. Therefore, the polypeptides of the present invention may be useful for developing therapeutics that target specific proteins, DNA, membranes and carbohydrates.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The present invention also encompasses of introducing a novel function into the polypeptides of the present invention. For example, the novel function may proceed via directed or random mutagenesis coupled with a functional selection or screen. Methods of mutagenesis are well known to one of skill in the art.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use.

As regards codon optimization, the nucleic acid molecules of the invention have a nucleotide sequence that encodes the antigens of the invention and can be designed to employ codons that are used in the genes of the subject in which the antigen is to be produced. In a preferred embodiment, the codons used are "humanized" codons, i.e., the codons are those that appear frequently in highly expressed human genes (Andre et al., J. Virol. 72:1497-1503, 1998).

Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or equivalent variants and derivatives of the polypeptides of the invention and functionally equivalent fragments thereof. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and polypeptides of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the polypeptides of the present invention may be used in accordance with the present invention. In certain embodiments, the polypeptides of the present invention may be used in vitro (such as using cell-free expression systems) and/or in cultured cells grown in vitro in order to produce the polypeptides which may then be used for various applications such as in the production of proteinaceous vaccines. For such applications, any vector that allows expression of the polypeptides in vitro and/or in cultured cells may be used.

For applications where it is desired that the polypeptides be expressed in vivo, for example when the transgenes of the invention are used in DNA or DNA-containing vaccines, any vector that allows for the expression of the polypeptides of the present invention and is safe for use in vivo may be used. In preferred embodiments the vectors used are safe for use in humans, mammals and/or laboratory animals.

For the polypeptides of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antigens and/or antibodies of the invention can be expressed.

For example, when the aim is to express the polypeptides of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the polypeptides under the identified circumstances. Polypeptides identified by the SD method, useful for de novo protein design, can also be produced by chemical synthesis methods (such as solid phase peptide synthesis, and other methods known to those skilled in the art).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Experimental Support for the Evolution of Symmetric Protein Architecture from a Simple Peptide Motif The majority of protein architectures exhibit elements of structural symmetry, and "gene duplication and fusion" is the evolutionary mechanism generally hypothesized to be responsible for their emergence from simple peptide motifs. Despite the central importance of the gene duplication and fusion hypothesis, experimental support for a plausible evolutionary pathway for a specific protein architecture has yet to be effectively demonstrated. To address this question, a unique "top-down symmetric deconstruction" strategy was utilized to successfully identify a simple peptide motif capable of recapitulating, via gene duplication and fusion processes, a symmetric protein architecture (the threefold symmetric β-trefoil fold). The folding properties of intermediary forms in this deconstruction agree precisely with a previously proposed "conserved architecture" model for symmetric protein evolution. Furthermore, a route through foldable sequence-space between the simple peptide motif and extant protein fold is demonstrated. These results provide compelling experimental support for a plausible evolutionary pathway of symmetric protein architecture via gene duplication and fusion processes.

Figure 1A:
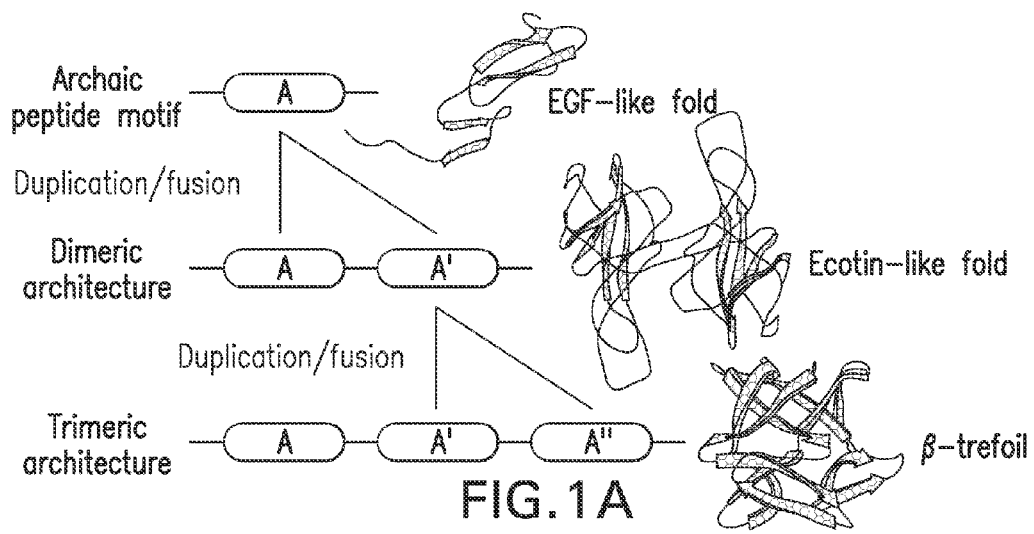
Figure 1B:
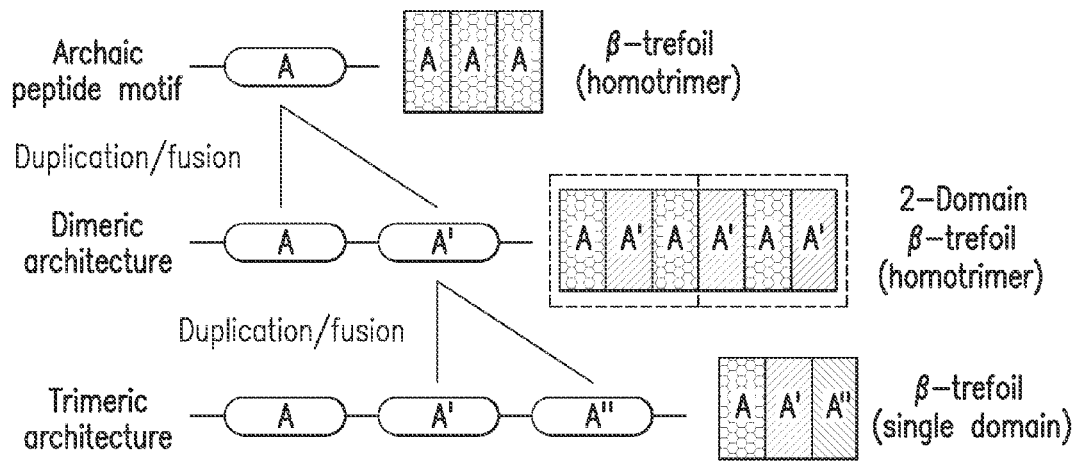

Symmetry is a central theme in protein structure, function, and evolution. Structural symmetry is observed in many different protein architectures, and gene duplication and fusion is the generally hypothesized mechanism for the emergence of symmetric architecture from simpler (i.e., archaic) peptide motifs (Sepulveda P et al. (1975) J Biol Chem 250:5082-5088, Tang et al. (1978) Nature 271:618-621, McLachlan A D (1979) J Mol Biol 133:557-563 and Inana G et al. (1983) Nature 302:310-315.). Such motifs, believed to represent the translational product of "genes of primordial life" (Tateno Y, et al. (1997) J Mol Evol 44:S38-S43), typically code for polypeptides of ~40-60 residues in length (Tateno Y, et al. (1997) J Mol Evol 44:S38-S43 and Dorit R L et al. (1990) Science 250:1377-1382) and may define elemental folding units (i.e., "foldons") (Panchenko A R et al. (1997) J Biol Chem 272:95-105). Two distinctly different evolutionary models for the emergence of symmetric protein architecture from a primordial peptide motif have been proposed (Mukhopadhyay D (2000) J Mol Evol 50:214-223, Ponting C P and Russell R B (2000) J Mol Biol 302:1041-1047, Liu L et al. (2002) FEBS Lett 528:114-118, Yadid I and Tawfik D S (2007) J Mol Biol 365:10-17, Akanuma S et al. (2010) J Biochem 147:371-379 and Richter M et al. (2010) J Mol Biol 398:763-773). In the "emergent architecture" model, the primordial peptide autonomously folds to yield a simple architecture and the complex symmetric architecture emerges upon a final gene duplication and fusion event (FIG. 1A). In the conserved architecture model, the symmetric architecture (or integral units thereof) is present at each step of the evolutionary process (FIG. 1B).

Experimental studies to probe the evolutionary pathway responsible for symmetric protein architecture have focused principally upon the behavior of subdomain fragments of extant symmetric proteins and have asked whether such fragments fold independently or oligomerize. A fragmentation study of the twofold symmetric aspartate racemase enzyme identified an independently folding monomeric subdomain, leading the inventors to propose an emergent-architecture-type evolutionary model (Liu L et al. (2002) FEBS Lett 528:114-118). Fragmentation studies of a fivefold symmetric "β-propeller" protein to identify an ancient folding motif showed evidence of multimeric assembly for ~100 amino acid fragments comprising two copies of the repeating motif, but not for ~50 amino acid single motif fragments (Yadid I and Tawfik D S (2007) J Mol Biol 365:10-17). Subsequent X-ray structure analysis showed that these duplicated fragments assembled to create two intact β-propeller pentamers, with each pentamer containing 2.5 dimeric domains (with one dimer spanning both pentamers) (Yadid I et al. (2010) Proc Natl Acad Sci USA 107:7287-7292), supporting a conserved-architecture-type model. In the $(\beta\alpha)_8$-barrel architecture, studies of $(\beta\alpha)_4$ half-domain fragments showed that these subdomains assembled to form an intact $(\beta\alpha)_8$-barrel but could also exist as independently folded subdomains (Hocker B et al. (2001) Nat Struct Biol 8:32-36 and Akanuma S and Yamagishi A (2008) J Mol Biol 382:458-466). Computational and experimental studies designed to identify a corresponding $(\beta\alpha)_2$ "building block" identified a peptide capable of tetrameric oligomerization to create an intact $(\beta\alpha)_8$-barrel but could also exist as an independently folded subdomain (Richter M et al. (2010) J Mol Biol 398:763-773), thus supporting both types of evolutionary models. However, such simple fragmentation studies of symmetric proteins have suspected limitations. Evolutionary divergence following a duplication/fusion event likely results in optimization of the unique interdomain interface, such that independent folding of fragments is unlikely; thus, solubility and folding properties of fragments of extant proteins are unlikely to recapitulate those of the archaic peptide motif (Yadid I and Tawfik D S (2007) J Mol Biol 365:10-17).

Figures 2A, 2B:
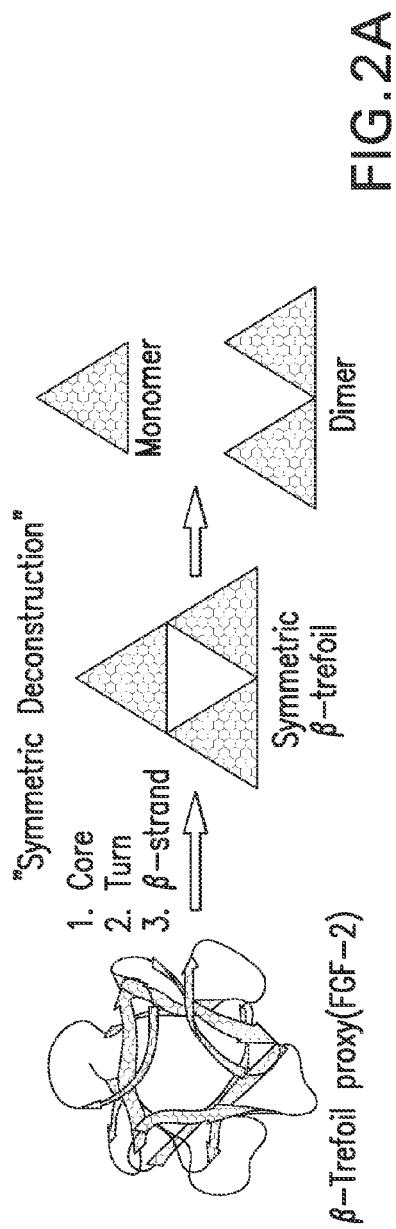
Figure 3A:
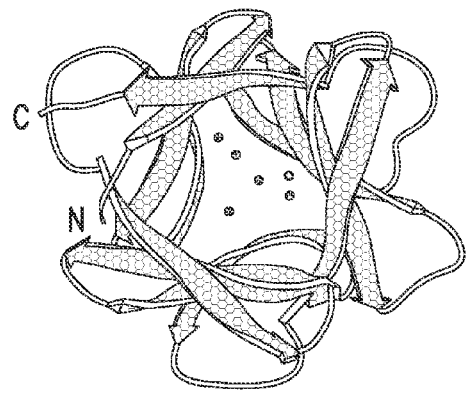
FIG. 3D is a ribbon diagram illustrating X-ray structure of Monofoil-4P protein with select solvent according to one embodiment of the present invention. The individual Monofoil-4P peptides are colored red, green, and blue and their respective N and C termini are indicated.
FIG. 3E is a ribbon diagram illustrating X-ray structure of the Difoil-4P protein (individual polypeptides colored as in FIG. 3D) and with respective N and C termini indicated according to one embodiment of the present invention. The view is down a twofold axis of symmetry relating the two intact β-trefoil folds present in the homotrimer Difoil-4P structure.
FIG. 3F is a ribbon diagram illustrating the X-ray structure of the Difoil-4P protein according to one embodiment of the present invention. The X-ray structure of the Difoil-4P shown in FIG. 3E is rotated to view down the threefold axis of symmetry within the first β-trefoil domain and overlaid with the Symfoil-4P structure (gray).
FIG. 3G is a secondary structure schematic diagram of Difoil-4P (colored as in FIG. 3E). The boxed regions indicate the two β-trefoil domains.

In this Example, Applicants describe an experimental top-down symmetric deconstruction of symmetric protein architecture (the β-trefoil fold) with the goal of testing two competing hypotheses for its evolution from an archaic peptide motif. The starting point for this deconstruction is human fibroblast growth factor-1 (FGF-1), a 140 amino acid single-domain globular protein exhibiting the characteristic threefold symmetry of the β-trefoil architecture (where each ~45 amino acid repeating subdomain is termed a trefoil-fold; Murzin A G et al. (1992) J Mol Biol 223:531-543). As is commonly observed with symmetric proteins, the discernible tertiary structure symmetry of FGF-1 is substantially imperfect at both the primary and tertiary structure levels (FIGS. 2B and 3A). The symmetric deconstruction involved sequential introduction of symmetric mutations (targeting core, reverse-turn, and β-strand secondary structure, respectively) until a purely threefold symmetric primary structure solution was achieved. This symmetric primary structure defines a repeating trefoil-fold polypeptide motif, whose folding and structural properties were studied along with dimer and monomer peptide fragments. The structure and folding properties for these polypeptides agree precisely with a previously hypothesized conserved architecture model of evolution; furthermore, each intermediate mutant in the symmetric deconstruction resides within foldable sequence space, providing thermodynamic support for the hypothesized evolutionary pathway.

Top-Down Symmetric Deconstruction.

A total of 18 mutant proteins were constructed and characterized in the process of successfully introducing a complete threefold symmetric primary structure constraint (involving 76 substitutions and 4 deleted positions total; FIGS. 2A and 2B, and Table 1). Detailed biophysical properties for each of these mutants, as well as details of unsuccessful mutations (principally resulting in poor folding cooperativity, solubility, or thermostability) are presented in Example 3. The initial symmetric protein produced by the deconstruction is termed "Symfoil-1" (for symmetric β-trefoil protein 1). The Symfoil-1 protein has several notable properties in comparison to FGF-1. Symfoil-1 is more thermostable than FGF-1, and whereas FGF-1 irreversibly aggregates upon thermal denaturation, Symfoil-1 exhibits reversible two-state unfolding (FIG. 5A and FIG. 5B). FGF-1 contains examples of all 20 common amino acids, whereas Symfoil-1 is devoid of Trp, Ala, Cys, and Met residues. Additionally, Symfoil-1 has no known FGF-1 functional properties (including FGF receptor-binding, heparin-binding, nuclear localization signal, mitogenic activity, etc.). Symfoil-1 is able to bind the C3 symmetric molecule Tris on a threefold axis of structural symmetry (FIG. 6). The Symfoil-1 synthetic protein was subsequently optimized by mutation to yield a hyperthermophilic variant (Symfoil-4P mutant, Table 1). Monomeric and dimeric versions of the repeating peptide motif within Symfoil-4P were subsequently created by the introduction of stop codons at the appropriate locations, producing the Monofoil-4P (for monomer trefoil fold) and Difoil-4P (for dimer trefoil fold) polypeptides, respectively (FIG. 2B).

Properties of the Monofoil-4P, Difoil-4P, and Symfoil-4P Polypeptides.

Figure 3B:
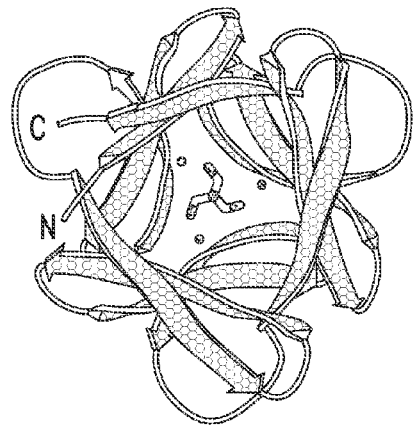
Figure 3C:
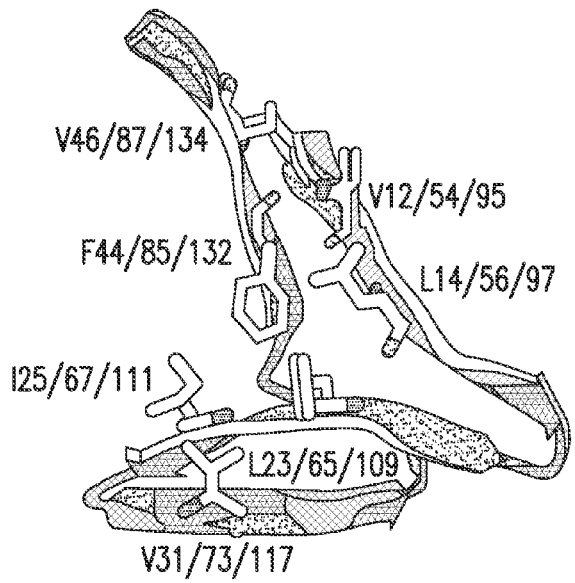

Both the Monofoil-4P and Difoil-4P polypeptides resolved as single peaks on calibrated size-exclusion chromatography, with apparent masses indicating a homotrimer (in both cases) and no detectable monomer (FIG. 7). Monofoil-4P and Difoil-4P proteins sedimented as homogeneous forms with $s_{20,w}$ values of 2.31±0.036 s and 3.18±0.021 s, respectively, and with corresponding molecular mass of 18.8 and 29.8 kDa, respectively. The molecular mass of the Monofoil-4P (6.6 kDa) and Difoil-4P (11.2 kDa) polypeptides therefore indicate homotrimer oligomerization for both polypeptides in solution. X-ray crystal structures were solved for Symfoil-1, 2, 4T, 4V, and 4P proteins as well as the Monofoil-4P and Difoil-4P polypeptides (FIGS. 3A-3G, and Table 2). The peptide backbone of the Symfoil-1 protein exhibits a striking threefold rotational symmetry that is similar to the structure of FGF-1 protein (FIG. 3A and FIG. 3B). The main-chain atoms of the three individual trefoil-fold subdomains of the Symfoil-1 protein overlay each other with an rms deviation of 0.2 Å, indicating essentially indistinguishable trefoil-fold subdomain structures.

Figure 3D:
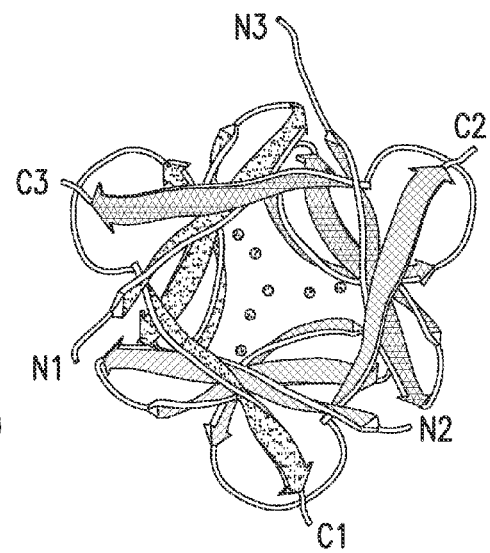
Figure 3E:
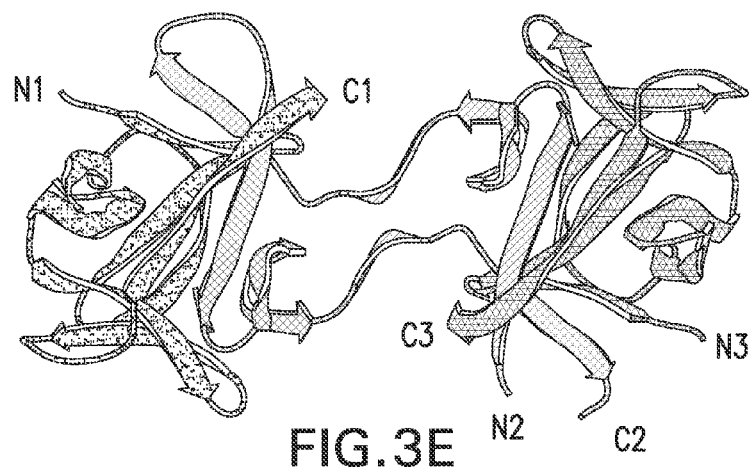
Figure 3F:
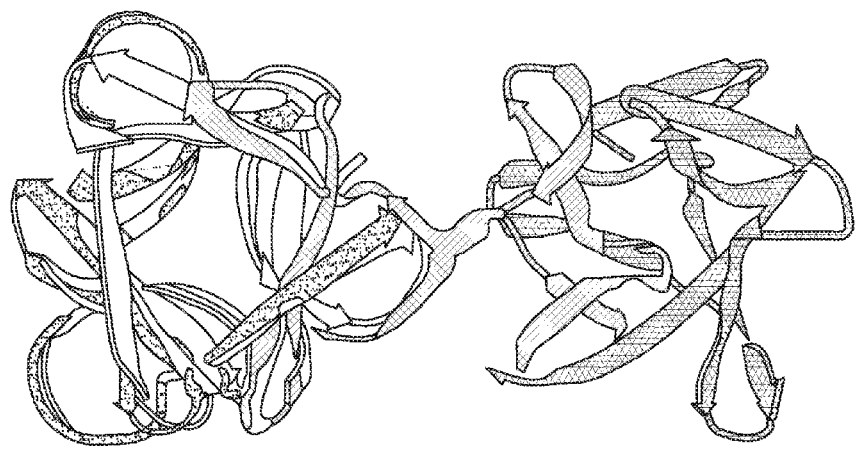
Figure 3G:
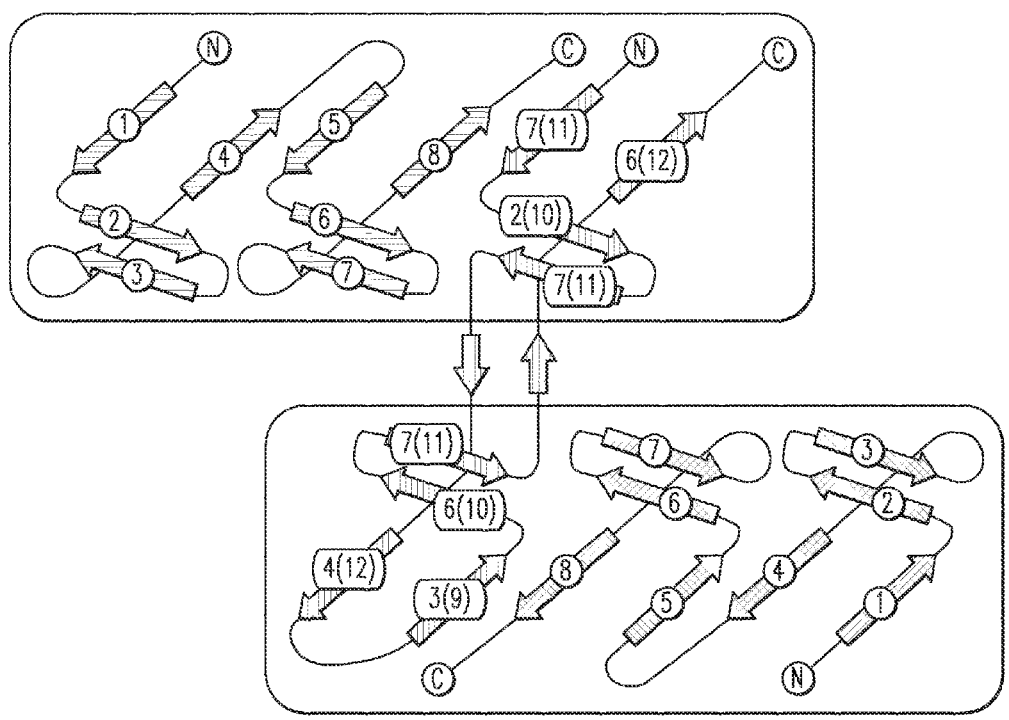

Furthermore, the side-chain rotamers for the set of core-packing residues (and essentially all surface residues with the exception of specific crystal contacts) are identical for a comparison of the three trefoil-fold subdomains (FIG. 3C); thus, the threefold symmetry of the Symfoil protein(s) appears exact. The Monofoil-4P structure exhibits a homotrimer assembly that recapitulates the intact β-trefoil architecture (FIG. 3D). An overlay of all main-chain atoms comprising the individual repeating trefoil-fold subdomains of the Monofoil-4P trimer with the Symfoil-4P structure yields an rms deviation of 0.5 Å, indicating essential structural identity. Similarly, analysis of side-chain rotamers indicates exact threefold symmetry in the Monofoil-4P structure. The Difoil-4P structure exhibits two intact β-trefoil folds related by a pseudo-twofold axis of symmetry and constructed from three polypeptide chains (FIG. 3E). Peptide chain B in this complex (colored green in FIG. 3E) adopts an entirely different conformation from the other two peptide chains. Despite this structural alteration, the main-chain atoms of the overall β-trefoil folds contained within the Difoil-4P homotrimer overlay those of the Symfoil-4P structure with an rmsd of ~0.7 Å, indicating a highly conserved β-trefoil architecture (FIG. 3F). The two β-trefoil folds in Difoil-4P are constructed from three polypeptide chains via a "domain swapped" architecture (FIG. 3G). The first β-trefoil is comprised of chain "A" plus β-strands 1, 2, 3, and 8 of chain "B," whereas the second β-trefoil is comprised of chain "C" plus β-strands 4, 5, 6, and 7 of chain B. In this second β-trefoil, contiguous β-strands 4 and 5 of chain B take the place of canonical β-strands 12 and 9, respectively (FIG. 3F).

Support for the Conserved Architecture Model of Symmetric Protein Evolution.

Competing emergent architecture and conserved architecture models have been proposed for the evolutionary pathway of the threefold symmetric β-trefoil architecture. In the emergent architecture model of Mukhopadhyay (Mukhopadhyay D (2000) J Mol Evol 50:214-223), the ancient peptide motif was hypothesized to have been an autonomously folding single-domain, small globular protein, with a simple epidermal growth-factor-like fold. Dimerization driven by mutation(s) causing "domain-swapping" was postulated to produce a C2 symmetric molecule with an overall Ecotin-like fold. The β-trefoil architecture was hypothesized to have emerged after a final duplication and fusion event. A distinctly different conserved architecture model for the evolution of β-trefoil architecture was proposed at essentially the same time by Ponting and Russell (Ponting C P et al. Russell R B (2000) J Mol Biol 302:1041-1047). In this model, the ancient peptide motif was hypothesized to have existed as a homotrimer with overall β-trefoil architecture. Duplication and fusion resulted in a dimer repeat of this polypeptide which also folded as a homotrimer, producing two complete β-trefoil folds (although structural details of exactly how this would be accomplished were not proposed). A subsequent duplication and fusion event produced a triplicate repeat of the trefoil-fold peptide, yielding a single polypeptide with β-trefoil architecture.

Figures 4A, 4B:
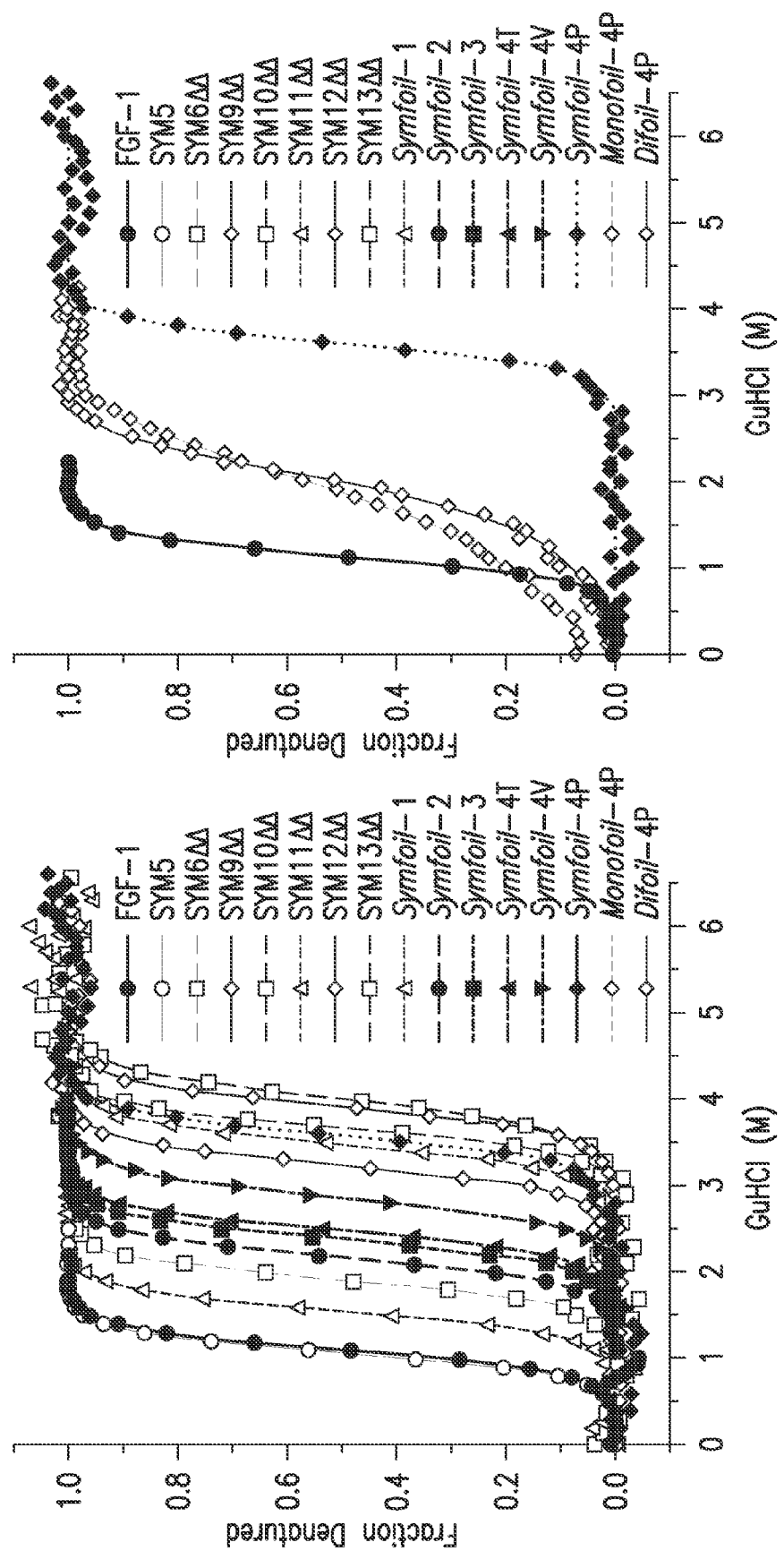
FIG. 4A is a graph illustrating isothermal equilibrium denaturation profiles for FGF-1 and all single-polypeptide mutant proteins comprising the top-down symmetric deconstruction (culminating in the Symfoil-4P mutant) according to one embodiment of the present invention. The starting FGF-1 protein is the least stable in comparison to all mutant proteins.
FIG. 4B is a graph illustrating isothermal equilibrium denaturation profiles comparing the homotrimer assemblies of Monofoil-4P and Difoil-4P peptides (10 μM each) with FGF-1 and Symfoil-4P proteins according to one embodiment of the present invention.

Symmetric deconstruction of the β-trefoil architecture was undertaken with no preconceived ideas regarding the sequence or properties of the ultimate polypeptide; however, the results show that the oligomerization and structural details of the Monofoil, Difoil, and Symfoil polypeptides agree precisely with the conserved architecture model of β-trefoil evolution (FIGS. 1B and 3). The symmetric deconstruction of the FGF-1 protein was accomplished in a punctuated stepwise manner with each of the 18 intermediate mutant forms being foldable, thermostable, and soluble (FIG. 4A, FIG. 4B and Table 3); thus, the results also present a thermodynamically tenable pathway, through foldable sequence space, extending from FGF-1 to the Monofoil-4P peptide. Sequence analysis suggests that all extant β-trefoil proteins evolved from a common ancestor (Ponting C P et al. Russell R B (2000) J Mol Biol 302:1041-1047), because no homotrimer examples of the β-trefoil architecture (either Monofoil-type or Difoil-type) have been reported, the experimentally supported evolutionarily model describes a likely primordial event. Whereas the emergent architecture model implies "simple gene-simple protein architecture," the supported conserved architecture model enables complex protein architecture (e.g., a β-trefoil fold) via a simple gene (i.e., coding for a Monofoil-like 42-mer peptide). Thus, the results also support the hypothesis that complex protein architecture is possible in ancient life forms containing a substantially reduced genome complexity.

Implications for de Novo Protein Design.

A long-standing goal in de novo protein design has been the exploitation of a "bottom-up" hierarchical design strategy utilizing peptide building blocks that can assemble (via oligomerization or concatenation) into target architecture (DeGrado W F et al. (1987) Cold Spring Harbor Symp Quant Biol 52:521-526, Regan L and DeGrado W F (1988) Science 241:976-978 and Richardson J and Richardson D C (1989) Trends Biochem Sci 14:304-309) (in effect, paralleling aspects of the evolutionary pathway). The top-down symmetric deconstruction approach was remarkably successful in identifying a peptide building block solution (i.e., Monofoil-4P peptide) for the β-trefoil architecture. Engineered thermostable protein architecture can serve as a "function-competent" (Soskine M and Tawfik D S (2010) Nat Rev Genet 11:572-582) scaffold for the incorporation of unique functionality (Gibney B R et al. (1997) Curr Opin Chem Biol 1:537-542 and Schafmeister C E and Stroud R M (1998) Curr Opin Biotechnol 9:350-353). Although the FGF-1 protein has low mesophilic stability (Blaber S I et al. (1999) Biophys J 77:470-477 and Copeland R A et al. (1991) Arch Biochem Biophys 289:53-61), inclusion of a stability screen in the deconstruction resulted in a hyperthermophilic β-trefoil (the Symfoil-4P protein), and may therefore be utilized as a departure point in bottom-up de novo protein design for the incorporation of unique functionality. The fundamental "symmetric deconstruction" concept is architecture independent and therefore applicable in identifying a peptide building block for other symmetric protein folds.

Top-Down Symmetric Deconstruction. Top-down symmetric deconstruction is the introduction (via mutagenesis) of a symmetric constraint upon the primary and tertiary structure of a naturally evolved symmetric protein fold with the goal of achieving a purely symmetric primary structure. Briefly, the deconstruction is accomplished via a series of cumulative symmetric mutagenic transforms. In the case of FGF-1, this deconstruction involved a cumulative symmetric constraint upon core, reverse-turn, and β-strand secondary structure elements, respectively (FIG. 2A). Symmetric deconstruction of FGF-1 requires substantial change to both the primary and tertiary structure of the protein (FIG. 2B). Mutations were combined with a screen for protein folding, stability, and solubility, and were retained if they were neutral or improved upon such properties. Maximum use was made of previously published data (26. Brych S R et al. (2001) Protein Sci 10:2587-2599, Brych S R et al. (2003) Protein Sci 12:2704-2718, Brych S R et al. (2004) J Mol Biol 344:769-780, Dubey V K et al. (2005) Protein Sci 14:2315-2323, Dubey V K et al. (2007) J Mol Biol 371:256-268, Kim J et al. (2003) J Mol Biol 328:951-961, Kim J et al. (2005) Protein Sci 14:351-359, Lee J and Blaber M (2009) J Mol Biol 393:128-139 and Lee J et al. (2008) J Mol Biol 377:1251-1264) as well as sequence analysis to identify useful symmetric mutations in FGF-1. A summary of the application of specific transforms in pursuing a symmetric deconstruction of FGF-1 follows.

Transform 1: Symmetric Deconstruction of the Hydrophobic Core.

Previously published work detailed the development of a series of symmetric core-packing mutations (SYM2-5, Brych S R et al. (2001) Protein Sci 10:2587-2599 and Brych S R et al. (2003) Protein Sci 12:2704-2718; see Table 1 for mutant definitions) in FGF-1 that systematically introduced a symmetric primary structure constraint. Achieving a purely symmetric core while avoiding substantial destabilization required deletion of six amino acids within the third trefoil-fold subdomain, producing the SYM6ΔΔ mutant (Brych S R et al. (2004) J Mol Biol 344:769-780). Subsequent development of the SYM7ΔΔ mutant (Dubey V K et al. (2005) Protein Sci 14:2315-2323), involving symmetric mutations in additional buried hydrophobic positions of the protein represented essential completion of transform 1 and was the starting point for the application of transform 2.

Transform 2: Symmetric deconstruction of reverse turns. The SYM7ΔΔ mutant was initially modified by the inclusion of two previously described stabilizing point mutations (Lys12Val and Pro134Val) (Dubey V K et al. (2007) J Mol Biol 371:256-268) to produce the SYM9ΔΔ mutant. These mutations are located in the adjacent first and last β-strands of the β-barrel of the architecture, respectively, and represent a "discontinuous" β-turn within the threefold architecture. A His93Gly mutation, located within β-turn 8 and known to stabilize FGF-1 (Kim J et al. (2003) J Mol Biol 328:951-961 and Arakawa T et al. (1993) Protein Eng 6:541-546), was introduced into the SYM9ΔΔ mutant to produce the SYM10ΔΔ mutant. Prior studies of the role of the statistically preferred β-turn motif Asx-Pro-Asx-Gly (SEQ ID NO: 1) at individual β-turns 2, 6, and 10 in FGF-1 indicated a consistently favorable effect upon thermostability with Asn-Xxx-Asp-Gly (where Xxx represents the retained FGF-1 residue at this position) (Lee J et al. (2008) J Mol Biol 377:1251-1264). The canonical Asn-Pro-Asp-Gly (SEQ ID NO: 2) sequence was therefore substituted into the SYM10ΔΔ mutant at each of these symmetry-related β-turns to produce the SYM11ΔΔ mutant. The symmetric deconstruction of β-turn regions was not taken to completion at this stage, and the SYM11ΔΔ mutant was considered a successful "proof-of-concept" and was utilized as the starting point for transform 3.

Transform 3: Symmetric Deconstruction of β-Strands.

An Asn95Val mutation was introduced into SYM11ΔΔ resulting in a symmetric (Val) deconstruction of positions 12, 54, and 95 within β-strands 1, 5, and 9, respectively. Similarly, Leu46Val and Glu87Val mutations were introduced, resulting in a further symmetric constraint within symmetry-related β-strands 4, 8, and 12, respectively. The combination of these mutations resulted in the SYM12ΔΔ mutant. Ile56Leu and Tyr97Leu mutations were introduced into the SYM12ΔΔ mutant, resulting in a symmetric constraint upon symmetry-related β-strand positions 14, 56, and 97 and producing the SYM13ΔΔ mutant. The symmetric deconstruction of β-strand secondary structure was not taken to completion at this stage, and the SYM13ΔΔ mutant was considered a successful proof-of-concept. Completion of transforms 2 and 3 was achieved simultaneously by a chimera construct strategy chosen to eliminate reactive free thiols at positions Cys16 and Cys83. The resulting chimera sequence, yielding a complete symmetric deconstruction, is termed Symfoil-1.

Transform 4: Fragmentation of the Repeating Motif.

Optimization of Symfoil-1 stability was pursued prior to fragmentation of the repeating motif. The optimization design involved development of the Symfoil-2, Symfoil-3, Symfoil-4T, 4V, and 4P mutants (Table 1). The Symfoil-4P mutant (the most stable Symfoil variant) was selected as the starting point for fragmentation studies of the repeating peptide motif. Monomer and dimer subdomains were constructed by mutagenesis to introduce stop codons at positions Glu53 or Glu94, respectively, of the Symfoil-4P construct (FIG. 2). The resulting monomeric and dimeric trefoil-fold peptides are referred to as Monofoil-4P and Difoil-4P, respectively (for monomerictrefoil fold and dimeric trefoil fold, respectively).

Mutagenesis, Protein Purification, and Characterization.

Mutagenesis and protein purification and details of structural and biophysical characterization of mutant proteins followed previously published methods and are provided in Example 2.

Example 2: Supporting Information for Experimental Support for the Evolution of Symmetric Protein Architecture from a Simple Peptide Motif Mutagenesis and Protein Purification. Construction of all the "SYMΔΔ" mutants utilized a synthetic gene for the 140 amino acid form of human fibroblast growth factor-1 (FGF-1) (Gimenez-Gallego et al. (1986) Biochem Biophys Res Commun 128:611-617, Linemeyer D L et al. (1990) Growth Factors 3:287-298, Ortega S et al. (1991) J Biol Chem. 266:5842-5846 and Blaber et al. (1996) Biochemistry 35:2086-2094) containing an additional amino-terminal six His tag (SEQ ID NO: 3) and following previously described procedures (Brych et al. (2001) Protein Sci 10:2587-2599). Construction of the Symfoil-1 (for symmetric β-trefoil protein 1) mutant involved complete gene synthesis utilizing unique codons at symmetry-related positions. Expression and purification of recombinant proteins followed previously published procedures (Brych et al. (2001) Protein Sci 10:2587-2599). Purified protein was exchanged into 50 mM sodium phosphate, 0.1 M NaCl, 10 mM $(NH_4)_2SO_4$, 2 mM DTT, pH 7.5 ("crystallization buffer") for crystallization studies or 20 mM N-(2-acetamido)iminodiacetic acid (ADA), 0.1 M NaCl, 2 mM DTT, pH6.6 ("ADA buffer") for biophysical studies (DTT was omitted in all Symfoil mutants). An extinction coefficient of E280 nm (0.1%, 1 cm)=1.26 (Zazo M et al. (1992) Gene 113:231-238 and Tsai P K et al. (1993) Pharm Res 10:649-659) was used for FGF-1 and the extinction coefficient for all mutant forms was determined by the method of Gill and von Hippel (Gill S C and von Hippel P H (1989) Anal Biochem 182:319-326).

Isothermal Equilibrium Denaturation.

Isothermal equilibrium denaturation by guanidine HCl (GuHCl) was performed using either fluorescence or CD as previously described (Blaber S I et al. (1999) Biophys J 77:470-477 and Kim J et al. (2003) J Mol Biol 328:951-961). The effect of mutation upon protein stability ($\Delta\Delta G$) was calculated by taking the difference between the mid-point of denaturation ($C_m$ value) for reference and mutant proteins and multiplying by the average m value as described by Pace and Scholtz (Pace C N and Scholtz J M (1997) Protein Structure: A Practical Approach, ed Creighton T E (Oxford Univ Press, Oxford), pp 299-321), where a negative value indicates the mutation is stabilizing. In the case of Monofoil-4P and Difoil-4P proteins, the data were analyzed using a trimer-to-monomer isothermal equilibrium denaturation model (Backmann J et al. (1998) J Mol Biol 284:817-833 and Jelesarov I and Lu M (2001) J Mol Biol 307:637-656).

Differential Scanning Calorimetry (DSC).

All DSC data were collected on a VP-DSC microcalorimeter (GE Healthcare) as previously described (Blaber S I et al. (1999) Biophys J 77:470-477). Molar heat capacity data were analyzed using a two-state model as implemented in the DSCfit software package (Grek S B et al. (2001) Protein Pept Lett 8:429-436). The Monofoil-4P and Difoil-4P mutants were analyzed using a trimer-to-monomer thermal denaturation model (Backmann J et al. (1998) J Mol Biol 284:817-833 and Jelesarov I and Lu M (2001) J Mol Biol 307:637-656) implemented using the DataFit nonlinear least-squares-fit software package (Oakdale Engineering).

X-Ray Crystallization and Structure Determination.

Purified mutant protein in crystallization buffer was concentrated to 9-15 mg/mL and crystals were grown using either the hanging-drop or sitting-drop vapor diffusion method at room temperature. Crystals of Symfoil-1, Symfoil-2, Symfoil-4T, Symfoil-4V, and Symfoil-4P proteins grew in 1-3 wk from vapor diffusion against 1.8-2.3 M ammonium sulfate, 0.1-0.2 M lithium sulfate, and 0.1 M Tris pH 7.0. To minimize potential flexibility of the N-terminal region of Monofoil-4P and Difoil-4P polypeptides, residues from Phe1 to Lys10 were deleted (producing the Monofoil-4PΔ1-10 and Difoil-4PΔ1-10 mutants, respectively). Crystals of Monofoil-4PΔ1-10 and Difoil-4PΔ1-10 grew in 2 M ammonium sulfate, 0.1 M Na citrate pH 5.5. Crystals were mounted in a stream of gaseous nitrogen at 100 K and diffraction data were collected at either the Southeast Regional Collaborative Access Team 22-BM beam line ($\lambda$=1.00 Å) at the Advanced Photon Source, Argonne National Laboratory, using a MarCCD 300 detector (Mar USA) or at the X25 beam line of the National Synchrotron Light Source at Brookhaven National Laboratory, using an ADSC Q315 CCD detector. Each dataset was collected from a single crystal except Monofoil-4PΔ1-10 and Difoil-4PΔ1-10. Datasets from two crystals of Monofoil-4PΔ1-10 were combined for better completion and redundancy. Difoil-4PΔ1-10 crystals exhibited radiation sensitivity and diffraction data from three Difoil-4PΔ1-10 crystals were combined to yield acceptable completeness.

Diffraction data were indexed, integrated, and scaled using the HKL2000 software package (Otwinowski Z (1993) Proceedings of the CCP4 Study Weekend: "Data Collection and Processing", eds Sawyer L, Isaacs N, Bailey S (Science and Engineering Research Council, Daresbury Laboratory, England), pp 56-62 and Otwinowski Z and MinorW (1997) Meth Enzymol 276:307-326). Molecular replacement and model building utilized the PHENIX software package (Zwart P H et al. (2008) Methods Mol Biol 426:419-435), with 5% of the data in the reflection files set aside for Rfree calculations (Brunger A T (1992) Nature 355:472-475). Model building and visualization utilized the COOT molecular graphics software package (Emsley P and Cowtan K (2004) Coot: Model-building tools for molecular graphics. Acta Crystallogr, Sect D: Biol Crystallogr 60:2126-2132). His-tagged FGF-1 (Protein Data Bank ID code 1JQZ) was used as the search model in molecular replacement for all Symfoil mutant proteins. The resulting Symfoil-4P X-ray structure was used as a search model in molecular replacement with the Monofoil-4PΔ1-10 X-ray data. The correctly positioned Symfoil-4P structure was subsequently divided into three chains (A through C) representing the three individual Monofoil-4PΔ1-10 polypeptides. The Symfoil-4P X-ray structure was also used as the search model in molecular replacement with the Difoil-4PΔ1-10 X-ray data, yielding an acceptable solution with two independent copies of the β-trefoil search model in the asymmetric unit. Refinement of the Difoil-4PΔ1-10 structure initially utilized a twofold noncrystallographic symmetry (NCS) constraint (relating the two independent β-trefoil solutions). Chain definitions for the three independent polypeptide chains comprising the two intact β-trefoil folds were assigned based upon contiguous density in the $2F_o$-$F_c$ omit map. Refinement of the Difoil-4PΔ1-10 structure subsequently utilized a threefold NCS constraint for residue segments 11-38 of chains A, B, and C, and residue segments 52-79 of chains A, B, and C. Final refinement of the Difoil-4PΔ1-10 model did not utilize any NCS constraint. All X-ray structures, with the exception of Difoil-4P, yielded refined coordinates with >90% of residues in the most favored region of the Ramachandran plot and no residues in disallowed regions. The Difoil-4P structure yielded refined coordinates with 79% of residues in the most favored region and no residues in disallowed regions.

Calibrated Size-Exclusion Chromatography.

Calibrated size-exclusion chromatography was performed on a Hi-Load Superdex 75 26/60 column (318 mL column volume; GE Healthcare) on an AKTA FPLC system (GE Healthcare) in crystallization buffer at a flow rate of 2.5 mL/min. The column was calibrated using mass standards of bovine serum albumin (66.0 kDa), carbonic anhydrase (33.0 kDa), and cytochrome C (12.5 kDa) and a standard curve was fit to elution volume versus log (mw). Two-milliliter samples of 50 μM FGF-1 and mutant proteins were resolved and the apparent molecular masses were determined by comparison to the mass standard curve.

Analytical Ultracentrifugation.

Sedimentation velocity analytical ultracentrifugation experiments were performed in a Beckman XL-I centrifuge (Beckman Coulter, Inc.) using absorbance optics and measuring intensity scans at 280 nm. The experiments were performed at 20° C. in two-channel Epon centerpieces with an AN60 Ti rotor at 58,000 rpm and using 142 μM of Monofoil-4P, and 65 μM of Difoil-4P, equilibrated in ADA buffer. Data were analyzed using the UltraScan II version 9.9 software suite (Demeler B (2005) Modern Analytical Ultracentrifugation: Techniques and Methods, eds Scott D J, Harding S E, Rowe A J (Royal Society of Chemistry, Cambridge, UK), pp 210-229 and Schuck P and Demeler B (1999) Biophys J 76:2288-2296). All computations were performed on the TIGRE cluster at the University of Texas Health Science Center at San Antonio and the Texas Advanced Computing Center at the University of Texas in Austin. All data were first analyzed by two-dimensional spectrum analysis (Brookes E et al. (2010) Eur Biophys J 39:405-414) with simultaneous removal of time-invariant noise, and then by genetic algorithm refinement (Brookes E H and Demeler B (2007) Proceedings of the Ninth Annual Conference on Genetic and Evolutionary Computation (Association for Computing Machinery, London), pp 361-368), followed by Monte Carlo analysis (Demeler B and Brookes E (2008) Colloid Polym Sci 286:129-137). The partial specific volumes at 20° C. of the Monofoil-4P (0.716 cm$^3$/g) and Difoil-4P (0.715 cm$^3$/g) proteins were estimated from peptide sequence as described by Durchschlag (Durchschlag H (1986) Thermodynamic Data for Biochemistry and Biotechnology, edHinz H-J (Springer, Berlin), pp 45-128).

TABLE 1

Nomenclature for the β-trefoil mutant proteins comprising the top-down symmetric deconstruction of the FGF-1 protein and leading to the Monofoil-4P peptide.

| Mutant | Composition |
| --- | --- |
| SYM2 (1, 2) | FGF-1/Leu73Val/Val109Leu |
| SYM3 (1, 2) | SYM2/Leu44Phe |
| SYM4 (2) | SYM3/Cys117Val |
| SYM5 (2) | SYM4/Leu111Ile |
| SYM6 (2) | SYM5/Met67Ile |
| SYM6ΔΔ (3) | SYM6/Ala103Gly/Δ 104-106/Arg119Gly/Δ120-122 |
| SYM7ΔΔ (4) | SYM6ΔΔ/Phe22Tyr/Phe108Tyr |
| SYM9ΔΔ | SYM7ΔΔ/Lys12Val/Pro134Val |
| SYM10ΔΔ | SYM9ΔΔ/His93Gly |
| SYM11ΔΔ | SYM10ΔΔ/Leu26Asn/Asp68Asn/Thr69Pro/Lys112Asn/Lys113Pro/Asn114Asp |
| SYM12ΔΔ | SYM11ΔΔ/Asn95Val/Leu46Val/Glu87Val |
| SYM13ΔΔ | SYM12ΔΔ/Ile56Leu/Tyr97Leu |
| Symfoil-1 | SYM13ΔΔ chimera:(53)(12-14)(57-65)(24-47)(136)(90)(GGG) |
| Symfoil-2 | Symfoil-1/Val46Ile/Val87Ile/Val134Ile |
| Symfoil-3 | Symfoil-2/Gly51Asn/Gly92Asn/Gly139Asn |
| Symfoil-4T | Symfoil-3/Gln40Thr/Gln81Thr/Gln128Thr |
| Symfoil-4V | Symfoil-3/Gln40Val/Gln81Val/Gln128Val |
| Symfoil-4P | Symfoil-3/Gln40Pro/Gln81Pro/Gln128Pro |
| Difoil-4P | Symfoil-4P/Glu94stop |
| Monofoil-4P | Symfoil-4P/Glu53stop |

(1) Brych SR, Blaber SL, Logan TM, Blaber M(2001) Structure and stability effects of mutations designed to increase the primary sequence stmmetry within the core region of a β-trefoil. Protein Sci 10: 2587-2599.
(2) Brych SR, Kim J, Logan TM, Blaber M (2003) Accommodation of a highly symmetric core within a symmetric protein superfold. Protein Sci 12: 2704-2718.
(3) Brych SR, et al. (2004) Symmetric Primary and tertiary structure mutations within a symmetric superfold: A solution, not a constraint, to achieve a foldable polypeptide. J Mol Biol 344: 769-780.
(4) Dubey VK, Lee J, Blaber M (2005) Redesigning Symmetry-related "mini-core" regions of FGF-1 to increase primaty structure symmetry: Thermodynamic and functional consequences of structural symmetry. Protein Sci 14: 2315-2323.

TABLE 2

Crystallographic data collection and refinement statistics.

| Data collection | Symfoil-1 | Symfoil-2 | Symfoil-4T | Symfoil-4V | Symfoil-4P | Monofoil-4P* | Difoil-4P* |
| --- | --- | --- | --- | --- | --- | --- | --- |
| Space groups | I222 | P2$_1$ | I222 | I222 | I222 | P2$_1$2$_1$2$_1$ | I2$_1$2$_1$2$_1$ |
| Cell dimensions | | | | | | | |
| a, b, c, Å | 50.4, 53.4, 85.2 | 50.7, 53.6, 85.3 | 50.6, 53.5, 85.0 | 50.8, 53.7, 85.6 | 50.4, 53.2, 84.8 | 49.5, 53.5, 65.9 | 81.2, 85.4, 86.1 |
| α, β, γ, ° | 90.0, 90.0, 90.0 | 90.0, 90.1, 90.0 | 90.0, 90.0, 90.0 | 90.0, 90.0, 90.0 | 90.0, 90.0, 90.0 | 90.0, 90.0, 90.0 | 90.0, 90.0, 90.0 |
| Resolution, Å | 50.00-1.45 (1.48-1.45) | 50.00-1.45 (1.48-1.45) | 50.00-1.80 (1.83-1.80) | 50.00-1.75 (1.78-1.75) | 50.00-1.65 (1.68-1.65) | 50.00-1.48 (1.51-1.48) | 50.00-2.85 (2.90-2.85) |
| R$_{merge}$ | 5.1 (37.8) | 8.3 (39.8) | 9.3 (37.9) | 10.2 (34.5) | 5.0 (33.3) | 6.9 (35.8) | 11.9 (36.2) |
| I/σI | 53.6 (3.6) | 34.1 (2.9) | 67.1 (10.1) | 50.2 (8.1) | 59.7 (4.5) | 82.4 (8.4) | 33.0 (4.3) |

TABLE 2-continued

Crystallographic data collection and refinement statistics.

| Data collection | Symfoil-1 | Symfoil-2 | Symfoil-4T | Symfoil-4V | Symfoil-4P | Monofoil-4P* | Difoil-4P* |
|---|---|---|---|---|---|---|---|
| Completeness, % | 98.6 (85.8) | 97.8 (95.1) | 99.0 (98.2) | 98.3 (100) | 96.0 (73.8) | 99.0 (98.8) | 94.5 (61.8) |
| Redundancy | 7.0 (5.8) | 5.1 (2.5) | 9.7 (9.8) | 5.4 (5.0) | 9.3 (7.0) | 19.4 (16.6) | 6.1 (3.2) |
| Refinement | | | | | | | |
| Resolution, Å | 45.21-1.45 | 45.41-1.45 | 36.75-1.80 | 45.51-1.75 | 42.39-1.65 | 41.52-1.48 | 43.04-2.86 |
| No. reflections | 20,483 | 79,285 | 10,908 | 11,947 | 13,546 | 29,337 | 6,757 |
| $R_{work}/R_{free}$ | 19.6/22.7 | 18.6/21.5 | 17.7/21.8 | 19.3/22.4 | 19.0/22.6 | 18.1/20.4 | 22.7/31.0 |
| No. atoms | | | | | | | |
| Protein | 998 | 4,209 | 987 | 992 | 996 | 1,062 | 1,912 |
| Ligand/ion | 13 | 92 | 19 | 20 | 19 | 25 | 15 |
| Water | 154 | 624 | 86 | 78 | 93 | 203 | 0 |
| B factor | | | | | | | |
| Protein | 23.4 | 19.2 | 26.3 | 29.3 | 26.8 | 18.1 | 60.6 |
| Ligand/ion | 27.5 | 31.6 | 39.7 | 40.9 | 38.7 | 52.5 | 56.5 |
| Water | 34.8 | 33.9 | 36.4 | 38.5 | 37.0 | 37.5 | — |
| Rms deviations | | | | | | | |
| Bond length, Å | 0.007 | 0.006 | 0.007 | 0.006 | 0.007 | 0.006 | 0.002 |
| Bond Angle, ° | 1.14 | 1.09 | 1.10 | 1.05 | 1.12 | 1.07 | 0.549 |
| PDB ID code | 3O49 | 3O4A | 3O4B | 3O4C | 3O4D | 3OL0 | 3OGF |

Each dataset was collected from a single crystal except Monofoil-4P and Difoil-4P. Two crystals were used for Monofoil-4P and three crystals were used for Difoil-4P dataset. Values in Parentheses are for the highest-resolution shell. PDB, Protein Data Bank.
*Δ1-10 mutant form.

TABLE 3

Thermodynamic parameters for FGF-1, SYM, and Symfoil mutant proteins determined from isothermal equilibrium denaturation by GuHCl in ADA buffer.

| Protein | ΔG, kJ/mol | m value, kJ/mol M | $C_m$, M | ΔΔG, kJ/mol |
|---|---|---|---|---|
| FGF-1 | 21.1 ± 0.6 | 18.9 ± 0.6 | 1.11 ± 0.01 | — |
| FGF-1* (1) | 26.6 ± 0.9 | 20.3 ± 0.7 | 1.29 ± 0.01 | — |
| Transform 1 | | | | |
| SYM5 (2) | 20.8 ± 0.5 | 19.4 ± 0.1 | 1.07 ± 0.02 | 0.8 |
| SYM6ΔΔ (3) | 33.9 ± 0.6 | 17.7 ± 0.4 | 1.91 ± 0.02 | −14.6 |
| SYM7ΔΔ* (1) | 41.2 ± 0.6 | 19.2 ± 0.8 | 2.14 ± 0.01 | −16.8† |
| Transform 2 | | | | |
| SYM9ΔΔ | 54.0 ± 1.4 | 16.7 ± 0.4 | 3.24 ± 0.01 | −37.9 |
| SYM10ΔΔ | 66.0 ± 3.1 | 17.9 ± 0.9 | 3.68 ± 0.01 | −47.3 |
| SYM11ΔΔ | 56.4 ± 3.2 | 16.2 ± 0.8 | 3.48 ± 0.02 | −41.6 |
| Transform 3 | | | | |
| SYM12ΔΔ | 64.6 ± 0.7 | 16.5 ± 0.2 | 3.91 ± 0.01 | −49.6 |
| SYM13ΔΔ | 55.6 ± 2.5 | 13.9 ± 0.5 | 4.00 ± 0.03 | −47.4 |
| Symfoil-1 | 28.8 ± 0.3 | 18.5 ± 0.2 | 1.55 ± 0.01 | −8.2 |
| Stability optimization | | | | |
| Symfoil-2 | 37.9 ± 0.2 | 17.4 ± 0.1 | 2.18 ± 0.01 | −19.4 |
| Symfoil-3 | 41.0 ± 0.1 | 17.3 ± 0.1 | 2.37 ± 0.01 | −22.8 |
| Symfoil-4T | 43.2 ± 0.3 | 17.4 ± 0.1 | 2.48 ± 0.01 | −24.9 |
| Symfoil-4V | 44.2 ± 0.1 | 15.4 ± 0.1 | 2.86 ± 0.01 | −30.0 |
| Symfoil-4P | 55.1 ± 0.7 | 15.3 ± 0.3 | 3.60 ± 0.01 | −42.6 |
| | $\Delta G^0{}_0$, kJ/mol | | | |
| Tranform 4 Monofoil-4P | | | | |
| 2 μM | 71.8 ± 0.8 | 7.8 ± 0.4 | 1.64 ± 0.01 | |
| 4 μM | 70.6 ± 0.2 | 7.9 ± 0.1 | 1.71 ± 0.04 | |
| 10 μM | 67.4 ± 1.0 | 7.4 ± 0.5 | 1.64 ± 0.03 | |
| Difoil-4P | | | | |
| 2 μM | 83.8 ± 0.2 | 13.5 ± 0.1 | 1.72 ± 0.02 | |
| 4 μM | 82.2 ± 0.8 | 13.8 ± 0.3 | 1.82 ± 0.02 | |
| 10 μM | 82.1 ± 1.3 | 15.1 ± 0.4 | 1.96 ± 0.03 | |

(1) Dubey VK, Lee J, Blaber M (2005) Redesigning symmetry-related "mini-core" regions of FGF-1 to increase primary structure symmetry. Thermodynamic and functional consequences of structural symmetry. Protein Sci 14: 2315-2323.
(2) Brych SR, Kim J, Logan TM, Blaber M (2003) Accommodation of a highly symmetric core within a symmetric protein superfold. Protein Sci 12: 2704-2718.
(3) Brych SR, et al. (2004) Symmetric primary and tertiary structure mutations within a symmetric superfold: A solution, not a constraint, to achieve a foldable polypeptide. J Mol Biol 344: 769-780.
*Determined in crystallization buffer.
†ΔΔG in comparison to FGF-1 in crystallization buffer.

Example 3: A Polypeptide "Building Block" for the β-Trefoil Fold Identified by "Top-Down Symmetric Deconstruction"

Transform #1: Top-Down SD of Core Positions.

Attempts to introduce a symmetric constraint on the hydrophobic core-packing group, without also making alterations to the asymmetric FGF-1 tertiary structure, met with limited success. An alternative core-packing group involving five residue positions (SYM5 mutant, FIG. 8A, FIG. 8B, and FIG. 8C) was identified that was essentially equivalent to the FGF-1 thermostability and folding cooperativity (Brych, S. R. et al. (2001). Protein Sci. 10, 2587-2599 and Brych, S. R. et al. (2003) Protein Sci. 12, 2704-2718). Folding and unfolding kinetic data showed that the SYM5 mutant exhibited folding and unfolding rates similar to that of the FGF-1 protein including the characteristic biphasic folding behavior (Brych, S. R. et al. (2003) Protein Sci. 12, 2704-2718). Attempts at introducing a further symmetric constraint (Ile) at symmetry-related positions 25, 67, and 111 (SYM6 mutant) essentially failed due to substantial (10.9 kJ/mol) destabilization. However, subsequent deletion mutations in the third trefoil-fold subdomain, which increased the tertiary-structure symmetry, enabled the symmetric Ile solution at positions 25, 67, and 111 (SYM6ΔΔ mutant, FIG. 9) with a substantial (16.1 kJ/mol) increase in stability in comparison to FGF-1.24 This increase in stability was due exclusively to an increase in the folding kinetics; additionally, the SYM6ΔΔ mutant exhibited single-exponential folding behavior (unlike FGF-1 and SYM2-SYM6 mutants) (Brych, S. R. et al. (2004). J. Mol. Biol. 344, 769-780). Construction of the SYM6ΔΔ mutant also coincided with essential loss of affinity for heparin-Sepharose and an order of magnitude increase in $K_D$ for sucrose octasulfate (a disaccharide mimic of heparin) (Brych, S. R. et al. (2004). J. Mol. Biol. 344, 769-780).

Subsequent symmetric mutations SYM7ΔΔ and SYM8ΔΔ addressed additional buried positions (separate from the central hydrophobic core). Symmetry-related positions Ile42, Cys83, and Ile130 were initially constrained to Ile residues (by mutation Cys83Ile); however, this failed due to substantial (9.9 kJ/mol) destabilization (Dubey, V. K. et al. (2005). Protein Sci. 14, 2315-2323). Thus, this symmetric set of buried residues was constrained to Cys mutations (SYM8ΔΔ), which were tolerated with essentially neutral effect on stability (in comparison to SYM6ΔΔ; FIGS. 8A-8C). In FGF-1, the symmetry-related residues Leu14, Ile56, and Tyr97 form a core-solvent interface at the "top" of the central β-barrel. Attempts to enforce a symmetric constraint as a final step of transform #1 by evaluating Ile56Leu, Tyr97Ile, or Leu14Ile point mutations failed due to substantial destabilizing and precipitation; thus, these positions remained wild type (i.e., asymmetric) at the end of transform #1.

Overall, the application of transform #1 resulted in an increase in 3-fold primary-structure symmetry from 2% (i.e., 1 of 42 positions) in FGF-1 to 21% (i.e., 9 of 42 positions) in SYM8ΔΔ. Furthermore, deletions in the third trefoil-fold subdomain resulted in its length equaling that of the second trefoil-fold subdomain, thereby increasing the tertiary-structure symmetry. Substantial nonadditive and cooperative effects were observed in the application of transform #1. The SYM3 mutant was 5.0 kJ/mol more stable than the simple sum of the constituent point mutations (Brych, S. R. et al. (2001). Protein Sci. 10, 2587-2599) the SYM5 mutant was 12.0 kJ/mol more stable than the sum of the constituent point mutations (Brych, S. R. et al. (2003) Protein Sci. 12, 2704-2718); and the Met67Ile point mutation was 9.4 kJ/mol destabilizing in the SYM5 background, but was completely neutral as regarding stability when constructed in the same protein with the above-described tertiary-structure deletions in the third trefoil-fold subdomain (Brych, S. R. et al. (2004). J. Mol. Biol. 344, 769-780).

Surface plasmon resonance (SPR) data for the binding constants of the SYM6ΔΔ and SYM7ΔΔ mutants with the extracellular domain of the FGF receptor-1c (FGFR-1c) protein demonstrated an approximately 2 orders of magnitude increase in $K_D$ (i.e., reduction in receptor affinity) for SYM6ΔΔ and another order of magnitude increase in KD for SYM7ΔΔ (Table 7). Conversely, the 3T3 fibroblast mitogenic assay showed an order of magnitude increase in mitogenic potency for the SYM6ΔΔ mutant in comparison to FGF-1 (Table 8). Crystal structures were reported for the SYM2,23 SYM3,23 SYM4,24 and SYM524 mutants. Although the other core mutants did not crystallize, a Phe108Tyr mutation within the SYM6ΔΔ protein crystallized and yielded a 1.60 Å resolution data set and is reported here (Table 6).

TABLE 4

SPR binding constants for FGF-1 and mutant proteins with soluble FGFR-1c.

| Protein | $K_D$ (M) | $R_{max}$ (RU) | $X^2$ (RU$^2$) |
|---|---|---|---|
| FGF-1 | $(6.96 \pm 0.04) \times 10^{-9}$ | 24.9 | 0.185 |
| SYM6ΔΔ | $(2.09 \pm 0.02) \times 10^{-7}$ | 27.1 | 0.016 |
| SYM7ΔΔ | $(1.76 \pm 0.81) \times 10^{-6}$ | 61.8 | 0.029 |
| SYM9ΔΔ | N.D. | | |
| SYM10ΔΔ | N.D. | | |
| SYM11ΔΔ | N.D. | | |
| SYM12ΔΔ | N.D. | | |
| SYM13ΔΔ | N.D. | | |
| Symfoil-1 | N.D. | | |
| SYM6ΔΔ/K12V/P134V | N.D. | | |
| SYM7ΔΔ/K12V/P134V | N.D. | | |

N.D., no binding detected.

TABLE 5

Summary of the mitogenic activity of FGF-1 and mutant proteins with 3T3 fibroblasts.

| Protein | $EC_{50}$ (ng/ml) |
|---|---|
| FGF-1 | 58.4 ± 25.4 |
| SYM6ΔΔ[25] | 0.84 ± 0.43 |
| K12V/P134V[27] | 1.80 ± 0.90 |
| SYM6ΔΔ/K12V/P134V | 741 ± 302 |
| SYM10ΔΔ | N.D. |

N.D. no activity detected.

TABLE 6

Crystallographic data collection and refinement statistics for SYM6ΔΔ (F108Y mutant).

| Data collection | |
|---|---|
| Space group | P1 |
| Cell dimensions | |
| a, b, c (Å) | 46.9, 56.9, 61.9 |
| α, β, γ (°) | 64.9, 89.7, 71.2 |
| Resolution (Å) | 50.00-1.60 (1.66-1.60)$^a$ |
| Mossicity (°) | 0.92 |
| Mathews coefficients (Å$^3$/Da) | 2.12 |
| Redundancy | 3.7 (2.6) |
| Total reflections | 256, 934 |
| Unique collections | 68.593 |
| I/σI | 30.8 (2.9) |
| Completeness (%) | 96.3 (88.4) |
| $R_{merge}$ | 11.1 (34.3) |
| Refinement | |
| Resolution (Å) | 27.71-1.60 |
| $R_{work}/R_{free}$ | 17.0/20.3 |
| No. of atoms | |
| Protein | 3977 |
| Ligand/ion | 12 |
| Water | 578 |
| B-factor | |
| Protein | 23.8 |
| Ligand/ion | 23.5 |
| Water | 33.7 |

TABLE 6-continued

Crystallographic data collection and refinement
statistics for SYM6ΔΔ (F108Y mutant).

| RMSDs | |
|---|---|
| Bond length (Å) | 0.006 |
| Band angle (°) | 1.01 |
| Ramachandran plot: | |
| Most favored(%) | 91.2 |
| Additionally allowed (%) | 8.6 |
| Generously allowed (%) | 0.2 |
| Disallowed region (%) | 0.0 |
| PDB code | 3O3Q |

*Values in parentheses are for the highest-resolution shell.

Transform #2: SD of reverse turns. The buried free cysteine residues introduced into the SYM8ΔΔ mutant at positions 42 and 130 proved problematic for folding and stability studies due to the need for reducing agents in the buffer; thus, these residue positions were reverted to Ile as part of the initial application of transform #2 with the design of the SYM9ΔΔ mutant (FIG. 10). The introduction of a (partial) symmetric constraint on β-turn regions, ending with the SYM11ΔΔ mutant, was achieved with a further substantial increase in stability and slight reduction in folding cooperativity m value. The SYM11ΔΔ mutant (the product of transform #2) was 23.2 kJ/mol more stable than the SYM8ΔΔ mutant and 41.6 kJ/mol more stable than the FGF-1 starting protein. None of the mutants in this transform (i.e., SYM9ΔΔ, SYM10 ΔΔ, and SYM11 ΔΔ) exhibited any detectable binding to the FGFR-1c protein in SPR studies (Table 7); furthermore, the SYM10ΔΔ mutant was devoid of any detectable mitogenic activity (Table 8). After the application of transform #2, the 3-fold symmetry of the primary structure increased from 21% (9 of 42 positions in SYM7ΔΔ) to 26% (11 of 42 positions in SYM11ΔΔ) with no change in the tertiary structure (i.e., length) of the individual trefoil-fold subdomains (FIG. 10).

Transform #3: SD of β-Strands.

The introduction of a (partial) symmetric constraint on β-strand secondary structure, starting with the SYM11ΔΔ mutant and ending with the SYM13ΔΔ mutant, was achieved with a further gain in stability (FIG. 11). The SYM13ΔΔ mutant was 7.8 kJ/mol more stable than the SYM11ΔΔ mutant and 47.4 kJ/mol more stable than the FGF-1 starting protein; however, there was a gradual decrease observed in the folding cooperativity m value from 18.9 kJ/mol M in FGF-1 to 16.2 kJ/molM in SYM11ΔΔ and 13.9 kJ/molM in SYM13ΔΔ. SPR studies confirmed that none of the mutations in this transform (i.e., SYM11ΔΔ, SYM12ΔΔ, and SYM13ΔΔ) possess any detectable affinity for the FGFR-1c protein (Table 7). The 3-fold symmetry of the primary structure increased from 26% (11 of 42 positions in SYM11ΔΔ) to 33% (14 of 42 positions in SYM13ΔΔ) (FIG. 11). At this point, in an attempt to speed the SD process, Applicants constructed a combined SYM13ΔΔ/Cys16Ser/Thr59Ser/Lys100Ser/Asp140Gly/His41Ala/Ile42Thr/Phe44Trp/Glu82Ala/Cys83Thr/Phe85Trp/Ile130Thr/Phe132Trp mutant in the SYM13ΔΔ mutant with the combined goal of eliminating the buried free thiols at positions Cys16 and Cys83, increasing the symmetric constraint on β-strand secondary structure, and simultaneously introducing buried Trp residues as a useful fluorescence probe of protein folding. Although this mutant was folded and soluble, it exhibited poor stability (ΔG=17.0 kJ/mol) and notably poor folding cooperativity m value (5.3 kJ/molM). Thus, this mutant was abandoned, and, instead, a chimera strategy was pursued to eliminate the buried free thiols and increase the 3-fold symmetric constraint.

The initial chimera design focused on invoking a symmetric constraint utilizing residue positions that comprise the van der Waals contacts of Ser58 and Ile42 as a means to eliminate reactive buried thiols at symmetry-related positions Cys16 and Cys83. However, since this substitution of primary structure involved a substantial portion of the remaining asymmetry within the SYM13ΔΔ mutant, the chimera strategy was expanded to comprise regions that defined the entire molecule and thereby enforce a complete primary- and tertiary-structure symmetric constraint in a single mutagenesis step (producing the Symfoil-1 protein; FIG. 11). In comparison to SYM13ΔΔ, the Symfoil-1 protein exhibited a substantial (39.7 kJ/mol) loss of stability; however, the folding cooperativity m value increased from 13.9 to 18.5 kJ/molM, essentially recovering the folding cooperativity of the FGF-1 starting protein. Furthermore, while the Symfoil-1 protein was destabilized in comparison to SYM13ΔΔ, it was nonetheless significantly (8.3 kJ/mol) more stable than the FGF-1 starting protein. Notably, in contrast to FGF-1 [which aggregates upon thermal denaturation in the absence of low concentrations of added guanidine HCl (GuHCl) denaturant (Blaber, S. I. et al. (1999). Biophys. J. 77, 470-477)], differential scanning calorimetry (DSC) analysis of the Symfoil-1 protein demonstrated reversible, two-state thermal denaturation (i.e., $\Delta H_{van't\ Hoff}/\Delta H_{cal}$~1.0), with excellent recovery of enthalpy upon cooling, under all buffer conditions tested (Table 7).

TABLE 7

DSC data of FGF-1 and mutant proteins in ADA buffer.

| Protein | ΔH (kJ/mol) | ΔC$_p$(kJ/mol K) | T$_m$ (K) | H$_{vH}$/H$_{cal}$ | ΔΔG (kJ/mol)$^a$ |
|---|---|---|---|---|---|
| 0.7M GuHCl | | | | | |
| FGF-1[22] | 257 ± 3 | 9.33 ± 0.33 | 312.6 ± 0.10 | 1.08 ± 0.10 | — |
| Symfoil-1 | 311 ± 6 | 6.08 ± 0.63 | 325.4 ± 0.12 | 1.02 ± 0.12 | −10.4 |
| Symfoil-2 | 394 ± 6 | 6.97 ± 1.11 | 335.3 ± 0.11 | 1.02 ± 0.03 | −21.3 |
| Symfoil-3 | 417 ± 4 | 8.64 ± 0.56 | 338.4 ± 0.05 | 1.18 ± 0.01 | −24.5 |
| Symfoil-4T | 426 ± 3 | 9.24 ± 0.70 | 340.2 ± 0.09 | 1.16 ± 0.03 | −26.5 |
| Symfoil-4V | 472 ± 4 | 8.68 ± 0.19 | 343.5 ± 0.02 | 1.14 ± 0.01 | −31.6 |
| Symfoil-4P | 639 ± 5 | 4.66 ± 0.84 | 354.0 ± 0.03 | 1.11 ± 0.01 | −43.2 |
| 0M GuHCl | | | | | |
| Symfoil-1 | 400 ± 2 | 6.36 ± 0.89 | 333.9 ± 0.08 | 1.04 ± 0.02 | |
| Symfoil-2 | 460 ± 8 | 6.16 ± 0.94 | 341.7 ± 0.08 | 1.13 ± 0.06 | |
| Symfoil-3 | 494 ± 8 | 8.24 ± 0.69 | 344.5 ± 0.03 | 1.10 ± 0.02 | |
| Symfoil-4T | 501 ± 9 | 8.67 ± 0.67 | 346.6 ± 0.03 | 1.12 ± 0.03 | |

TABLE 7-continued

DSC data of FGF-1 and mutant proteins in ADA buffer.

| | | | | |
|---|---|---|---|---|
| Symfoil-4V | 557 ± 4 | 5.77 ± 2.61 | 348.9 ± 0.09 | 1.04 ± 0.04 |
| Symfoil-4P | 599 ± 10 | 5.67 ± 1.01 | 358.1 ± 0.04 | 1.03 ± 0.07 |

| | $\Delta H^\circ$ (kJ/mol)[b] | $\Delta C_p$ (kJ/molK)[b] | $T_m$ (K)[b] | $H_{vH}/H_{cal}$[b] | $K_D$ (M$^2$) |
|---|---|---|---|---|---|
| Monofoil-4P (20 μM) | 434 ± 3 | 8.61 ± 0.33 | 333.6 ± 0.05 | 0.84 ± 0.10 | 0.93 × 10$^{-8}$ ± 0.40 |
| Monofoil-4P (40 μM) | 399 ± 5 | 7.61 ± 0.07 | 334.0 ± 0.10 | 0.93 ± 0.07 | 2.07 × 10$^{-8}$ ± 0.70 |
| Monofoil-4P (80 μM) | 419 ± 2 | 7.45 ± 0.07 | 335.7 ± 0.10 | 0.94 ± 0.06 | 5.72 × 10$^{-8}$ ± 1.80 |
| Difoil-4P (20 μM) | 701 ± 5 | 8.70 ± 0.10 | 349.1 ± 0.05 | 0.97 ± 0.04 | 3.58 × 10$^{-11}$ ± 2.3 |
| Difoil-4P (40 μM) | 733 ± 5 | 8.88 ± 0.08 | 346.2 ± 0.05 | 0.97 ± 0.04 | 9.56 × 10$^{-11}$ ± 4.0 |

[a]Determined at 332 K in reference to FGF-1.
[b]Two-state trimer dissociation moded.

A comparison of the primary structure of FGF-1 with Symfoil-1 shows that the SD was associated with a total of 76 mutated positions and 4 overall deleted positions. The first trefoil-fold subdomain of Symfoil-1 is 67% identical (28 of 42 positions) with no insertions or deletions relative to the same subdomain in FGF-1; the second trefoil-fold subdomain is 39% identical (16 of 41 positions) with one additional residue in the Symfoil-1 subdomain; and the third trefoil-fold subdomain is 11% identical (5 of 47 positions) with five residues deleted in the Symfoil-1 subdomain. Notably, while the FGF-1 sequence contains instances of all 20 common amino acids, the Symfoil-1 sequence contains only 16 unique amino acids and is devoid of Ala, Cys, Trp, and Met residues. While the elimination of reactive thiols (Cys residues) was part of the design strategy, loss of the other residues was an unanticipated consequence of the SD. A crystal structure of the Symfoil-1 protein confirmed the precise 3-fold identical side-chain rotamers and regions of solvent structure (Lee, J. & Blaber, M. (2011). Proc. Natl Acad. Sci. USA, 108, 126-130). Additionally, the Symfoil series of mutants contained Tris in the crystallization mother liquor, and this C3 symmetric molecule was observed precisely bound on the 3-fold axis of structural symmetry at the "bottom" of the β-barrel (FIG. 12). Isothermal titration calorimetry (ITC) studies of Tris binding (using the Symfoil-2 protein) demonstrated that Tris binding is an enthalpy driven process.

Transform #4: Stability Optimization/SD Fragmentation.

The stability optimization of the Symfoil-1 protein, progressing through the Symfoil-2, Symfoil-3, Symfoil-4T, Symfoil-4V, and culminating in the Symfoil-4P protein, resulted in a significant increase in stability with modest reduction in the folding cooperativity m value (FIGS. 13A and 13B). The Symfoil-4P protein was 35.9 kJ/mol more stable than the Symfoil-1 protein and 42.6 kJ/mol more stable than the initial FGF-1 protein. The progressive increase in stability for this set of mutants was associated not only with an increase in folding rate constant but an even more substantial decreasing of the unfolding rate constant (Table 8). The slowest kinetic data that could be practically obtained were on the order of $1 \times 10^{-4}$ s$^{-1}$ (ln $k_{obs}$ approximately −9); thus, data for the "unfolding arm" of the Symfoil-4P mutant were effectively truncated at this region (FIG. 14). There was excellent agreement between the midpoint of denaturation as determined from the isothermal equilibrium data and folding kinetics, further supporting the two-state folding assumption. There was similar agreement for the derived ΔΔG stability values, although these values deviated somewhat with increasing stability (and the associated longer incubation times required for equilibrium).

The protease-resistance properties for this set of mutants correlated with their stability, and the most stable Symfoil-4P mutant was 3-4 orders of magnitude more resistant to proteolysis than the FGF-1 starting protein (FIG. 15).

Expressed Monofoil-4P and Difoil-4P proteins, representing monomer and dimer trefoil-fold subdomains of the Symfoil-4P protein, respectively, were soluble during purification. The Monofoil-4P and Difoil-4P proteins resolved as single peaks on calibrated size-exclusion chromatography, with apparent masses, indicating a homogenous oligomeric form (with n~3) and with no detectable monomer form present with either protein (Lee, J. & Blaber, M. (2011). Proc. Natl Acad. Sci. USA, 108, 126-130). In analytical ultracentrifugation studies, Monofoil-4P and Difoil-4P proteins sedimented as homogeneous forms with $S_{20,w}$ values of 2.31±0.036 and 3.18±0.021 S, respectively, and with corresponding molecular masses of 18.8 and 29.8 kDa, respectively (Lee, J. & Blaber, M. (2011). Proc. Natl Acad. Sci. USA, 108, 126-130). The molecular mass of the Monofoil-4P (6.4 kDa) and Difoil-4P (11.2 kDa) polypeptides therefore indicated a homotrimer in solution for both polypeptides, with no evidence of monomeric or higher-order oligomeric forms.

DSC analyses showed that the molar calorimetric enthalpy for the Monofoil-4P trimer was approximately 80% that of the Symfoil-4P protein, while the molar calorimetric enthalpy for the Difoil-4P trimer was approximately 23% greater than that of the Symfoil-4P protein (FIG. 16). The $H_{van't\ Hoff}/H_{cal}$ ratio was near unity for both the Monofoil-4P and Difoil-4P polypeptides, obtained with a trimer dissociation model (Table 7). There were only modest concentration-dependent effects on the thermodynamic parameters over the 20-80 μM range evaluated, and the calorimetrically derived KD value for the Monofoil-4P protein was 10-50 nM, while the Difoil-4P exhibited a subnanomolar (0.04-0.10 nM) $K_D$ value. The Monofoil-4P trimer was thus less stable than the Difoil-4P trimer, which in turn was less stable than the Symfoil-4P protein; however, each of these oligomers had a higher $T_m$ and enthalpy of unfolding than FGF-1. Crystal structures of the Monofoil-4P and Difoil-4P proteins confirmed homotrimer assemblies that reconstituted single and dual β-trefoil protein folds with essential structural identity to the Symfoil-4P protein (Lee, J. & Blaber, M. (2011). Proc. Natl Acad. Sci. USA, 108, 126-130) (FIG. 12).

Evidence of structural symmetry is widespread in naturally evolved protein folds (Orengo, C. A. et al. (1994). Nature, 372, 631-634, Thornton, J. M. et al. (1999). J. Mol. Biol. 293, 333-342 and Kim, C. et al. (2010). BMC Bioinf. 11, 303-318) presumably reflecting gene duplication and fusion events responsible for their emergence and suggesting a strategy to simplify bottom-up hierarchical de novo design (i.e., via symmetric self-assembly of an appropriately designed polypeptide building block) (Richardson, J. & Richardson, D. C. (1989). Trends Biochem. Sci. 14, 304-309, Hecht, M. H. et al. (1990). Science, 249, 884-891 and Ghirlanda, G. et al. (2002). J. Mol. Biol. 319, 243-253). Despite the attractiveness of a symmetric design principle, bottom-up design efforts have not achieved widespread success. Here, Applicants have asked whether an alternative approach (SD) can be used to successfully identify a polypeptide building block for a symmetric target architecture. This novel approach offers potential advantages for de novo design but also involves risks related to poorly understood aspects of protein folding. SD involves a significant reduction in sequence complexity; however, reduced sequence complexity and symmetric primary structure are features associated with natively unstructured proteins and protein aggregation (Wootton, J. C. & Federhen, S. (1993). Computers Chem. 17, 149-163, Romero, P. et al. (2001). Proteins, 42, 38-48, Wright, C. F. et al. (2005). Nature, 438, 878-881 and Hoang, T. X. et al. (2006). Proc. Natl Acad. Sci. USA, 103, 6883-6888). Thus, it is not apparent, a priori, that SD can produce a foldable polypeptide. Additionally, the final stage of SD involves fragmentation to yield the repeating polypeptide motif; with the expectation that this peptide will spontaneously assemble (as a homomultimer) and yield the correct target architecture. Such fragmentation potentially exposes substantial hydrophobic surface, and multimer assembly is achieved with a significant entropic penalty; additionally, in the case of the β-trefoil fold, no known example exists of its assembly via a homotrimer. Thus, it is not obvious that the solubility, folding, and thermodynamic properties of a polypeptide building block, necessary to spontaneously assemble as a homotrimer forming a β-trefoil fold, are realistically achievable. However, these types of issues are inherent in all de novo protein design efforts that attempt to exploit bottom-up hierarchical design of symmetric protein architecture. A primary advantage of SD is that the design process starts with a naturally evolved protein that is soluble, thermostable, and foldable; as long as mutations to enforce a symmetric constraint remain within foldable, thermostable "sequence space," a design solution is possible.

The 3-fold symmetric β-trefoil fold was selected as the target architecture for SD. Structural symmetries higher than 2-fold provide opportunities for subdomain mismatches during folding that can contain a significant fraction of native-like contacts but are nonetheless misfolded; thus, the β-trefoil architecture addresses folding issues inherent to higher-symmetry architecture. Additionally, unlike certain other symmetric protein architectures [e.g., the β-propeller or (β/α)8-barrel], the β-trefoil architecture contains a substantial and cooperatively packed central hydrophobic core (comprising ~14%, or 18 of 126, of the total residues); thus, the β-trefoil fold is representative of a single-domain globular protein. The β-trefoil protein selected for SD is FGF-1, which exhibits a substantial lack of symmetry at both the primary- and the tertiary-structure level as well as poor mesophilic thermostability; thus, attempting SD with FGF-1 is nontrivial. An initial size-exclusion chromatography study of peptide fragments of FGF-1 (residues 10-52, 53-93, and 94-140; representing the three independent trefoil-fold subdomains), either alone or in various combinations, yielded no evidence of self assembly into a multimeric structure (and, in fact, these peptides were largely insoluble). Overall, therefore, the selection of the β-trefoil as the target architecture for SD (and the selection of FGF-1 as the proxy) is highly appropriate.

The strategy utilized in pursuing SD involved the sequential application of symmetric transforms starting with the core and then proceeding to add reverse turn and β-strand structural elements, respectively. Interplay between primary- and tertiary structure symmetry became apparent when SD of the core region was attempted. Symmetric mutations that were poorly tolerated in the FGF-1 background were neutral or favorable when constructed within a mutant background that increased the tertiary structure symmetry (involving the deletion of two extended surface loop regions within the third trefoil-fold subdomain). Thus, symmetric transforms of the primary and tertiary structure were mutually supportive in terms of stability and folding.

The completion of transform #1 (symmetric core) did not completely abolish FGF-1 mitogenic activity, although the symmetric tertiary-structure deletions essentially abolished heparin-binding functionality. Curiously, although the SYM6ΔΔ mutant had substantially reduced heparin affinity, its mitogenic activity in 3T3 fibroblast cell assays increased by almost 2 orders of magnitude. A ternary complex of FGF-1, FGFR, and heparin is reportedly essential for FGF-1 signal transduction; 33-35 additionally, the heparin-binding affinity of FGF-1 promotes sequestration onto heparin and heparan glycans present in the extracellular matrix and cell surface (Bashkin, P. et al. (1989). Biochemistry, 28, 1737-1743, Weiner, H. L. & Swain, J. L. (1989). Proc. Natl Acad. Sci. USA, 86, 2683-2687 and Chintala, S. K. et al. (1994). Arch. Biochem. Biophys. 310, 180-186). Thus, while the SYM6ΔΔ mutant retains sufficient heparin affinity for signal transduction, it may not readily be sequestered on cell-surface heparan proteoglycans (and a greater effective concentration may be available in solution for receptor binding). Studies of additional stability mutants at the end of transform #1 provide evidence of a loss of essential dynamics necessary for FGFR-binding function. The SYM6ΔΔ mutant is highly active in the 3T3 fibroblast mitogenic assay (Table 8). A Lys12Val/Pro134V double mutant in FGF-1 that is also highly active in the mitogenic assay was previously described (Dubey, V. K. et al. (2007). J. Mol. Biol. 371, 256-268) (Table 8). Both mutations are substantially stabilizing; the SYM6ΔΔ mutant provides 16.1 kJ/mol of additional thermostability, and the Lys12Val/Pro134V double mutant provides 19.1 kJ/mol of additional thermostability. The combination of these mutations produces a mutant that is, surprisingly, essentially inactive in the mitogenic assay (Table 8). Applicants conclude that the substantial increase in thermostability (i.e., ΔΔG, approximately −35 kJ/mol) eliminates structural dynamics essential for signal transduction function. Thus, multiple aspects of FGF-1 functionality were being eliminated early in the SD process; certainly by the development of the SYM10ΔΔ mutant (in transform #2), key properties of heparin-binding, FGFR affinity, dynamics essential for FGF function, and associated mitogenic activity were lost. Nonetheless, the protein remained within foldable, thermostable sequence space.

When a stability screen for mutant selection was utilized, the thermostability increased continuously during the application of transforms #1-3 (FIG. 17). Thus, the imposition of a symmetric constraint had a net effect of a loss of function, but a greater than twofold gain in $\Delta G_u$, compared to FGF-1. Although FGF-1 exhibits poor mesophilic stability, the many mutant examples with increased thermostability suggest that the β-trefoil architecture is intrinsically capable of substantial thermostability, and there is no reason to believe that the various mutant forms described in the present study represent the optimum possible thermostability. The "stability/function trade-off" hypothesis posits that functional residues are often accommodated at the expense of overall stability (Schreiber, G. et al. (1994) Structure, 2, 945-951, Shoichet, B. K. et al. (1995). Proc. Natl Acad. Sci. USA, 92, 452-456, Beadle, B. M. & Shoichet, B. K. (2002). J. Mol. Biol. 321, 285-296, Bloom, J. D. et al. (2004). Biophys. J. 86, 2758-2764, Bloom, J. D. et al. (2006). Proc. Natl Acad. Sci. USA, 103, 5869-5874 and Tokuriki, N. et al. (2008). PLoS Comput. Biol. 4, e1000002) and the results are consistent with this hypothesis. The present results prompt Applicants to propose a "symmetry/function trade-off" hypothesis in that aspects of structural asymmetry are associated with function (at the expense of stability). Applicants note that development of a symmetric β-trefoil fold resulted in the emergence of an unanticipated novel "functionality," namely, binding specificity for a $C_3$ symmetric molecule (Tris).

While the stability of the original mesophilic FGF-1 protein could be moved into the hyperthermophile range (i.e., Tm≥85° C. with the SYM10ΔΔ, SYM12ΔΔ, SYM13ΔΔ, and Symfoil-4P mutant proteins), the folding cooperativity m value exhibited a modest decline. Auton and Bolen have reported that the summation of transfer free energies from water to osmolyte for a comparison of native- and denatured state models can accurately predict protein folding m values (Auton, M. & Bolen, D. W. (2005). Proc. Natl Acad. Sci. USA, 102, 15065-15068) with the greatest contribution to the magnitude of the folding m value provided by the peptide backbone (and with side chains having a comparatively minor influence). This suggests that a specific tertiary structure has an intrinsic folding m value with comparatively minor modulation in response to amino acid substitution; thus, conservation of tertiary structure is consistent with conservation of folding m value. Applicants note, however, that all mutants in the SD less stable than FGF-1 exhibit a higher folding m value; conversely, all mutants more stable than FGF-1 exhibit a lower folding m value. This effect is relatively subtle but suggests an inverse correlation between thermostability and folding m value, with FGF-1 residing on this continuum (FIG. 18). The origin of this effect may be residual structure in the osmolyte-induced unfolded form as the thermostability increases; this correlation suggests that this may be largely unavoidable. Thus, when a stability screen for SD is utilized, enhanced thermostability is an attainable goal, but maintenance of folding m value may be difficult to achieve. The folding and unfolding kinetic data (FIG. 14) show that stability enhancement for the Symfoil series of proteins was realized through a combination of increased folding as well as decreased unfolding kinetic constants. These results are achieved through native-state stabilization (in comparison to the folding transition state; i.e., $\Delta\Delta G_u$>0) as well as folding transition-state stabilization (in comparison to the denatured state; i.e., $\Delta\Delta G_f$<0; Table 8). Thus, the symmetric primary structure is compatible with both an efficient native structure and folding transition state in terms of thermodynamics and folding kinetics.

The use of a chimera construct to achieve a final symmetric polypeptide (i.e., the Symfoil-1 protein) proved to be a successful and rapid method to complete the SD (while maintaining a foldable, stable polypeptide). Immediately prior to the chimera design, the SD transforms increased the primary structure symmetry from 2% in FGF-1 to 33% in the SYM13ΔΔ mutant. A useful heuristic in undertaking a chimera approach to achieve a symmetric primary structure constraint would be to increase the primary structure symmetry (e.g., by point mutation) to a critical threshold prior to attempting chimera design; in this regard, 33% primary-structure symmetry may be a useful minimum target.

The Symfoil-1 protein contains only 16 of the 20 common amino acids. Notably absent in the primary structure is Ala, known for high α-helical propensity (Argos, P. & Palau, J. (1982). Int. J. Pept. Protein Res. 19, 380-393, Padmanabhan, S. et al. (1990). Nature, 344, 268-270 and Blaber, M. et al. (1993). Science, 260, 1637-1640). The Symfoil β-trefoil architecture is devoid of α-helix and contains only β-strand and reverse-turn secondary structure. Conversely, the Symfoil sequence is comparatively rich in β-branched residues Ile, Thr, and Val that are known to have a high β-strand-forming propensity (Kim, C. A. & Berg, J. M. (1993). Nature, 362, 267-270, Minor, D. L., Jr & Kim, P. S. (1994). Nature, 367, 660-663 and Smith, C. K. et al. (1994). Biochemistry, 33, 5510-5517). The Symfoil-1 protein, involving both a 3-fold symmetric constraint and elimination of a significant subset of amino acids, represents a substantial reduction in sequence complexity in relationship to the FGF-1 protein. While reduced sequence complexity and symmetric primary-structure features are associated with natively unstructured proteins and aggregation (Wootton, J. C. & Federhen, S. (1993). Computers Chem. 17, 149-163, Romero, P. et al. (2001). Proteins, 42, 38-48, Wright, C. F. et al. (2005). Nature, 438, 878-881 and Hoang, T. X. et al. (2006). Proc. Natl Acad. Sci. USA, 103, 6883-6888). Symfoil-1 exhibits enhanced stability and folding properties in comparison to FGF-1 (i.e., no thermal-induced aggregation, reversible two-state denaturation with no biphasic folding, and enhanced thermostability). Therefore, the results show that symmetric sequence design can be compatible with efficient folding and stability, thus providing support for purely symmetric design principles in de novo protein design. The derived Monofoil-4P polypeptide is 66% identical to FGF-1 trefoil-fold 1, 39% identical to trefoil-fold 2, and 11% identical to trefoil-fold 3, but is devoid of known FGF-1 functionality. It is therefore plausible that in FGF-1 the first two trefoil folds provide the majority of the essential structural determinants for folding and stability; correspondingly, elements of heparin- and receptor-binding functionality are known to residue within the third trefoil fold (Blaber, M. et al. (1996). Biochemistry, 35, 2086-2094 and Pantoliano, M. W. et al. (1994). Biochemistry, 33, 10229-10248).

The Monofoil-4P 42-mer polypeptide spontaneously folded as a stable homotrimer recapitulating the β-trefoil architecture. The Difoil-4P 82-mer polypeptide, representing a gene duplication/fusion of the Monofoil-4P peptide, also produced the β-trefoil target architecture (as two complete β-trefoil folds within a homotrimer complex) (Lee, J. & Blaber, M. (2011). Proc. Natl Acad. Sci. USA, 108, 126-130). No evidence of soluble monomeric forms or insoluble aggregates was observed during the purification of either polypeptide; furthermore, no refolding step was utilized in the purification of either polypeptide, and thermal denaturation was essentially reversible. Further work is needed to understand the process of trimeric assembly and whether the Monofoil-4P peptide has any preformed structure prior to oligomerization. Additionally, the oligomeric assemblies formed by both Monofoil-4P and Difoil-4P peptides recapitulate the same degree of symmetry as the parental FGF-1 protein (with no higher-order forms). In contrast to the β-trefoil, the β-propeller fold is one where different copy numbers of each repeating subdomain (e.g., four to eight "blades") are known to exist as an integral whole (Chadhuri I et al. (2008). Proteins, 71, 795-803). A major structural difference is that while the β-trefoil contains a central cooperative hydrophobic corepacking group, the β-propeller architecture can be described as a circularly closed linear-repeat protein where the primary hydrophobic packing is between adjacent repeating elements (and no centralized packing group exists). Thus, whereas an additional repeat might be accommodated with β-propeller type architecture, accommodation of an additional repeat within the β-trefoil fold would require a substantial alteration to the design of the central cooperative core-packing group. Since all known β-trefoil proteins are single polypeptide chains, the Monofoil-4P and Difoil-4P multimeric structures are unique, and despite the obvious entropic penalty, they spontaneously assemble to generate stable β-trefoil architecture. In this regard, the development of the hyperthermostable Symfoil-4P polypeptide may have been critical to the success of the fragmentation step in the SD.

The Monofoil-4P polypeptide is a useful building block for traditional bottom-up hierarchical de novo design; it can assemble as a homotrimer or as a concatenated threefold repeat within a single polypeptide to spontaneously generate a soluble, foldable, thermostable, precisely defined β-trefoil fold. The resulting β-trefoil is functionally benign (i.e., no known FGF-1 function has carried over into the Monofoil-4P polypeptide) yet is thermostable and therefore function competent. Introduction of novel function can proceed via directed or random mutagenesis coupled with a functional selection or screen. In this regard, mutating the Monofoil-4P polypeptide could be utilized to search for 3-fold symmetric compatible function, whereas mutation of the Symfoil-4P polypeptide could explore function enabled by the introduction of asymmetry within the symmetric architecture. Preliminary studies with mix and match of the Monofoil-4P and Difoil-4P polypeptides have shown that heterodimers with 1:1 stoichiometry readily form, recapitulating an intact β-trefoil fold. In this regard, the Difoil-4P polypeptide could serve as a scaffold into which mutant Monofoil-4P type peptides could assemble to create intact soluble β-trefoil proteins with novel functionality.

The top-down SD describes a logical approach that is broadly applicable and is not architecture dependent. What is described in this Example is the sequential targeting of core (transform #1), turn (transform #2), and, finally, secondary-structure (β-strand; transform #3) positions. This logic is, in principle, applicable in the SD of any aqueously soluble symmetric globular protein. Although the β-trefoil contains β-strand secondary structure and no α-helix, it is a straightforward modification of transform #3 to focus instead on α-helix. Each transform was developed by utilizing statistical preferences of amino acids, either conserved residues for the particular architecture (i.e., β-trefoil; transform #1) or conserved residues for the secondary structure (i.e., Asx-Pro-Asx-Gly in β-turns in transform #2 or preferred β-strand residues in transform #3). As with the conceptually related method of retrosynthetic analysis (RA) in the design of organic synthesis strategies (Corey, E. J. & Cheng, X. M. (1989). The Logic of Chemical Synthesis. John Wiley & Sons, Inc., New York), SD of protein architecture follows a specific logic even though the end point is not known a priori; this is the strength of the method, which can provide a useful alternative to bottom-up approaches to de novo protein design.

Symmetric Deconstruction.

Top-down SD is loosely based on principles of RA formalized by Corey and Cheng (Corey, E. J. & Cheng, X. M. (1989). The Logic of Chemical Synthesis. John Wiley & Sons, Inc., New York) for the purpose of efficiently designing synthetic pathways of complex organic molecules. In RA, the target molecule (i.e., desired synthesis product) is considered first, and is conceptually "deconstructed" into increasingly simpler molecules using knowledge of efficient bond synthesis; each deconstruction step is termed a "transform." This process continues until useful precursors for synthesis are identified, at which point an efficient synthetic pathway has been generated. More important, RA begins with no preconceived ideas regarding the best precursor(s) for the synthesis; the method identifies such molecules. In contrast to RA applied to organic synthesis (a conceptual process), SD developed herein is experimental. SD is not concerned with issues of peptide bond synthesis; instead, SD reduces sequence complexity via the progressive application of a symmetric primary-structure constraint, while maintaining foldability, for the purpose of identifying a useful peptide building block for the target architecture. A brief description of the application of SD in support of a specific evolutionary mechanism of the β-trefoil fold has previously been reported (Lee, J. & Blaber, M. (2011). Proc. Natl Acad. Sci. USA, 108, 126-130) here, Applicants provide a detailed biophysical characterization of this process. SD starts with a naturally evolved (i.e., foldable and thermostable) protein that is a member of the target architecture. The peptide motif generated by SD is useful as a building block for subsequent bottom-up hierarchical de novo design of the target architecture.

The target architecture selected for SD was the β-trefoil, a common protein fold that in conceptually idealized form has internal 3-fold rotational symmetry (McLachlan, A. D. (1979). J. Mol. Biol. 133, 557-563 and Murzin, A. G. et al. (1992). J. Mol. Biol. 223, 531-543) (although naturally evolved β-trefoil proteins exhibit substantial asymmetry in their primary and tertiary structures). The β-trefoil "proxy" selected for SD was human FGF-1 (see FIGS. 8A-8C, 9 and 12). In choosing FGF-1, maximum advantage was taken of a comparatively large amount of published mutational data on protein stability and folding. Sequence alignment of the three trefoil-fold subdomains within FGF-1 identifies only a single position sharing identical residues (i.e., Gly29, Gly79, and Gly115). Additionally, each of the three trefoil-fold subdomains exhibit different lengths (due to relative insertions/deletions); thus, SD of FGF-1 requires substantial redesign of both the primary and tertiary structure of the protein. Furthermore, FGF-1 is a weak mesophile as regards thermostability ($\Delta G=21.0$ kJ/mol) (Brych, S. R. et al. (2001). Protein Sci. 12, 2704-2718); thus, mutational change must be generally compatible with folding and stability. The transforms applied in the SD of FGF-1 followed a logic of imposing a cumulative symmetric constraint on core, reverse-turn, and β-strand secondary structure, respectively, by targeted mutagenesis. Symmetric mutations were retained if they were either neutral or favorable to protein stability, folding, and solubility. Such properties are essential for protein function (Soskine, M. & Tawfik, D. S. (2010). Nat. Rev. 11, 572-582) thus, SD includes a screen for function-competent biophysical properties (but no specific functionality). Whenever possible, prior mutational data were utilized in identifying potential symmetric mutations. Sequence comparison between the three trefoil-fold subdomains of FGF-1 was utilized to identify candidate symmetric mutations; for example, if the same residue was present at two out of three symmetry-related positions, mutation to that residue at the third position was typically evaluated. Potential symmetric mutations were analyzed by molecular modeling using FGF-128 or mutant X-ray structures. A description of the individual transforms in SD of FGF-1 follows.

Transform #1: SD of Core Positions.

Previously published work has detailed the development of a series of symmetric core-packing mutations (SYM2-523,24; FIGS. 8A, 8B, and 8C) that systematically introduced a symmetric primary-structure constraint on the central hydrophobic core of FGF-1. Without changes to the FGF-1 tertiary structure, only limited symmetry within the core region was possible without also incurring substantial destabilization (compare SYM5 and SYM6); (Brych, S. R. et al. (2003) Protein Sci. 12, 2704-2718) however, deletion mutations that increased the tertiary-structure symmetry enabled the accommodation of a symmetric and thermostable hydrophobic core (SYM6ΔΔ) (Brych, S. R. et al. (2004). J. Mol. Biol. 344, 769-780). Thus, the SD method included both primary- and tertiary structure symmetric constraint mutations. Production of the SYM8ΔΔ mutant represents essential completion of transform #1, and this mutant was utilized as the starting point for transform #2.

Transform #2: SD of Reverse Turns.

The SYM8ΔΔ mutant was initially modified by the inclusion of two previously described stabilizing point mutations (Lys12Val and Pro134Val) (Dubey, V. K. et al. (2007). J. Mol. Biol. 371, 256-268) and reversion of previously introduced Cys mutations at positions 42 and 130 (due to undesirable thiol reactivity) to produce the SYM9ΔΔ mutant (FIG. 10). The Lys12Val and Pro134Val mutations are located in the adjacent first and last β-strands of the β-barrel of the architecture, respectively. The N- and C-terminus β-strands represent a "discontinuous" β-turn, as the 3-fold symmetry-related positions describe β-turns #4 and #8 (see FIGS. 8A, 8B, 8C, and 12). The break between the N- and C-terminus β-strands describes a region of known structural weakness (Bernett, M. J. et al. (2004). Proteins, 57, 626-634) and the Lys12Val and Pro134Val mutations stabilize these adjacent β-strand interactions (Dubey, V. K. et al. (2007). J. Mol. Biol. 371, 256-268). A His93Gly mutation, located within β-turn #8 and reported to stabilize FGF-1 (Arakawa, T. et al. (1993). Protein Eng. 6, 541-546 and Kim, J., et al. (2003). J. Mol. Biol. 328, 951-961) was introduced into the SYM9ΔΔ mutant to produce the SYM10ΔΔ mutant. This mutation increased the primary-structure symmetry between symmetry-related β-turns #4 and #8. Prior studies of the role of the statistically preferred β-turn motif Asx-Pro-Asx-Gly (SEQ ID NO: 1) at individual β-turns #2, 6, and 10 in FGF-1 indicated a consistently favorable effect on thermostability with the sequence Asn-Xxx-Asp-Gly (where Xxx represents the retained FGF-1 residue at this position) (Lee, J. et al. 2008). J. Mol. Biol. 377, 1251-1264). The canonical Asn-Pro-Asp-Gly (SEQ ID NO: 2) sequence was therefore substituted into the SYM10ΔΔ mutant at each of these symmetry-related β-turns to produce the SYM11ΔΔ mutant (FIG. 10). The SD of β-turn regions was not taken to completion at this stage, and the SYM11ΔΔ mutant was considered a successful "proof of concept" and was utilized as the starting point for transform #3.

Transform #3: SD of β-Strands.

Taking advantage of the Lys12Val mutation (described bove), Applicants introduced an Asn95Val mutation into SYM11ΔΔ resulting in a symmetric (Val) deconstruction of positions 12, 54, and 95 within β-strands 1, 5, and 9, respectively. Similarly, Leu46Val and Glu87Val mutations were introduced, resulting in a further symmetric (Val) constraint within symmetry-related β-strands 4, 8, and 12, respectively. The combination of these mutations resulted in the SYM12ΔΔ mutant (FIG. 11). Ile56Leu and Tyr97Leu mutations (identified as structurally compatible symmetric mutations by manual modeling) were subsequently introduced into the SYM12ΔΔ mutant, increasing the symmetric constraint within β-strands 1, 5 and 9, respectively, and producing the SYM13ΔΔ mutant. The SD of β-strand regions was not taken to completion at this stage, and the SYM13ΔΔ mutant was considered a successful proof of concept.

Completion of transforms #2 and #3 was accomplished simultaneously via a chimera design strategy. The SYM13ΔΔ mutant contained two buried free Cys residues at positions 16 and 83, which were known to substantially limit the functional half-life of FGF-1 via thiol reactivity while in the unfolded and exposed state (Culajay, J. F. et al. (2000). Biochemistry, 39, 7153-7158 and Lee, J. & Blaber, M. (2009). J. Mol. Biol. 393, 113-127). The local packing environment around each of these residues is highly optimized for Cys and intolerant to substitution without significant destabilization (Lee, J. & Blaber, M. (2009). J. Mol. Biol. 393, 128-139). Subsequently, a chimera design was chosen so as to substitute the packing environment surrounding positions Cys16 and Cys83 with the packing environment surrounding the symmetry related non-Cys residues Ser58 and Ile42, respectively. Threading of this chimera sequence onto the SYM6ΔΔ/Phe108Tyr X-ray structure suggested no bad contacts, either within individual trefoil-fold subdomains or, critically, at the subdomain interface(s), with one exception involving residues within symmetry-related β-turns 4, 8 and 12. These turns were therefore designed using a simple (Gly)3 linker sequence. A single Pro residue was retained at position 10 (the initial residue of the first trefoilfold subdomain) to promote solvent accessibility of the preceding N-terminal hexahistidine [(His)6]-FGF-1 (1-10) residue sequence ("Hexahistidine" and "(His)6" disclosed as SEQ ID NO: 3). The resulting chimera sequence was termed "Symfoil-1" (for symmetric β-trefoil protein #1; FIG. 11). The residue numbering of all synthetic mutants was chosen so as to correspond as closely as possible with the numbering of the initial FGF-1 protein.

Transform #4: Stability optimization/symmetric fragmentation. Since the intermediate asymmetric "SYMΔΔ" mutant proteins demonstrated higher stability than Symfoil-1, optimization of Symfoil-1 stability was pursued prior to attempting fragmentation of the repeating peptide motif. Manual inspection of the X-ray structure of Symfoil-1 indicated that symmetry-related residue positions Val46, 87, and 134 (located at the solvent interface at the top of the β-barrel) each contain a "crevice" adjacent to Val $C^{\gamma 2}$, suggesting that an Ile mutation might be accommodated with enhanced van der Waals interactions. Subsequently, Ile mutations were introduced at each of these positions to create the Symfoil-2 variant (FIGS. 13A and 13B). Symmetry-related β-turns 4 and 8 were initially designed to be simple (Gly)3 linkers, although these were considered to be a nonoptimal β-turn solution. "Asn scanning" of positions i (residue 49) through i+3 (residue 52) was performed on β-turn 4 in the Symfoil-2 protein and demonstrated a stability improvement with Asn mutation at the i+2 position. Asn mutations were therefore introduced at symmetry-related positions 51, 92, and 139 of the Symfoil-2 protein to produce Symfoil-3. A Gln40Pro mutation was reported to stabilize the FGF-1 protein (Zakrzewska, M. et al. (2005) J. Mol. Biol. 352, 860-875). Since Gln40 was conserved in Symfoil-3, Pro mutations were introduced at symmetry related positions 40, 81, and 128 of Symfoil-3 to produce Symfoil-4; alternative constructs utilizing either Val or Thr mutations were also introduced at these positions, and these different forms are identified as Symfoil-4T, V, or P mutants, respectively. The Symfoil-4P mutant (the most stable Symfoil variant) was selected as the starting point for the symmetric fragmentation of the 42-residue repeating polypeptide motif. Dimer and monomer trefoil-fold subdomains were constructed by mutagenesis of Symfoil-4P; the resulting monomeric and dimeric trefoil-fold polypeptides are referred to as Monofoil-4P and Difoil-4P, respectively (for monomeric trefoil fold and dimeric trefoil fold, respectively).

Mutagenesis and Protein Purification.

Construction of all the SYMΔΔ mutants utilized a synthetic gene for the 140-amino-acid form of human FGF-1 (Blaber, M. et al. (1996). Biochemistry, 35, 2086-2094, Gimenez-Gallego, G. et al. (1986). Biochem. Biophys. Res. Commun. 128, 611-617, Linemeyer, D. L. et al. (1990). Growth Factors, 3, 287-298 and Ortega, S. et al. (1991). J. Biol. Chem. 266, 5842-5846) containing an additional amino-terminal $(His)_6$ tag (SEQ ID NO: 3) as previously described (Brych, S. R. et al. (2001). Protein Sci. 10, 2587-2599). The QuikChange™ site-directed mutagenesis protocol (Agilent Technologies, Santa Clara, Calif.) was used to introduce all mutations, which were confirmed by nucleic acid sequence analysis (Biomolecular Analysis Synthesis and Sequencing Laboratory, Florida State University). Construction of the Symfoil-1 protein involved complete gene synthesis utilizing unique codons at symmetry-related positions such that these could be individually targeted during subsequent mutagenesis. The Monofoil-4P and Difoil-4P genes were generated by mutation of the Symfoil-4P gene to introduce a stop codon at position Glu53 or Glu94, respectively. Additionally, for crystallization trials of Monofoil-4P and Difoil-4P polypeptides, the codons for N-terminus residues 1-10 were deleted (i.e., the N-terminus $(His)_6$-tag (SEQ ID NO: 3) was followed immediately by residue position 11 of the FGF-1 numbering scheme). Expression and purification of recombinant proteins followed previously published procedures (Brych, S. R. et al. (2001). Protein Sci. 10, 2587-2599) and utilized Ni-NTA chelation and Superdex 75 size-exclusion chromatography (GE Healthcare, Piscataway, N.J.). Purified protein was exchanged into crystallization buffer [50 mM sodium phosphate, 0.1 M NaCl, 10 mM $(NH_4)_2SO_4$, 2 mM dithiothreitol (DTT), pH 7.5] for crystallization studies (with DTT omitted for all Symfoil protein variants) or ADA buffer [20 mM N-(2-acetamido)iminodiacetic acid (ADA), 0.1 M NaCl, 2 mM DTT, pH 6.6] for biophysical studies (with DTT omitted for all Symfoil protein variants). An extinction coefficient of $E_{280}$ nm (0.1%, 1 cm)=1.26 (Zazo, M. et al. (1992). Gene, 113, 231-238 and Tsai, P. K. et al. (1993). Pharm. Res. 10, 649-659) was used to determine protein concentration for FGF-1. Due to the variation in number of Trp, Tyr, and Cys residues, the extinction coefficient for all mutant forms was determined by the method of Gill and von Hippel (Gill, S. C. & von Hippel, P. H. (1989). Anal. Biochem. 182, 319-326).

Isothermal Equilibrium Denaturation.

Isothermal equilibrium denaturation by GuHCl was performed as previously described (Blaber, S. I. et al. (1999). Biophys. J. 77, 470-477) with either fluorescence or circular dichroism (CD) as the spectroscopic probe. FGF-1 unfolding monitored by CD spectroscopy exhibits excellent agreement with results obtained by fluorescence spectroscopy and is a useful alternative spectroscopic probe in cases where fluorescence cannot be utilized.59 FGF-1 contains a single buried Trp residue at position 107, and although this exhibits atypical native state quenching, it is nonetheless useful as a spectroscopic probe of unfolding. This native-state quenching appears due to an adjacent Pro121 residue that is deleted in all the SYMΔΔ mutants; thus, for these mutants there is little discrimination between the native- and denatured-state fluorescence, and the unfolding was followed by CD signal. All Symfoil mutants delete Trp107, and their fluorescence signal is largely contributed by Tyr residues at positions 22, 64, and 108. Unfolding was followed by both fluorescence and CD, which were found to be in excellent agreement (similarly for Monofoil-4P and Difoil-4P polypeptides); subsequently, all reported values for Symfoil mutants are fluorescence data. Fluorescence data were collected on a Cary Eclipse fluorescence spectrophotometer (Varian Inc., Palo Alto, Calif.) equipped with a Pelletier controlled-temperature regulator at 298 K and using a 1.0-cm path-length cuvette. Protein samples (5.0 μM) were equilibrated in ADA buffer at 298 K in 0.1M increments of GuHCl. For unfolding analysis monitored by CD, 25 μM protein samples were equilibrated in ADA buffer at 298 K in 0.1 M increments of GuHCl. CD data were collected on a Jasco model 815 CD spectrophotometer (Jasco Inc, Easton, Md.) equipped with a Pelletier controlled-temperature regulator at 298 K and using a 1-mm path-length cuvette. Both fluorescence and CD data were analyzed with the general-purpose nonlinear least-squares fitting programDataFit (Oakdale Engineering, Oakdale, Pa.) implementing a six-parameter, two-state model 71 as previously described.22 The effect of a given mutation on the stability of the protein (ΔΔG) was calculated by taking the difference between the midpoint of denaturation (Cm value) for reference and mutant proteins and multiplying by the average of the m values, as described by Pace and Scholtz (Pace, C. N. & Scholtz, J. M. (1997). ProteinStructure: a Practical Approach (Creighton, T. E., ed.), pp. 299-321, Oxford University Press, Oxford) and where a negative value indicates the mutation is stabilizing in relationship to the reference protein. In the case of Monofoil-4P and Difoil-4P proteins, the data were analyzed with a trimer-tomonomer isothermal equilibrium denaturation model (Backmann, J. et al. (1998). J. Mol. Biol. 284, 817-833 and Jelesarov, I. & Lu, M. (2001). J. Mol. Biol. 307, 637-656) where subunit dissociation occurs simultaneously with two-state unfolding:

$$N_3 \Leftrightarrow 3D \quad (1)$$

and the equilibrium dissociation constant $K_D$ is expressed as:

$$K_D = \frac{27C_t^2 F_D^3}{1-F_D} \quad (2)$$

where $C_t$ is the molar concentration of trimer form and $F_D$ is the fraction of denatured monomer. See Backmann, J. et al. (1998). J. Mol. Biol. 284, 817-833 for details of the derivation of the function describing the experimental spectroscopic data in terms of the fitted thermodynamic parameters.

Differential Scanning Calorimetry.

All DSC data were collected on a VP-DSC microcalorimeter (GE Healthcare) as previously described (Blaber, S. I. et al. (1999). Biophys. J. 77, 470-477). Briefly, 40 μM protein samples were equilibrated at 298 K in ADA buffer without DTT and in the presence of varying concentrations of GuHCl. A scan rate of 15 K/h was used for all proteins to meet the equilibrium assumption of the thermodynamic model. Molar heat capacity data were analyzed with the DSCfit software package (Grek, S. B. et al. (2001). Protein Pept. Lett. 8, 429-436). The Monofoil-4P and Difoil-4P mutants were analyzed with a trimer-to-monomer thermal denaturation model (Backmann, J. et al. (1998). J. Mol. Biol. 284, 817-833 and Jelesarov, I. & Lu, M. (2001). J. Mol. Biol. 307, 637-656) and implemented with the DataFit nonlinear least-squares fit software package (Oakdale Engineering) (see Backmann, J. et al. (1998). J. Mol. Biol. 284, 817-833 for details of the derivation of the function describing the experimental molar heat capacity data in terms of the fitted thermodynamic parameters).

Folding/Unfolding Kinetic Analysis.

Folding and unfolding kinetic data followed previously described methods (Kim, J., et al. (2003). J. Mol. Biol. 328, 951-961). Briefly, denatured protein samples for folding kinetics measurements were prepared by overnight dialysis against ADA buffer containing 2.5-5.0 M GuHCl. All folding kinetic data were collected with an Applied Photophysics SX20 stopped-flow system (Applied Photophysics Ltd., Surrey, UK) at 298 K. Folding was initiated by a 1:10 dilution of 20 µM denatured protein into ADA buffer with denaturant concentrations varying in increments of 0.05 or 0.1 M up to the midpoint of denaturation, as determined by isothermal equilibrium denaturation measurements. The data collection strategy was designed to span approximately five half-lives or >97% of the expected fluorescence signal change between the fully denatured and native states. For unfolding kinetics measurements due to the comparatively slower kinetics, unfolding kinetics measurements were performed by manual mixing. Protein samples (~20 µM) were dialyzed against ADA buffer overnight at 298 K. Unfolding was initiated by a 1:10 dilution into ADA buffer with a final GuHCl concentration of 1.5-7.5 M in 0.2 M increments. All unfolding data were collected with a Varian Eclipse fluorescence spectrophotometer equipped with a Pelletier controlled-temperature unit at 298 K. Data collection times for each protein were designed so as to quantify the fluorescence signal over three to four half lives or N93% of the total expected amplitude. The kinetic rates and amplitudes versus denaturant concentration were calculated from the time-dependent change in fluorescence with a single-exponential model. Folding and unfolding rate constant data were fit to a global function describing the contribution of both rate constants to the observed kinetics as a function of denaturant as described by Fersht, A. R. (1999). Kinetics of Protein Folding. Structure and Mechanism in Protein Science. W. H. Freeman and Co., New York.

X-Ray Crystallization Studies.

Purified mutant protein in crystallization buffer was concentrated to 9-15 mg/ml, and crystal screening was performed with either the hanging-drop or sitting-drop vapor diffusion method at room temperature. Diffraction quality crystals of a Phe108Tyr mutation of the SYM6ΔΔ protein grew in 1 week from vapor diffusion against 0.2M magnesium formate. Crystals were mounted with Hampton Research nylon mounted cryoturns and cryocooled in a stream of gaseous nitrogen at 100 K. Diffraction data were collected at the Southeast Regional Collaborative Access Team (SET-CAT) 22-BM beam line ($\lambda$=1.00 Å) at the Advanced Photon Source, Argonne National Laboratory, using a MarCCD 300 detector (Mar USA, Evanston, Ill.). A single-crystal diffraction data set was collected, and diffraction data were indexed, integrated, and scaled with the DENZO or HKL2000 software package (Otwinowski, Z. (1993). Proceedings of the CCP4 Study Weekend: Data Collection and Processing. SERC Daresbury Laboratory, England and Otwinowski, Z. & Minor, W. (1997). Methods Enzymol. 276, 307-326). Molecular replacement and refinement utilized the PHENIX software package (Zwart, P. H. et al. (2008). Methods Mol. Biol. 426, 419-435) with 5% of the data in the reflection files set aside for Rfree calculations (Brunger, A. T. (1992). Nature, 355, 472-475). His-tagged FGF-1 (PDB code 1JQZ) was used as the search model in molecular replacement for the SYM6ΔΔ/Phe108Tyr mutant. Model building and visualization utilized the COOT molecular graphics software (Emsley, P. & Cowtan, K. (2004). Acta Crystallogr., Sect. D: Biol. Crystallogr. 60, 2126-2132).

SPR Studies of FGFR-1c Binding.

FGF-1 and mutant proteins were immobilized as the "ligand" on the SPR sensor chip, and the extracellular domain of human FGFR-1c was used as the soluble "analyte" in all studies. Recombinant FGFR-1c protein was expressed and purified from an insect cell-Baculovirus system as previously described (Lee, J. et al. (2009). Acta Crystallogr., Sect. F. 65, 1097-1104). The FGFR-1c recombinant protein contains the ligand-binding immunoglobulin-like domains D2, D3, and interconnecting linker (residues 131 to 365) and includes an N-terminal His tag for purification purposes. Prior to SPR analysis, the purified FGFR was dialyzed against HBS-EP+ buffer [10 mM Hepes, 150 mM NaCl, 3 mM EDTA (ethylenediaminetetraacetic acid), 0.005% (v/v) surfactant P20, pH 7.4], and 1:2 serial dilutions spanning a concentration range of 256-1.0 nM were made in 1×HBS-EP+ buffer; additionally, the FGF-1 and mutant proteins were passed over a HiLoad Superdex 75 26/60 size-exclusion column (GE Healthcare) to ensure a monodisperse sample and then diluted to 1-10 µg/ml in 10 mM Mes buffer (pH 6.0). The sensor chip was prepared by immobilizing FGF-1 or mutant protein on a Series S Sensor Chip CM5 (GE Healthcare, Uppsala, Sweden) by covalent amine coupling following the manufacturer's suggested protocol. Chip sample surfaces were prepared with a target surface density of ~50 RU. The reference cell surface was prepared under identical conditions with only buffer injections. A surface stability test and mass transfer control experiment were performed to optimize the conditions for interaction kinetics analyses. SPR data were collected at 25° C. on a Biacore T-100 instrument (GE Healthcare). The association/dissociation phase was measured by flowing 0-256 nM FGFR-1c analyte over the FGF-1/mutant protein CM5 Sensor Chip at a flow rate of 75 µl/min for 280 s. At the end of each sample injection, HBS-EP+ buffer was passed over the sensor chip at the same flow rate for 400 s to monitor the dissociation phase. NaCl (2.5 M) was injected at 50 µl/min for 120 s to fully regenerate the sensor surface. The control flow cell response was subtracted from the ligand sample cell for each receptor injection; the 0 M concentration sensorgram values were subsequently subtracted from the analyte runs, and the resulting sensorgrams were analyzed with the Biacore T100 Evaluation v2.0 software package (GE Healthcare). Association ($k_a$) and dissociation ($k_d$) rate constants were determined by fitting with the "bivalent analyte" model, based on the known X-ray structure of human FGF-1 in complex with FGFR-1c (PDB code 1EVT) (Plotnikov, A. N., et al. (2000). Cell, 101, 413-424).

3T3 Fibroblast Mitogenic Assays.

Purified protein was equilibrated in TBS buffer [0.14 M NaCl, 5.1 mM KCl, 0.7 mM $Na_2HPO_4$, and 24.8 mM Tris base (pH 7.4)], and assay of the mitogenic activity toward 3T3 fibroblasts was performed as previously described (Brych, S. R. et al. (2004). J. Mol. Biol. 344, 769-780). Briefly, NIH 3T3 fibroblasts were plated in Dulbecco's modified Eagle's medium (Invitrogen, Carlsbad, Calif.) supplemented with 0.5% (v/v) newborn calf serum (Sigma-Aldrich Corp., St. Louis, Mo.) for 48 h at 37° C. with 5%

(v/v) CO$_2$. The quiescent serum-starved cells were stimulated with fresh medium supplemented with FGF-1 or mutant protein (0-10 μg/ml) and incubated for an additional 48 h. After this incubation period, the cells were counted with a hemacytometer (Hausser Scientific, Horsham, Pa.). The protein concentration yielding one half maximal cell density (EC50 value) was used for quantitative comparison of functional mitogenic activity.

ITC Tris-Binding Studies.

All ITC data were collected on a VP-ITC microcalorimeter (MicroCal LLC, Northampton, Mass.). Titrations were performed at 298 K, and all samples were equilibrated in 50 mM sodium phosphate and 0.1M NaCl (pH 8.0) buffer. All samples were filtered and degassed for 10 min prior to loading. Symfoil-2 (200 μM) was titrated with 20 mM Tris; each injection was performed over 12 s with a post injection equilibration period of 240 s. The samples were titrated against 40 injections at 6 μl per injection of Tris. The titration curves were fit with the manufacturer's software (MicroCal Origin) employing a model with a single ligand-binding site. The Symfoil-2 protein was selected for titration studies due to quantity of protein available and the shared Tris-binding property observed among the set of Symfoil mutant proteins. Fitting of the ITC data, while allowing the stoichiometric parameter n to float, did not result in convergence; however, since the X-ray data were unambiguous in showing a 1:1 protein-Tris complex, the stoichiometric n parameter was fixed to 1.0, thus enabling fitting convergence.

Protease-Resistance Studies.

FGF-1 and mutant proteins (0.025 mM) were incubated with trypsin (Promega, Madison, Wis.) (0.25 μM; for 100:1 molar ratio, respectively) in TBS buffer at 37° C. to evaluate resistance to proteolysis. Time points were taken at various intervals (spanning minutes to days, depending on the particular mutant) and added to SDS sample buffer and immediately incubated at 95° C. for 5 min to halt the digestion reaction. Samples were resolved on 16.5% Tricine SDS-PAGE visualized with Coomassie Brilliant Blue staining. The stained gels were scanned and the amount of intact protein was quantified with UN-SCAN-IT densitometry software (Silk Scientific, Orem, Utah).

PDB Accession Numbers.

Model coordinates for the refined SYM6ΔΔ/Phe108Tyr structure have been deposited in the PDB with code 3O3Q. Crystal structures of the Symfoil-1, Symfoil-2, Symfoil-4T, -4V, -4P, Monofoil-4P and Difoil-4P proteins have previously been reported (Lee, J. & Blaber, M. (2011). Proc. Natl Acad. Sci. USA, 108, 126-130).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for developing a polypeptide comprising:
   (a) constructing a set of intermediary mutants by introducing mutations via mutagenesis to fibroblast growth factor-1 (FGF-1) at symmetry-related positions within each of three β-trefoil fold subdomains of a β-trefoil architecture within FGF-1;
   (b) screening the set of intermediary mutants to identify selected mutations that are either neutral or favorable to protein folding, stability and solubility;

(c) constructing a subsequent set of intermediary mutants by introducing mutations via mutagenesis at symmetry-related positions within each of three β-trefoil fold subdomains of a β-trefoil architecture within each intermediary mutant of the subsequent set of intermediary mutants;

(d) repeating steps (b) and (c) until a stable symmetric β-trefoil mutant is produced, wherein the stable symmetric β-trefoil mutant is soluble and has three repeating β-trefoil fold subdomains in which the amino acid sequence of each of the three repeating β-trefoil fold subdomains is identical; and (e) synthesizing in vitro a polypeptide from the stable symmetric β-trefoil mutant, wherein the polypeptide has an amino acid sequence of one of the three repeating β-trefoil fold subdomains;

wherein each intermediary mutant of the subsequent set of intermediary mutants combines the mutations that are identified as either neutral or favorable to protein solubility, folding, or thermostability in (b); and wherein the polypeptide is capable of spontaneously assembling in solution as a soluble homotrimer with a thermostable β-trefoil architecture.

2. The method of claim 1, wherein the intermediary mutants are purified and/or crystallized for analyzing and comparing protein solubility, folding and thermostability.

3. The method of claim 1, wherein mutations in each of the intermediary mutants comprise residue substitutions and/or deletions.

4. The method of claim 1, wherein mutations in each of the intermediary mutants reside within a foldable sequence space.

5. The method of claim 1, wherein the β-trefoil architecture comprises a hydrophobic core, reverse-turns, and β-strands secondary structures; and wherein mutations at symmetry-related positions reside within the hydrophobic core, reverse-turns, and β-strands secondary structures of the β-trefoil architecture.

6. The method of claim 5, wherein mutations at symmetry-related positions within each of three β-trefoil fold subdomains are introduced sequentially within the hydrophobic core, reverse-turns, and β-strands secondary structures of the β-trefoil fold architecture, respectively.

7. The method of claim 1, wherein the stable symmetric β-trefoil mutant comprises Symfoil-1.

8. The method of claim 1, wherein the stable symmetric β-trefoil mutant comprises Symfoil-2.

9. The method of claim 1, wherein the stable symmetric β-trefoil mutant comprises Symfoil-3.

10. The method of claim 1, wherein the stable symmetric β-trefoil mutant comprises Symfoil-4T, Symfoil-4V, or Symfoil-4P, and wherein Symfoil-4T, Symfoil-4V, or Symfoil-4P each comprises three repeating subdomains with three identical repeating amino acid sequences, respectively.

11. The method of claim 10, wherein Monofoil-4P is generated by introducing via mutagenesis a stop codon at position Glu53 within Symfoil-4P, wherein Monofoil-4P is a 42-mer polypeptide, and wherein Monofoil-4P spontaneously assembles in solution as a soluble homotrimer with a thermostable β-trefoil architecture.

12. The method of claim 10, wherein Difoil-4P is generated by introducing via mutagenesis a stop codon at position Glu94 within Symfoil-4P, wherein Difoil-4P represents a gene duplication of Monofoil-4P, and wherein Difoil-4P spontaneously assembles in solution as a soluble homotrimer with two intact β-trefoil folds.

13. A method for developing a polypeptide comprising:

(a) constructing a set of intermediary mutants by introducing mutations via mutagenesis to a naturally evolved foldable protein having symmetric fold subdomains within a target symmetric architecture, wherein the mutations are introduced at symmetry-related positions within each of the symmetric fold subdomains;

(b) screening the set of intermediary mutants to identify selected mutations that are either neutral or favorable to protein folding, stability and solubility;

(c) constructing a subsequent set of intermediary mutants by introducing mutations via mutagenesis at symmetry-related positions within each of the symmetric fold subdomains of the target symmetric architecture within each intermediary mutant of the subsequent set of intermediary mutants, wherein each intermediary mutant of the subsequent set of intermediary mutants combines the mutations that are identified as either neutral or favorable to protein solubility, folding, or thermostability in (b);

(d) repeating steps (b) and (c) until a stable mutant having the 1 target symmetric architecture is produced, wherein the stable mutant having the target symmetric architecture is soluble and contains repeating subdomains in which the amino acid sequence of each of the repeating subdomains is identical; and (e) synthesizing in vitro a polypeptide from the stable mutant having the target symmetric architecture, wherein the polypeptide has an amino acid sequence of one of the repeating subdomains;

wherein the polypeptide is capable of spontaneously assembling in solution as a soluble homomultimer with the target symmetric architecture.

14. The method of claim 13, wherein the intermediary mutants are purified and/or crystallized for analyzing and comparing protein solubility, folding and thermostability.

15. The method of claim 13, wherein mutations in each of the intermediary mutants comprise residue substitutions and/or deletions.

16. The method of claim 13, wherein mutations in each of the intermediary mutants reside within a foldable sequence space.

17. The method of claim 13, wherein the naturally evolved foldable protein comprises structural symmetries higher than 2-fold.

18. The method of claim 13, wherein the naturally evolved foldable protein comprises 2-fold structural symmetries.

19. The method of claim 13, wherein the naturally evolved foldable protein comprises a symmetric β-trefoil architecture, and wherein the symmetric β-trefoil architecture comprises a hydrophobic core, reverse-turns, and β-strands secondary structures.

20. The method of claim 19, wherein mutations at symmetry-related positions within each of the symmetric fold subdomains reside within the hydrophobic core, reverse-turns, and β-strands secondary structures of the symmetric β-trefoil architecture.

21. The method of claim 20, wherein mutations at symmetry-related positions within each of the symmetric fold subdomains are introduced sequentially within the hydrophobic core, reverse-turns, and β-strands secondary structures of the symmetric β-trefoil architecture, respectively.

* * * * *

SEQUENCE LISTING

```
<160> NUMBER OF SEQ ID NOS: 28

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asx Pro Asx Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Pro Asp Gly
1

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5
```

```
<210> SEQ ID NO 4
<211> LENGTH: 130
<212> TYPE: PRT
<213> ORGANISM: Homo sapiens

<400> SEQUENCE: 4

Pro Lys Leu Leu Tyr Cys Ser Asn Gly Gly His Phe Leu Arg Ile Leu
1               5                   10                  15

Pro Asp Gly Thr Val Asp Gly Thr Arg Asp Arg Ser Asp Gly His Ile
            20                  25                  30

Gly Leu Gly Leu Ser Ala Glu Ser Val Gly Glu Val Tyr Ile Lys Ser
        35                  40                  45

Thr Glu Thr Gly Gly Tyr Leu Ala Met Asp Thr Asp Gly Leu Leu Tyr
    50                  55                  60

Gly Ser Gly Thr Pro Asn Glu Glu Cys Leu Phe Leu Glu Arg Leu Glu
65                  70                  75                  80

Glu Asn His Tyr Asn Thr Tyr Ile Ser Lys Lys His Ala Glu Lys Asn
                85                  90                  95

Trp Phe Val Gly Leu Lys Lys Asn Gly Ser Cys Lys Arg Gly Pro Arg
            100                 105                 110

Thr His Tyr Gly Gly Lys Ala Ile Leu Phe Leu Pro Leu Pro Val Ser
        115                 120                 125

Ser Asp
    130

<210> SEQ ID NO 5
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Val Leu Leu Lys Ser Thr Glu Thr Gly Gln Tyr Leu Arg Ile Asn
1               5                   10                  15

Pro Asp Gly Thr Val Asp Gly Thr Arg Asp Arg Ser Asp Pro His Ile
            20                  25                  30

Gln Phe Gln Ile Ser Pro Glu Gly Asn Gly Glu Val Leu Leu Lys Ser
        35                  40                  45

Thr Glu Thr Gly Gln Tyr Leu Arg Ile Asn Pro Asp Gln Thr Val Asp
    50                  55                  60

Gly Thr Arg Asp Arg Ser Asp Pro His Ile Gln Phe Gln Ile Ser Pro
65                  70                  75                  80

Glu Gly Asn Gly Glu Val Leu Leu Lys Ser Thr Glu Thr Gly Gln Tyr
                85                  90                  95

Leu Arg Ile Asn Pro Asp Gly Thr Val Asp Gly Thr Arg Asp Arg Ser
            100                 105                 110

Asp Pro His Ile Gln Phe Gln Ile Ser Pro Glu Gly Asn Gly
        115                 120                 125

<210> SEQ ID NO 6
<211> LENGTH: 130
<212> TYPE: PRT
<213> ORGANISM: Homo sapiens

<400> SEQUENCE: 6
```

```
Pro Lys Leu Leu Tyr Cys Ser Asn Gly Gly His Phe Leu Arg Ile Leu
1               5                   10                  15

Pro Asp Gly Thr Val Asp Gly Thr Arg Asp Arg Ser Asp Gln His Ile
            20                  25                  30

Gln Leu Gln Leu Ser Ala Glu Ser Val Gly Glu Val Tyr Ile Lys Ser
        35                  40                  45

Thr Glu Thr Gly Gln Tyr Leu Ala Met Asp Thr Asp Gly Leu Leu Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Ala Glu Lys Asn
                85                  90                  95

Trp Phe Val Gly Leu Lys Lys Asn Gly Ser Cys Lys Arg Gly Pro Arg
            100                 105                 110

Thr His Tyr Gly Gln Lys Ala Ile Leu Phe Leu Pro Leu Pro Val Ser
        115                 120                 125

Ser Asp
    130

<210> SEQ ID NO 7
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Lys Leu Leu Tyr Cys Ser Asn Gly Gly His Phe Leu Arg Ile Leu
1               5                   10                  15

Pro Asp Gly Thr Val Asp Gly Thr Arg Asp Arg Ser Asp Gln His Ile
            20                  25                  30

Gln Leu Gln Leu Ser Ala Glu Ser Val Gly Glu Val Tyr Ile Lys Ser
        35                  40                  45

Thr Glu Thr Gly Gln Tyr Leu Ala Met Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Ala Glu Lys Asn
                85                  90                  95

Trp Phe Leu Gly Leu Lys Lys Asn Gly Ser Cys Lys Arg Gly Pro Arg
            100                 105                 110

Thr His Tyr Gly Gln Lys Ala Ile Leu Phe Leu Pro Leu Pro Val Ser
        115                 120                 125

Ser Asp
    130

<210> SEQ ID NO 8
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Pro Lys Leu Leu Tyr Cys Ser Asn Gly Gly His Phe Leu Arg Ile Leu
1               5                   10                  15
```

```
Pro Asp Gly Thr Val Asp Gly Thr Arg Asp Arg Ser Asp Gln His Ile
            20                  25                  30

Gln Phe Gln Leu Ser Ala Glu Ser Val Gly Glu Val Tyr Ile Lys Ser
        35                  40                  45

Thr Glu Thr Gly Gln Tyr Leu Ala Met Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Ala Glu Lys Asn
                85                  90                  95

Trp Phe Leu Gly Leu Lys Lys Asn Gly Ser Cys Lys Arg Gly Pro Arg
            100                 105                 110

Thr His Tyr Gly Gln Lys Ala Ile Leu Phe Leu Pro Leu Pro Val Ser
        115                 120                 125

Ser Asp
    130

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Lys Leu Leu Tyr Cys Ser Asn Gly Gly His Phe Leu Arg Ile Leu
1               5                   10                  15

Pro Asp Gly Thr Val Asp Gly Thr Arg Asp Arg Ser Asp Gln His Ile
            20                  25                  30

Gln Phe Gln Leu Ser Ala Glu Ser Val Gly Glu Val Tyr Ile Lys Ser
        35                  40                  45

Thr Glu Thr Gly Gln Tyr Leu Ala Met Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Ala Glu Lys Asn
                85                  90                  95

Trp Phe Leu Gly Leu Lys Lys Asn Gly Ser Val Lys Arg Gly Pro Arg
            100                 105                 110

Thr His Tyr Gly Gln Lys Ala Ile Leu Phe Leu Pro Leu Pro Val Ser
        115                 120                 125

Ser Asp
    130

<210> SEQ ID NO 10
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Pro Lys Leu Leu Tyr Cys Ser Asn Gly Gly His Phe Leu Arg Ile Leu
1               5                   10                  15

Pro Asp Gly Thr Val Asp Gly Thr Arg Asp Arg Ser Asp Gln His Ile
            20                  25                  30
```

```
Gln Phe Gln Leu Ser Ala Glu Ser Val Gly Glu Val Tyr Ile Lys Ser
            35                  40                  45

Thr Glu Thr Gly Gln Tyr Leu Ala Met Asp Thr Asp Gly Leu Val Tyr
 50                  55                  60

Gly Ser Gln Thr Pro Asn Glu Glu Cys Leu Phe Leu Glu Arg Leu Glu
 65                  70                  75                  80

Glu Asn His Tyr Asn Thr Tyr Ile Ser Lys Lys His Ala Glu Lys Asn
                 85                  90                  95

Trp Phe Leu Gly Ile Lys Lys Asn Gly Ser Val Lys Arg Gly Pro Arg
                100                 105                 110

Thr His Tyr Gly Gln Lys Ala Ile Leu Phe Leu Pro Leu Pro Val Ser
                115                 120                 125

Ser Asp
    130

<210> SEQ ID NO 11
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Lys Leu Leu Tyr Cys Ser Asn Gly Gly His Phe Leu Arg Ile Leu
 1               5                  10                  15

Pro Asp Gly Thr Val Asp Gly Thr Arg Asp Arg Ser Asp Gln His Ile
                20                  25                  30

Gln Phe Gln Leu Ser Ala Glu Ser Val Gly Glu Val Tyr Ile Lys Ser
            35                  40                  45

Thr Glu Thr Gly Gln Tyr Leu Ala Ile Asp Thr Asp Gly Leu Val Tyr
 50                  55                  60

Gly Ser Gln Thr Pro Asn Glu Glu Cys Leu Phe Leu Glu Arg Leu Glu
 65                  70                  75                  80

Glu Asn His Tyr Asn Thr Tyr Ile Ser Lys Lys His Ala Glu Lys Asn
                 85                  90                  95

Trp Phe Leu Gly Ile Lys Lys Asn Gly Ser Val Lys Arg Gly Pro Arg
                100                 105                 110

Thr His Tyr Gly Gln Lys Ala Ile Leu Phe Leu Pro Leu Pro Val Ser
                115                 120                 125

Ser Asp
    130

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Pro Lys Leu Leu Tyr Cys Ser Asn Gly Gly His Phe Leu Arg Ile Leu
 1               5                  10                  15

Pro Asp Gly Thr Val Asp Gly Thr Arg Asp Arg Ser Asp Gln His Ile
                20                  25                  30

Gln Phe Gln Leu Ser Ala Glu Ser Val Gly Glu Val Tyr Ile Lys Ser
            35                  40                  45
```

```
Thr Glu Thr Gly Gln Tyr Leu Ala Ile Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Gly Trp Phe Leu
                85                  90                  95

Gly Ile Lys Lys Asn Gly Ser Val Lys Gly Thr His Tyr Gly Gln Lys
                100                 105                 110

Ala Ile Leu Phe Leu Pro Leu Pro Val Ser Ser Asp
        115                 120

<210> SEQ ID NO 13
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Pro Lys Leu Leu Tyr Cys Ser Asn Gly Gly His Tyr Leu Arg Ile Leu
1               5                   10                  15

Pro Asp Gly Thr Val Asp Gly Thr Arg Asp Arg Ser Asp Gln His Ile
                20                  25                  30

Gln Phe Gln Leu Ser Ala Glu Ser Val Gly Glu Val Tyr Ile Lys Ser
            35                  40                  45

Thr Glu Thr Gly Gln Tyr Leu Ala Ile Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Gly Trp Tyr Leu
                85                  90                  95

Gly Ile Lys Lys Asn Gly Ser Val Lys Gly Thr His Tyr Gly Gln Lys
                100                 105                 110

Ala Ile Leu Phe Leu Pro Leu Pro Val Ser Ser Asp
        115                 120

<210> SEQ ID NO 14
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Pro Lys Leu Leu Tyr Cys Ser Asn Gly Gly His Tyr Leu Arg Ile Leu
1               5                   10                  15

Pro Asp Gly Thr Val Asp Gly Thr Arg Asp Arg Ser Asp Gln His Cys
                20                  25                  30

Gln Phe Gln Leu Ser Ala Glu Ser Val Gly Glu Val Tyr Ile Lys Ser
            35                  40                  45

Thr Glu Thr Gly Gln Tyr Leu Ala Ile Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Gly Trp Tyr Leu
                85                  90                  95
```

-continued

Gly Ile Lys Lys Asn Gly Ser Val Lys Gly Thr His Tyr Gly Gln Lys
            100                 105                 110

Ala Cys Leu Phe Leu Pro Leu Pro Val Ser Ser Asp
        115                 120

<210> SEQ ID NO 15
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Lys Leu Leu Tyr Cys Ser Asn Gly Gly His Tyr Leu Arg Ile Leu
1               5                   10                  15

Pro Asp Gly Thr Val Asp Gly Thr Arg Asp Arg Ser Asp Gln His Cys
            20                  25                  30

Gln Phe Gln Leu Ser Ala Glu Ser Val Gly Glu Val Tyr Ile Lys Ser
        35                  40                  45

Thr Glu Thr Gly Gln Tyr Leu Ala Ile Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Gly Trp Tyr Leu
                85                  90                  95

Gly Ile Lys Lys Asn Gly Ser Val Lys Gly Thr His Tyr Gly Gln Lys
            100                 105                 110

Ala Cys Leu Phe Leu Pro Leu Pro Val Ser Ser Asp
        115                 120

<210> SEQ ID NO 16
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Val Leu Leu Tyr Cys Ser Asn Gly Gly His Tyr Leu Arg Ile Leu
1               5                   10                  15

Pro Asp Gly Thr Val Asp Gly Thr Arg Asp Arg Ser Asp Gln His Ile
            20                  25                  30

Gln Phe Gln Leu Ser Ala Glu Ser Val Gly Glu Val Tyr Ile Lys Ser
        35                  40                  45

Thr Glu Thr Gly Gln Tyr Leu Ala Ile Asp Thr Asp Gly Leu Val Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Gly Trp Tyr Leu
                85                  90                  95

Gly Ile Lys Lys Asn Gly Ser Val Lys Gly Thr His Tyr Gly Gln Lys
            100                 105                 110

Ala Ile Leu Phe Leu Val Leu Pro Val Ser Ser Asp
        115                 120

<210> SEQ ID NO 17
<211> LENGTH: 124

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Pro Val Leu Leu Tyr Cys Ser Asn Gly Gly His Tyr Leu Arg Ile Leu
1               5                   10                  15

Pro Asp Gly Thr Val Asp Gly Thr Arg Asp Arg Ser Asp Gln His Ile
            20                  25                  30

Gln Phe Gln Leu Ser Ala Glu Ser Val Gly Glu Val Tyr Ile Lys Ser
        35                  40                  45

Thr Glu Thr Gly Gln Tyr Leu Ala Ile Asp Thr Asp Gly Leu Val Tyr
50                  55                  60

Gly Ser Gln Thr Pro Asn Glu Glu Cys Leu Phe Leu Glu Arg Leu Glu
65                  70                  75                  80

Glu Asn Gly Tyr Asn Thr Tyr Ile Ser Lys Lys His Gly Trp Tyr Leu
                85                  90                  95

Gly Ile Lys Lys Asn Gly Ser Val Lys Gly Thr His Tyr Gly Gln Lys
            100                 105                 110

Ala Ile Leu Phe Leu Val Leu Pro Val Ser Ser Asp
        115                 120

<210> SEQ ID NO 18
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Pro Val Leu Leu Tyr Cys Ser Asn Gly Gly His Tyr Leu Arg Ile Asn
1               5                   10                  15

Pro Asp Gly Thr Val Asp Gly Thr Arg Asp Arg Ser Asp Gln His Ile
            20                  25                  30

Gln Phe Gln Leu Ser Ala Glu Ser Val Gly Glu Val Tyr Ile Lys Ser
        35                  40                  45

Thr Glu Thr Gly Gln Tyr Leu Ala Ile Asn Pro Asp Gly Leu Val Tyr
50                  55                  60

Gly Ser Gln Thr Pro Asn Glu Glu Cys Leu Phe Leu Glu Arg Leu Glu
65                  70                  75                  80

Glu Asn Gly Tyr Asn Thr Tyr Ile Ser Lys Lys His Gly Trp Tyr Leu
                85                  90                  95

Gly Ile Asn Pro Asp Gly Ser Val Lys Gly Thr His Tyr Gly Gln Lys
            100                 105                 110

Ala Ile Leu Phe Leu Val Leu Pro Val Ser Ser Asp
        115                 120

<210> SEQ ID NO 19
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Pro Val Leu Leu Tyr Cys Ser Asn Gly Gly His Tyr Leu Arg Ile Asn
```

```
                1               5                   10                  15
            Pro Asp Gly Thr Val Asp Gly Thr Arg Asp Arg Ser Asp Gln His Ile
                                20                  25                  30

Gln Phe Gln Leu Ser Ala Glu Ser Val Gly Glu Val Tyr Ile Lys Ser
                        35                  40                  45

Thr Glu Thr Gly Gln Tyr Leu Ala Ile Asn Pro Asp Gly Leu Val Tyr
                    50                  55                  60

Gly Ser Gln Thr Pro Asn Glu Glu Cys Leu Phe Leu Glu Arg Leu Glu
             65                 70                  75                  80

Glu Asn Gly Tyr Asn Thr Tyr Ile Ser Lys Lys His Gly Trp Tyr Leu
                                85                  90                  95

Gly Ile Asn Pro Asp Gly Ser Val Lys Gly Thr His Tyr Gly Gln Lys
                            100                 105                 110

Ala Ile Leu Phe Leu Val Leu Pro Val Ser Ser Asp
                        115                 120
```

<210> SEQ ID NO 20
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
            Pro Val Leu Leu Tyr Cys Ser Asn Gly Gly His Tyr Leu Arg Ile Asn
             1               5                   10                  15

Pro Asp Gly Thr Val Asp Gly Thr Arg Asp Arg Ser Asp Gln His Ile
                                20                  25                  30

Gln Phe Gln Val Ser Ala Glu Ser Val Gly Glu Val Tyr Ile Lys Ser
                        35                  40                  45

Thr Glu Thr Gly Gln Tyr Leu Ala Ile Asn Pro Asp Gly Leu Val Tyr
                    50                  55                  60

Gly Ser Gln Thr Pro Asn Glu Glu Cys Leu Phe Leu Val Arg Leu Glu
             65                 70                  75                  80

Glu Asn Gly Tyr Val Thr Tyr Ile Ser Lys Lys His Gly Trp Tyr Leu
                                85                  90                  95

Gly Ile Asn Pro Asp Gly Ser Val Lys Gly Thr His Tyr Gly Gln Lys
                            100                 105                 110

Ala Ile Leu Phe Leu Val Leu Pro Val Ser Ser Asp
                        115                 120
```

<210> SEQ ID NO 21
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
            Pro Val Leu Leu Tyr Cys Ser Asn Gly Gly His Tyr Leu Arg Ile Asn
             1               5                   10                  15

Pro Asp Gly Thr Val Asp Gly Thr Arg Asp Arg Ser Asp Gln His Ile
                                20                  25                  30

Gln Phe Gln Val Ser Ala Glu Ser Val Gly Glu Val Tyr Leu Lys Ser
                        35                  40                  45

Thr Glu Thr Gly Gln Tyr Leu Ala Ile Asn Pro Asp Gly Leu Val Tyr
```

```
                 50                  55                  60
Gly Ser Gln Thr Pro Asn Glu Glu Cys Leu Phe Leu Val Arg Leu Glu
 65                  70                  75                  80

Glu Asn Gly Tyr Val Thr Leu Ile Ser Lys Lys His Gly Trp Tyr Leu
                 85                  90                  95

Gly Ile Asn Pro Asp Gly Ser Val Lys Gly Thr His Tyr Gly Gln Lys
                100                 105                 110

Ala Ile Leu Phe Leu Val Leu Pro Val Ser Ser Asp
                115                 120
```

<210> SEQ ID NO 22
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Pro Val Leu Leu Lys Ser Thr Glu Thr Gly Gln Tyr Leu Arg Ile Asn
  1               5                  10                  15

Pro Asp Gly Thr Val Asp Gly Thr Arg Asp Arg Ser Asp Gln His Ile
                 20                  25                  30

Gln Phe Gln Val Ser Pro Glu Gly Gly Gly Glu Val Leu Leu Lys Ser
                 35                  40                  45

Thr Glu Thr Gly Gln Tyr Leu Arg Ile Asn Pro Asp Gly Thr Val Asp
 50                  55                  60

Gly Thr Arg Asp Arg Ser Asp Gln His Ile Gln Phe Gln Val Ser Pro
 65                  70                  75                  80

Glu Gly Gly Gly Glu Val Leu Leu Lys Ser Thr Glu Thr Gly Gln Tyr
                 85                  90                  95

Leu Arg Ile Asn Pro Asp Gly Thr Val Asp Gly Thr Arg Asp Arg Ser
                100                 105                 110

Asp Gln His Ile Gln Phe Gln Val Ser Pro Glu Gly Gly Gly
                115                 120                 125
```

<210> SEQ ID NO 23
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Pro Val Leu Leu Lys Ser Thr Glu Thr Gly Gln Tyr Leu Arg Ile Asn
  1               5                  10                  15

Pro Asp Gly Thr Val Asp Gly Thr Arg Asp Arg Ser Asp Gln His Ile
                 20                  25                  30

Gln Phe Gln Val Ser Pro Glu Gly Gly Gly Glu Val Leu Leu Lys Ser
                 35                  40                  45

Thr Glu Thr Gly Gln Tyr Leu Arg Ile Asn Pro Asp Gly Thr Val Asp
 50                  55                  60

Gly Thr Arg Asp Arg Ser Asp Gln His Ile Gln Phe Gln Val Ser Pro
 65                  70                  75                  80

Glu Gly Gly Gly Glu Val Leu Leu Lys Ser Thr Glu Thr Gly Gln Tyr
                 85                  90                  95

Leu Arg Ile Asn Pro Asp Gly Thr Val Asp Gly Thr Arg Asp Arg Ser
```

```
                  100                 105                 110
Asp Gln His Ile Gln Phe Gln Val Ser Pro Glu Gly Gly Gly
            115                 120                 125

<210> SEQ ID NO 24
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Pro Val Leu Leu Lys Ser Thr Glu Thr Gly Gln Tyr Leu Arg Ile Asn
1               5                   10                  15

Pro Asp Gly Thr Val Asp Gly Thr Arg Asp Arg Ser Asp Gln His Ile
            20                  25                  30

Gln Phe Gln Ile Ser Pro Glu Gly Gly Gly Glu Val Leu Leu Lys Ser
        35                  40                  45

Thr Glu Thr Gly Gln Tyr Leu Arg Ile Asn Pro Asp Gly Thr Val Asp
    50                  55                  60

Gly Thr Arg Asp Arg Ser Asp Gln His Ile Gln Phe Gln Ile Ser Pro
65                  70                  75                  80

Glu Gly Gly Gly Glu Val Leu Leu Lys Ser Thr Glu Thr Gly Gln Tyr
                85                  90                  95

Leu Arg Ile Asn Pro Asp Gly Thr Val Asp Gly Thr Arg Asp Arg Ser
            100                 105                 110

Asp Gln His Ile Gln Phe Gln Ile Ser Pro Glu Gly Gly Gly
            115                 120                 125

<210> SEQ ID NO 25
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Val Leu Leu Lys Ser Thr Glu Thr Gly Gln Tyr Leu Arg Ile Asn
1               5                   10                  15

Pro Asp Gly Thr Val Asp Gly Thr Arg Asp Arg Ser Asp Gln His Ile
            20                  25                  30

Gln Phe Gln Ile Ser Pro Glu Gly Asn Gly Glu Val Leu Leu Lys Ser
        35                  40                  45

Thr Glu Thr Gly Gln Tyr Leu Arg Ile Asn Pro Asp Gly Thr Val Asp
    50                  55                  60

Gly Thr Arg Asp Arg Ser Asp Gln His Ile Gln Phe Gln Ile Ser Pro
65                  70                  75                  80

Glu Gly Asn Gly Glu Val Leu Leu Lys Ser Thr Glu Thr Gly Gln Tyr
                85                  90                  95

Leu Arg Ile Asn Pro Asp Gly Thr Val Asp Gly Thr Arg Asp Arg Ser
            100                 105                 110

Asp Gln His Ile Gln Phe Gln Ile Ser Pro Glu Gly Asn Gly
            115                 120                 125

<210> SEQ ID NO 26
<211> LENGTH: 126
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (114)..(114)
<223> OTHER INFORMATION: Any amino acid

<400> SEQUENCE: 26

Pro Val Leu Leu Lys Ser Thr Glu Thr Gly Gln Tyr Leu Arg Ile Asn
1               5                   10                  15

Pro Asp Gly Thr Val Asp Gly Thr Arg Asp Arg Ser Asp Xaa His Ile
            20                  25                  30

Gln Phe Gln Ile Ser Pro Glu Gly Asn Gly Glu Val Leu Leu Lys Ser
        35                  40                  45

Thr Glu Thr Gly Gln Tyr Leu Arg Ile Asn Pro Asp Gly Thr Val Asp
    50                  55                  60

Gly Thr Arg Asp Arg Ser Asp Xaa His Ile Gln Phe Gln Ile Ser Pro
65                  70                  75                  80

Glu Gly Asn Gly Glu Val Leu Leu Lys Ser Thr Glu Thr Gly Gln Tyr
                85                  90                  95

Leu Arg Ile Asn Pro Asp Gly Thr Val Asp Gly Thr Arg Asp Arg Ser
            100                 105                 110

Asp Xaa His Ile Gln Phe Gln Ile Ser Pro Glu Gly Asn Gly
        115                 120                 125

<210> SEQ ID NO 27
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Pro Val Leu Leu Lys Ser Thr Glu Thr Gly Gln Tyr Leu Arg Ile Asn
1               5                   10                  15

Pro Asp Gly Thr Val Asp Gly Thr Arg Asp Arg Ser Asp Pro His Ile
            20                  25                  30

Gln Phe Gln Ile Ser Pro Glu Gly Asn Gly Glu Val Leu Leu Lys Ser
        35                  40                  45

Thr Glu Thr Gly Gln Tyr Leu Arg Ile Asn Pro Asp Gly Thr Val Asp
    50                  55                  60

Gly Thr Arg Asp Arg Ser Asp Pro His Ile Gln Phe Gln Ile Ser Pro
65                  70                  75                  80

Glu Gly Asn Gly

<210> SEQ ID NO 28
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 28

Pro Val Leu Leu Lys Ser Thr Glu Thr Gly Gln Tyr Leu Arg Ile Asn
1               5                   10                  15

Pro Asp Gly Thr Val Asp Gly Thr Arg Asp Arg Ser Asp Pro His Ile
                20                  25                  30

Gln Phe Gln Ile Ser Pro Glu Gly Asn Gly
            35                  40
```